(12) United States Patent
Papkoff et al.

(10) Patent No.: US 8,906,369 B2
(45) Date of Patent: Dec. 9, 2014

(54) OVR110 ANTIBODY COMPOSITIONS AND METHODS OF USE

(71) Applicant: diaDexus, Inc., South San Francisco, CA (US)

(72) Inventors: Jackie Papkoff, San Francisco, CA (US); Gundo Diedrich, South San Francisco, CA (US); Shu-Hui Liu, Redwood City, CA (US); Agnes Nowakowski, Austin, TX (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 13/869,448

(22) Filed: Apr. 24, 2013

(65) Prior Publication Data
US 2013/0232589 A1 Sep. 5, 2013

Related U.S. Application Data

(62) Division of application No. 12/516,397, filed as application No. PCT/US2007/085585 on Nov. 27, 2007, now Pat. No. 8,444,971.

(60) Provisional application No. 60/861,657, filed on Nov. 27, 2006.

(51) Int. Cl.
*A61K 39/395* (2006.01)

(52) U.S. Cl.
USPC ....................................... 424/130.1

(58) Field of Classification Search
None
See application file for complete search history.

(56) References Cited

U.S. PATENT DOCUMENTS 7,619,068 B2 * 11/2009 Pilkington et al. ......... 530/387.1

FOREIGN PATENT DOCUMENTS

WO   WO 2004/101756   11/2004

OTHER PUBLICATIONS

International Search Report from PCT/US2007/085585, Aug. 5, 2008.
International Preliminary Report on Patentability from PCT/US2007/085585, Jun. 3, 2009.

* cited by examiner

*Primary Examiner* — Laura B Goddard
*Assistant Examiner* — Meera Natarajan
(74) *Attorney, Agent, or Firm* — Licata & Tyrrell P.C.; Keith R. McCollum

(57) ABSTRACT

Isolated antibodies and antigen binding fragments thereof directed against Ovr110 which is expressed by head and neck, ovarian, endometrial, kidney, pancreatic, lung or breast cancer are provided. Also provided are cells and methods for their production as well as methods for their use in killing an Ovr110-expressing cancer cells and alleviating or treating an Ovr110-expressing cancer in a mammal. The anti-Ovr110 antibodies modulate Ovr110 function or internalize upon binding to Ovr110 expressed by mammalian cells in vitro and in vivo. Compositions comprising an anti-Ovr110 antibody and a carrier as well as articles of manufacture or kits thereof are also provided. In addition, isolated nucleic acids encoding an anti-Ovr110 antibody, expression vectors containing the isolated nucleic acids, and host cells containing the vectors are provided.

4 Claims, 2 Drawing Sheets

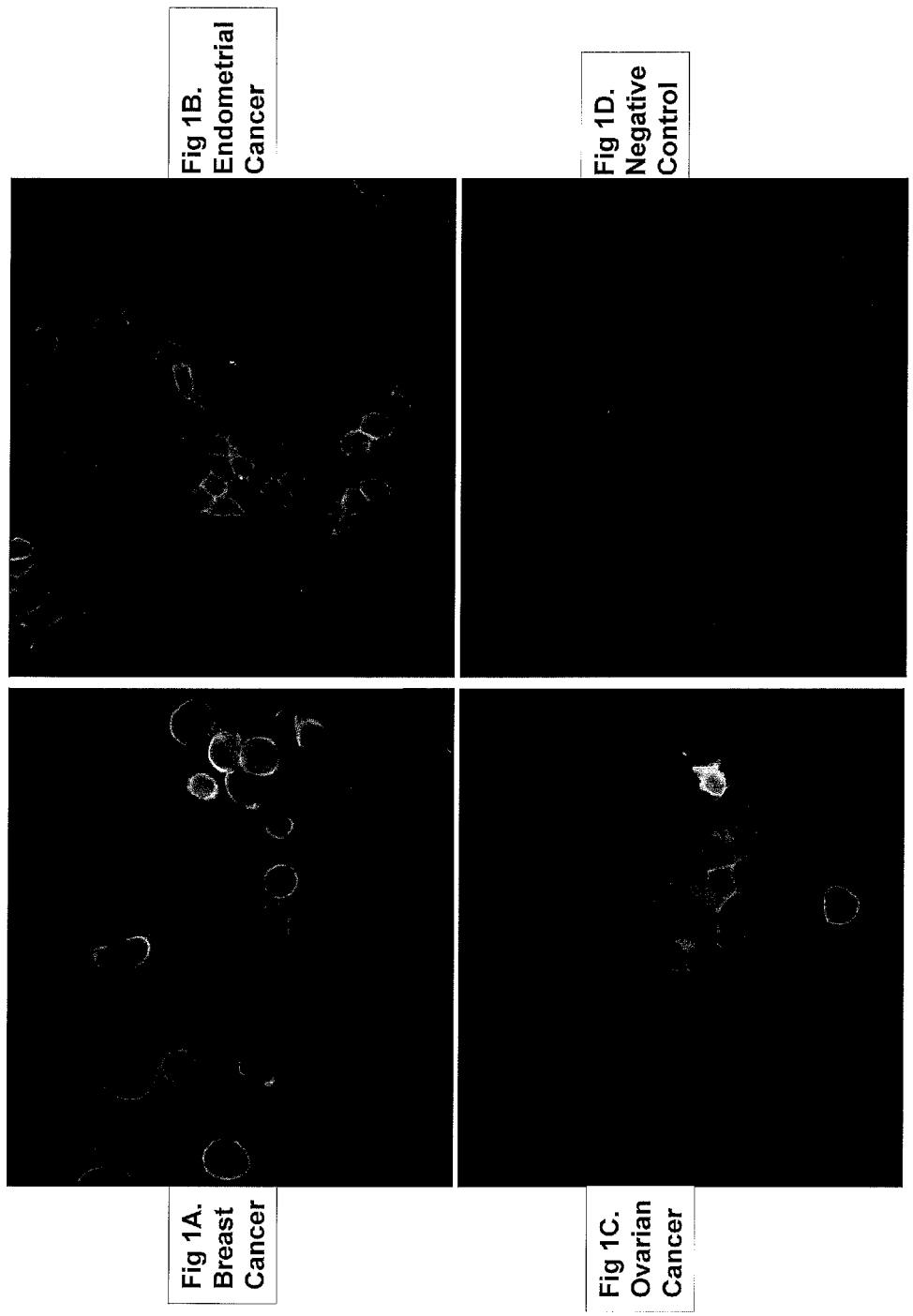

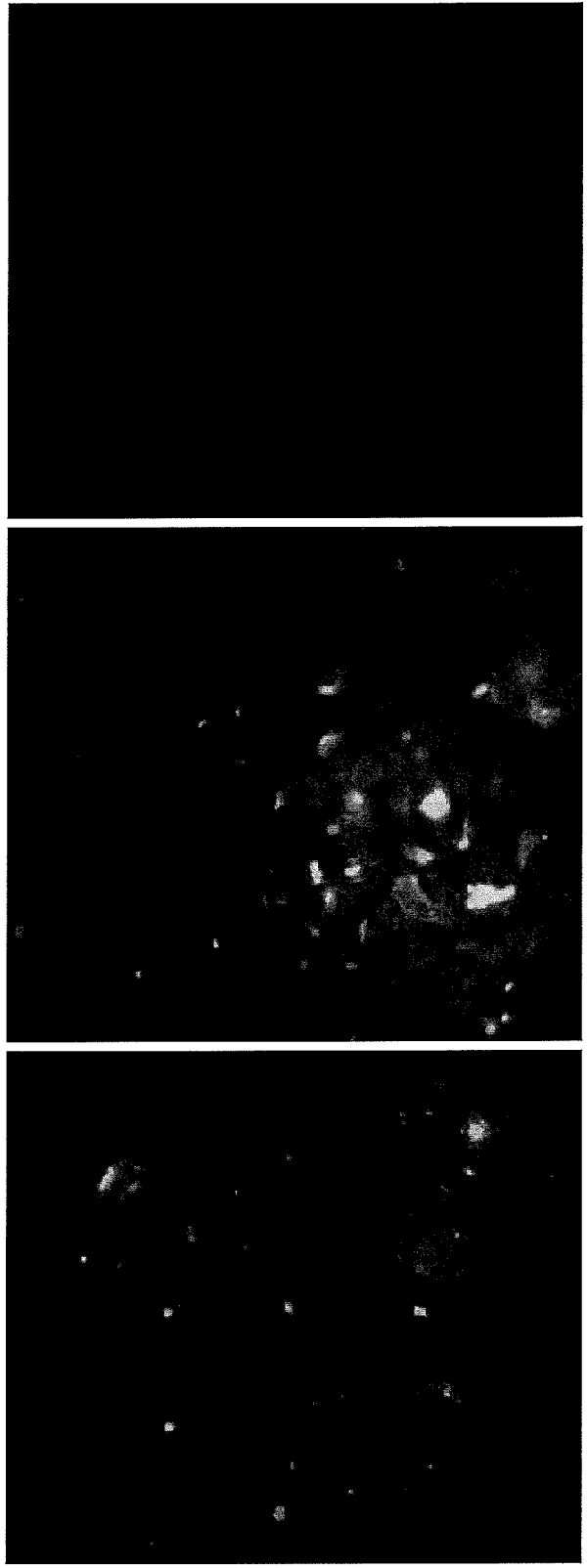

OVR110 ANTIBODY COMPOSITIONS AND METHODS OF USE

This patent application is a divisional of U.S. application Ser. No. 12/516,397, filed Dec. 21, 2009 which is the U.S. National Stage of PCT/US2007/085585, filed Nov. 27, 2007, and claims the benefit of priority from U.S. Provisional Application Ser. No. 60/861,657, filed Nov. 27, 2006, teachings of which are herein incorporated by reference in their entirety.

FIELD OF THE INVENTION

The present invention relates to anti-Ovr110 antibody compositions and methods of killing Ovr110-expressing ovarian, uterine, kidney, pancreatic, lung, breast or head & neck cancer cells. Additionally, the present invention relates to compositions and methods for treating human tumors with anti-Ovr110 antibodies.

BACKGROUND OF THE INVENTION

Ovarian Cancer

Cancer of the ovaries is the fourth-most common cause of cancer death in women in the United States, with more than 23,000 new cases and roughly 14,000 deaths predicted for the year 2001. Shridhar, V. et al., *Cancer Res.* 61(15): 5895-904 (2001); Memarzadeh, S. & Berek, J. S., *J. Reprod. Med.* 46(7): 621-29 (2001). The American Cancer Society (ACS) estimates that there will be about 25,580 new cases of ovarian cancer in 2004 and ovarian cancer will cause about 16,090 deaths in the United States. ACS Website: cancer with the extension .org of the world wide web. More women die annually from ovarian cancer than from all other gynecologic malignancies combined. The incidence of ovarian cancer in the US is estimated to 14.2 per 100,000 women per year and 9 women per 100,000 die every year from ovarian cancer. In 2004, approximately 70-75% of new diagnoses will be stage III and IV carcinoma with a predicted 5-year survival of ~15%. Jemal et al., Annual Report to the Nation on the Status of Cancer, 1975-2001, with a Special Feature Regarding Survival. Cancer 2004; 101: 3-27. The incidence of ovarian cancer is of serious concern worldwide, with an estimated 191,000 new cases predicted annually. Runnebaum, I. B. & Stickeler, E., *J. Cancer Res. Clin. Oncol.* 127(2): 73-79 (2001). Unfortunately, women with ovarian cancer are typically asymptomatic until the disease has metastasized. Because effective screening for ovarian cancer is not available, roughly 70% of women diagnosed have an advanced stage of the cancer with a five-year survival rate of ~25-30%. Memarzadeh, S. & Berek, J. S., supra; Nunns, D. et al., *Obstet. Gynecol. Surv.* 55(12): 746-51. Conversely, women diagnosed with early stage ovarian cancer enjoy considerably higher survival rates. Werness, B. A. & Eltabbakh, G. H., *Int'l. Gynecol. Pathol.* 20(1): 48-63 (2001). Although our understanding of the etiology of ovarian cancer is incomplete, the results of extensive research in this area point to a combination of age, genetics, reproductive, and dietary/environmental factors. Age is a key risk factor in the development of ovarian cancer: while the risk for developing ovarian cancer before the age of 30 is slim, the incidence of ovarian cancer rises linearly between ages 30 to 50, increasing at a slower rate thereafter, with the highest incidence being among septagenarian women. Jeanne M. Schilder et al., *Hereditary Ovarian Cancer: Clinical Syndromes and Management*, in Ovarian Cancer 182 (Stephen C. Rubin & Gregory P. Sutton eds., 2d ed. 2001).

With respect to genetic factors, a family history of ovarian cancer is the most significant risk factor in the development of the disease, with that risk depending on the number of affected family members, the degree of their relationship to the woman, and which particular first degree relatives are affected by the disease. Id. Mutations in several genes have been associated with ovarian cancer, including BRCA1 and BRCA2, both of which play a key role in the development of breast cancer, as well as hMSH2 and hMLH1, both of which are associated with hereditary non-polyposis colon cancer. Katherine Y. Look, *Epidemiology, Etiology, and Screening of Ovarian Cancer*, in Ovarian Cancer 169, 171-73 (Stephen C. Rubin & Gregory P. Sutton eds., 2d ed. 2001). BRCA1, located on chromosome 17, and BRCA2, located on chromosome 13, are tumor suppressor genes implicated in DNA repair; mutations in these genes are linked to roughly 10% of ovarian cancers. Id. at 171-72; Schilder et al., supra at 185-86. hMSH2 and hMLH1 are associated with DNA mismatch repair, and are located on chromosomes 2 and 3, respectively; it has been reported that roughly 3% of hereditary ovarian carcinomas are due to mutations in these genes. Look, supra at 173; Schilder et al., supra at 184, 188-89.

Reproductive factors have also been associated with an increased or reduced risk of ovarian cancer. Late menopause, nulliparity, and early age at menarche have all been linked with an elevated risk of ovarian cancer. Schilder et al., supra at 182. One theory hypothesizes that these factors increase the number of ovulatory cycles over the course of a woman's life, leading to "incessant ovulation," which is thought to be the primary cause of mutations to the ovarian epithelium. Id.; Laura J. Havrilesky & Andrew Berchuck, *Molecular Alterations in Sporadic Ovarian Cancer*, in Ovarian Cancer 25 (Stephen C. Rubin & Gregory P. Sutton eds., 2d ed. 2001). The mutations may be explained by the fact that ovulation results in the destruction and repair of that epithelium, necessitating increased cell division, thereby increasing the possibility that an undetected mutation will occur. Id. Support for this theory may be found in the fact pregnancy, lactation, and the use of oral contraceptives, all of which suppress ovulation, confer a protective effect with respect to developing ovarian cancer. Id.

Among dietary/environmental factors, there would appear to be an association between high intake of animal fat or red meat and ovarian cancer, while the antioxidant Vitamin A, which prevents free radical formation and also assists in maintaining normal cellular differentiation, may offer a protective effect. Look, supra at 169. Reports have also associated asbestos and hydrous magnesium trisilicate (talc), the latter of which may be present in diaphragms and sanitary napkins. Id. at 169-70.

Current screening procedures for ovarian cancer, while of some utility, are quite limited in their diagnostic ability, a problem that is particularly acute at early stages of cancer progression when the disease is typically asymptomatic yet is most readily treated. Walter J. Burdette, *Cancer: Etiology, Diagnosis, and Treatment* 166 (1998); Memarzadeh & Berek, supra; Runnebaum & Stickeler, supra; Werness & Eltabbakh, supra. Commonly used screening tests include biannual rectovaginal pelvic examination, radioimmunoassay to detect the CA-125 serum tumor marker, and transvaginal ultrasonography. Burdette, supra at 166. Currently, CA-125 is the only clinically approved serum marker for use in ovarian cancer. CA-125 is found elevated in the majority of serous cancers, but is elevated in only half of those women with early stage disease. The major clinical application of CA125 is in monitoring treatment success or detection of recurrence in women undergoing treatment for ovarian cancer. Markman M. *The Oncologist;* 2: 6-9 (1997). The use of CA125 as a screening marker is limited because it is frequently elevated in women with benign diseases such as endometriosis. Hence, there is a critical need for novel serum markers that are more sensitive and specific for the detection of ovarian cancer when used alone, or in combination with CA125. Bast R C. Et al., *Early Detection of Ovarian Cancer: Promise and Reality* in *Ovarian Cancer. Cancer Research and Treatment* Vol 107 (Stack M S, Fishman, D A, eds., 2001).

Pelvic examination has failed to yield adequate numbers of early diagnoses, and the other methods are not sufficiently accurate. Id. One study reported that only 15% of patients who suffered from ovarian cancer were diagnosed with the disease at the time of their pelvic examination. Look, supra at 174. Moreover, the CA-125 test is prone to giving false positives in pre-menopausal women and has been reported to be of low predictive value in post-menopausal women. Id. at 174-75. Although transvaginal ultrasonography is now the preferred procedure for screening for ovarian cancer, it is unable to distinguish reliably between benign and malignant tumors, and also cannot locate primary peritoneal malignancies or ovarian cancer if the ovary size is normal. Schilder et al., supra at 194-95. While genetic testing for mutations of the BRCA1, BRCA2, hMSH2, and hMLH1 genes is now available, these tests may be too costly for some patients and may also yield false negative or indeterminate results. Schilder et al., supra at 191-94.

Additionally, current efforts focus on the identification of panels of biomarkers that can be used in combination. Bast R C Jr., J Clin Oncol 2003; 21: 200-205. Currently, other markers being evaluated as potential ovarian serum markers which may serve as members of a multi-marker panel to improve detection of ovarian cancer are HE4; mesothelin; kallikrein 5, 8, 10 and 11; and prostasin. Urban et al. Ovarian cancer screening Hematol Oncol Clin North Am. 2003 August; 17(4):989-1005; Hellstrom et al. The HE4 (WFDC2) protein is a biomarker for ovarian carcinoma, Cancer Res. 2003 Jul. 1; 63(13):3695-700; Ordonez, Application of mesothelin immunostaining in tumor diagnosis, Am J Surg Pathol. 2003 November; 27(11):1418-28; Diamandis E P et al., Cancer Research 2002; 62: 295-300; Yousef G M et al., Cancer Research 2003; 63: 3958-3965; Kishi T et al., Cancer Research 2003; 63: 2771-2774; Luo L Y et al., Cancer Research 2003; 63: 807-811; Mok S C et al., J Natl Cancer Inst 2001; 93 (19): 1437-1439.

The staging of ovarian cancer, which is accomplished through surgical exploration, is crucial in determining the course of treatment and management of the disease. *AJCC Cancer Staging Handbook* 187 (Irvin D. Fleming et al. eds., 5th ed. 1998); Burdette, supra at 170; Memarzadeh & Berek, supra; Shridhar et al., supra. Staging is performed by reference to the classification system developed by the International Federation of Gynecology and Obstetrics. David H. Moore, *Primary Surgical Management of Early Epithelial Ovarian Carcinoma*, in *Ovarian Cancer* 203 (Stephen C. Rubin & Gregory P. Sutton eds., 2d ed. 2001); Fleming et al. eds., supra at 188. Stage I ovarian cancer is characterized by tumor growth that is limited to the ovaries and is comprised of three substages. Id. In substage IA, tumor growth is limited to one ovary, there is no tumor on the external surface of the ovary, the ovarian capsule is intact, and no malignant cells are present in ascites or peritoneal washings. Id. Substage IB is identical to A1, except that tumor growth is limited to both ovaries. Id. Substage IC refers to the presence of tumor growth limited to one or both ovaries, and also includes one or more of the following characteristics: capsule rupture, tumor growth on the surface of one or both ovaries, and malignant cells present in ascites or peritoneal washings. Id.

Stage II ovarian cancer refers to tumor growth involving one or both ovaries, along with pelvic extension. Id. Substage IIA involves extension and/or implants on the uterus and/or fallopian tubes, with no malignant cells in the ascites or peritoneal washings, while substage IIB involves extension into other pelvic organs and tissues, again with no malignant cells in the ascites or peritoneal washings. Id. Substage IIC involves pelvic extension as in IIA or JIB, but with malignant cells in the ascites or peritoneal washings. Id.

Stage III ovarian cancer involves tumor growth in one or both ovaries, with peritoneal metastasis beyond the pelvis confirmed by microscope and/or metastasis in the regional lymph nodes. Id. Substage IIIA is characterized by microscopic peritoneal metastasis outside the pelvis, with substage IIIB involving macroscopic peritoneal metastasis outside the pelvis 2 cm or less in greatest dimension. Id. Substage IIIC is identical to IIIB, except that the metastasis is greater than 2 cm in greatest dimension and may include regional lymph node metastasis. Id. Lastly, Stage IV refers to the presence distant metastasis, excluding peritoneal metastasis. Id.

While surgical staging is currently the benchmark for assessing the management and treatment of ovarian cancer, it suffers from considerable drawbacks, including the invasiveness of the procedure, the potential for complications, as well as the potential for inaccuracy. Moore, supra at 206-208, 213. In view of these limitations, attention has turned to developing alternative staging methodologies through understanding differential gene expression in various stages of ovarian cancer and by obtaining various biomarkers to help better assess the progression of the disease. Vartiainen, J. et al., *Int'l J. Cancer,* 95(5): 313-16 (2001); Shridhar et al. supra; Baekelandt, M. et al., *J. Clin. Oncol.* 18(22): 3775-81.

The treatment of ovarian cancer typically involves a multiprong attack, with surgical intervention serving as the foundation of treatment. Dennis S. Chi & William J. Hoskins, *Primary Surgical Management of Advanced Epithelial Ovarian Cancer*, in *Ovarian Cancer* 241 (Stephen C. Rubin & Gregory P. Sutton eds., 2d ed. 2001). For example, in the case of epithelial ovarian cancer, which accounts for ~90% of cases of ovarian cancer, treatment typically consists of: (1) cytoreductive surgery, including total abdominal hysterectomy, bilateral salpingo-oophorectomy, omentectomy, and lymphadenectomy, followed by (2) adjuvant chemotherapy with paclitaxel and either cisplatin or carboplatin. Eltabbakh, G. H. & Awtrey, C. S., *Expert Op. Pharmacother.* 2(10): 109-24. Despite a clinical response rate of 80% to the adjuvant therapy, most patients experience tumor recurrence within three years of treatment. Id. Certain patients may undergo a second cytoreductive surgery and/or second-line chemotherapy. Memarzadeh & Berek, supra.

From the foregoing, it is clear that procedures used for detecting, diagnosing, monitoring, staging, prognosticating, and preventing the recurrence of ovarian cancer are of critical importance to the outcome of the patient. Moreover, current procedures, while helpful in each of these analyses, are limited by their specificity, sensitivity, invasiveness, and/or their cost. As such, highly specific and sensitive procedures that would operate by way of detecting novel markers in cells, tissues, or bodily fluids, with minimal invasiveness and at a reasonable cost, would be highly desirable. Since survival is poor and the current treatment options do not contribute much to patient outcome (which is often is death) there is an urgent need for specific, effective therapies for ovarian cancer.

Accordingly, there is a great need for more sensitive and accurate methods for predicting whether a person is likely to develop ovarian cancer, for diagnosing ovarian cancer, for monitoring the progression of the disease, for staging the ovarian cancer, for determining whether the ovarian cancer has metastasized, and for imaging the ovarian cancer. There is also a need for better treatment of ovarian cancer.

Breast Cancer

Breast cancer, also referred to as mammary tumor cancer, is the second most common cancer among women, accounting for a third of the cancers diagnosed in the United States. One in nine women will develop breast cancer in her lifetime and about 192,000 new cases of breast cancer are diagnosed annually with about 42,000 deaths. Bevers, *Primary Prevention of Breast Cancer*, in *Breast Cancer*, 20-54 (Kelly K Hunt et al., ed., 2001); Kochanek et al., 49 *Nat'l. Vital Statistics Reports* 1, 14 (2001). Breast cancer is extremely rare in women younger than 20 and is very rare in women under 30. The incidence of breast cancer rises with age and becomes significant by age 50. White Non-Hispanic women have the highest incidence rate for breast cancer and Korean women have the lowest. Increased prevalence of the genetic mutations BRCA1 and BRCA2 that promote breast and other cancers are found in Ashkenazi Jews. African American women have the highest mortality rate for breast cancer among these same groups (31 per 100,000), while Chinese women have the lowest at 11 per 100,000. Although men can get breast cancer, this is extremely rare. In the United States it is estimated there will be 217,440 new cases of breast cancer and 40,580 deaths due to breast cancer in 2004. (American Cancer Society Website: cancer with the extension .org of the world wide web). With the exception of those cases with associated genetic factors, precise causes of breast cancer are not known.

In the treatment of breast cancer, there is considerable emphasis on detection and risk assessment because early and accurate staging of breast cancer has a significant impact on survival. For example, breast cancer detected at an early stage (stage T0, discussed below) has a five-year survival rate of 92%. Conversely, if the cancer is not detected until a late stage (i.e., stage T4 (IV)), the five-year survival rate is reduced to 13%. *AJCC Cancer Staging Handbook* pp. 164-65 (Irvin D. Fleming et al. eds., 5$^{th}$ ed. 1998). Some detection techniques, such as mammography and biopsy, involve increased discomfort, expense, and/or radiation, and are only prescribed only to patients with an increased risk of breast cancer.

Current methods for predicting or detecting breast cancer risk are not optimal. One method for predicting the relative risk of breast cancer is by examining a patient's risk factors and pursuing aggressive diagnostic and treatment regiments for high risk patients. A patient's risk of breast cancer has been positively associated with increasing age, nulliparity, family history of breast cancer, personal history of breast cancer, early menarche, late menopause, late age of first full term pregnancy, prior proliferative breast disease, irradiation of the breast at an early age and a personal history of malignancy. Lifestyle factors such as fat consumption, alcohol consumption, education, and socioeconomic status have also been associated with an increased incidence of breast cancer although a direct cause and effect relationship has not been established. While these risk factors are statistically significant, their weak association with breast cancer limited their usefulness. Most women who develop breast cancer have none of the risk factors listed above, other than the risk that comes with growing older. NIH Publication No. 00-1556 (2000).

Current screening methods for detecting cancer, such as breast self exam, ultrasound, and mammography have drawbacks that reduce their effectiveness or prevent their widespread adoption. Breast self exams, while useful, are unreliable for the detection of breast cancer in the initial stages where the tumor is small and difficult to detect by palpation. Ultrasound measurements require skilled operators at an increased expense. Mammography, while sensitive, is subject to over diagnosis in the detection of lesions that have questionable malignant potential. There is also the fear of the radiation used in mammography because prior chest radiation is a factor associated with an increase incidence of breast cancer.

At this time, there are no adequate methods of breast cancer prevention. The current methods of breast cancer prevention involve prophylactic mastectomy (mastectomy performed before cancer diagnosis) and chemoprevention (chemotherapy before cancer diagnosis) which are drastic measures that limit their adoption even among women with increased risk of breast cancer. Bevers, supra.

A number of genetic markers have been associated with breast cancer. Examples of these markers include carcinoembryonic antigen (CEA) (Mughal et al., *JAMA* 249:1881 (1983)), MUC-1 (Frische and Liu, *J. Clin. Ligand* 22:320 (2000)), HER-2/neu (Haris et al., *Proc. Am. Soc. Clin. Oncology* 15:A96 (1996)), uPA, PAI-1, LPA, LPC, RAK and BRCA (Esteva and Fritsche, *Serum and Tissue Markers for Breast Cancer*, in *Breast Cancer*, 286-308 (2001)). These markers have problems with limited sensitivity, low correlation, and false negatives which limit their use for initial diagnosis. For example, while the BRCA1 gene mutation is useful as an indicator of an increased risk for breast cancer, it has limited use in cancer diagnosis because only 6.2% of breast cancers are BRCA1 positive. Malone et al., *JAMA* 279:922 (1998). See also, Mewman et al., *JAMA* 279:915 (1998) (correlation of only 3.3%).

There are four primary classifications of breast cancer varying by the site of origin and the extent of disease development.

I. Ductal carcinoma in situ (DCIS): Malignant transformation of ductal epithelial cells that remain in their normal position. DCIS is a purely localized disease, incapable of metastasis.

II. Invasive ductal carcinoma (IDC): Malignancy of the ductal epithelial cells breaking through the basal membrane and into the supporting tissue of the breast. IDC may eventually spread elsewhere in the body.

III. Lobular carcinoma in situ (LCIS): Malignancy arising in a single lobule of the breast that fails to extend through the lobule wall, it generally remains localized.

IV. Infiltrating lobular carcinoma (ILC): Malignancy arising in a single lobule of the breast and invading directly through the lobule wall into adjacent tissues. By virtue of its invasion beyond the lobule wall, ILC may penetrate lymphatics and blood vessels and spread to distant sites.

For purpose of determining prognosis and treatment, these four breast cancer types have been staged according to the size of the primary tumor (T), the involvement of lymph nodes (N), and the presence of metastasis (M). Although DCIS by definition represents localized stage I disease, the other forms of breast cancer may range from stage II to stage IV. There are additional prognostic factors that further serve to guide surgical and medical intervention. The most common ones are total number of lymph nodes involved, ER (estrogen receptor) status, Her2/neu receptor status and histologic grades.

Breast cancers are diagnosed into the appropriate stage categories recognizing that different treatments are more effective for different stages of cancer. Stage TX indicates that primary tumor cannot be assessed (i.e., tumor was removed or breast tissue was removed). Stage T0 is characterized by abnormalities such as hyperplasia but with no evidence of primary tumor. Stage Tis is characterized by carcinoma in situ, intraductal carcinoma, lobular carcinoma in situ, or Paget's disease of the nipple with no tumor. Stage T1 (I) is characterized as having a tumor of 2 cm or less in the greatest dimension. Within stage T1, Tmic indicates microinvasion of 0.1 cm or less, T1a indicates a tumor of between 0.1 to 0.5 cm, T1b indicates a tumor of between 0.5 to 1 cm, and T1c indicates tumors of between 1 cm to 2 cm. Stage T2 (II) is characterized by tumors from 2 cm to 5 cm in the greatest dimension. Tumors greater than 5 cm in size are classified as stage T3 (III). Stage T4 (IV) indicates a tumor of any size with extension to the chest wall or skin. Within stage T4, T4a indicates extension of the tumor to the chess wall, T4b indicates edema or ulceration of the skin of the breast or satellite skin nodules confined to the same breast, T4c indicates a combination of T4a and T4b, and T4d indicates inflammatory carcinoma. *AJCC Cancer Staging Handbook* pp. 159-70 (Irvin D. Fleming et al. eds., 5$^{th}$ ed. 1998). In addition to standard staging, breast tumors may be classified according to their estrogen receptor and progesterone receptor protein status. Fisher et al., *Breast Cancer Research and Treatment* 7:147 (1986). Additional pathological status, such as HER2/neu status may also be useful. Thor et al., *J. Nat'l. Cancer Inst.* 90:1346 (1998); Paik et al., *J. Nat'l. Cancer Inst.* 90:1361 (1998); Hutchins et al., *Proc. Am. Soc. Clin. Oncology* 17:A2 (1998); and Simpson et al., *J. Clin. Oncology* 18:2059 (2000).

In addition to the staging of the primary tumor, breast cancer metastases to regional lymph nodes may be staged. Stage NX indicates that the lymph nodes cannot be assessed (e.g., previously removed). Stage N0 indicates no regional lymph node metastasis. Stage N1 indicates metastasis to movable ipsilateral axillary lymph nodes. Stage N2 indicates metastasis to ipsilateral axillary lymph nodes fixed to one another or to other structures. Stage N3 indicates metastasis to ipsilateral internal mammary lymph nodes. Id.

Stage determination has potential prognostic value and provides criteria for designing optimal therapy. Simpson et al., *J. Clin. Oncology* 18:2059 (2000). Generally, pathological staging of breast cancer is preferable to clinical staging because the former gives a more accurate prognosis. However, clinical staging would be preferred if it were as accurate as pathological staging because it does not depend on an invasive procedure to obtain tissue for pathological evaluation. Staging of breast cancer would be improved by detecting new markers in cells, tissues, or bodily fluids which could differentiate between different stages of invasion. Progress in this field will allow more rapid and reliable method for treating breast cancer patients.

Treatment of breast cancer is generally decided after an accurate staging of the primary tumor. Primary treatment options include breast conserving therapy (lumpectomy, breast irradiation, and surgical staging of the axilla), and modified radical mastectomy. Additional treatments include chemotherapy, regional irradiation, and, in extreme cases, terminating estrogen production by ovarian ablation.

Until recently, the customary treatment for all breast cancer was mastectomy. Fonseca et al., *Annals of Internal Medicine* 127:1013 (1997). However, recent data indicate that less radical procedures may be equally effective, in terms of survival, for early stage breast cancer. Fisher et al., *J. of Clinical Oncology* 16:441 (1998). The treatment options for a patient with early stage breast cancer (i.e., stage Tis) may be breast-sparing surgery followed by localized radiation therapy at the breast. Alternatively, mastectomy optionally coupled with radiation or breast reconstruction may be employed. These treatment methods are equally effective in the early stages of breast cancer.

Patients with stage I and stage II breast cancer require surgery with chemotherapy and/or hormonal therapy. Surgery is of limited use in Stage III and stage IV patients. Thus, these patients are better candidates for chemotherapy and radiation therapy with surgery limited to biopsy to permit initial staging or subsequent restaging because cancer is rarely curative at this stage of the disease. *AJCC Cancer Staging Handbook* 84, 164-65 (Irvin D. Fleming et al. eds., 5$^{th}$ ed. 1998).

In an effort to provide more treatment options to patients, efforts are underway to define an earlier stage of breast cancer with low recurrence which could be treated with lumpectomy without postoperative radiation treatment. While a number of attempts have been made to classify early stage breast cancer, no consensus recommendation on postoperative radiation treatment has been obtained from these studies. Page et al., *Cancer* 75:1219 (1995); Fisher et al., *Cancer* 75:1223 (1995); Silverstein et al., *Cancer* 77:2267 (1996).

Pancreatic Cancer

Pancreatic cancer is the thirteenth-most common cancer and eighth-most cause of cancer death worldwide. Donghui Li, *Molecular Epidemiology*, in *Pancreatic Cancer* 3 (Douglas B. Evans et al. eds., 2002). In the United States, cancer of the pancreas is the fourth-most common cancer in both males and females, accounting for five percent of cancer deaths and nearly 30,000 deaths overall. Id. The rates of pancreatic cancer are higher in men than women and higher in African-Americans as opposed to Caucasians. Id. at 9. The most significant predictor of pancreatic cancer is patient age; among Caucasians, the age-related incidence of pancreatic cancer increases continuously, even through the 85 and older category. Id. at 3. Approximately 80% of cases occur in the age range of 60 to 80, with those in their 80s experiencing a risk of acquiring the disease 40 times that of those in their 40s. Id. Furthermore, the American Cancer Society estimates that there will be about 31,800 new cases of pancreatic cancer in 2004 in the United States alone. Pancreatic cancer will cause about 31,200 deaths in the United States in the same year. ACS Website: cancer with the extension .org of the world wide web. Despite the efforts of researchers and physicians in devising treatments for pancreatic cancer, it remains almost universally fatal. James R. Howe, *Molecular Markers as a Tool for the Early Diagnosis of Pancreatic Cancer*, in *Pancreatic Cancer* 29 (Douglas B. Evans et al. eds., 2002).

Aside from age, a number of risk factors for pancreatic cancer have been identified, including smoking, diet, occupation, certain medical conditions, heredity, and molecular biologic. Smoking is the most important risk factor for acquiring the disease, with the link between smoking and pancreatic cancer being established in numerous studies. L1, supra at 3. The relative risk amounts to at least 1.5, increasing with the level of smoking to an outer risk ratio of 10-fold. Id. The next most important factor would appear to be diet, with increased risk associated with animal protein and fat intake, and decreased risk associated with intake of fruits and vegetables. Id. at 3-4. As for particular occupations, excessive rates of pancreatic cancer have been associated with workers in chemistry, coal and gas exploration, the metal industry, leather tanning, textiles, aluminum milling, and transportation. Id. at 4. A number of medical conditions have also been associated with an increased incidence of pancreatic cancer, including diabetes, chronic pancreatitis, gastrectomy, and cholecystectomy, although the cause and effect relationship between these conditions and pancreatic cancer has not been established. Id.

Hereditary genetic factors comprise less than 10% of the pancreatic cancer burden, with associations documented with hereditary pancreatitis, as well as germline mutations in familial cancer syndrome genes such as hMSH2 and hMLH1 (hereditary nonpolyposis colon cancer), p16 (familial atypical multiple mole-melanoma) and BRCA1/BRCA2 (breast and ovarian cancer). Id at 3. While no other organ has a higher inherited basis for cancer than the pancreas, researchers have been unable to pinpoint the particular genetic defect(s) that contribute to one's susceptibility to pancreatic cancer. David H. Berger & William E. Fisher, *Inherited Pancreatic Cancer Syndromes*, in *Pancreatic Cancer* 73 (Douglas B. Evans et al. eds., 2002).

From the standpoint of molecular biology, research has revealed an association between pancreatic cancer and a number of genetic mutations, including the activation of the proto-oncogene K-ras and the inactivation of the tumor suppressor genes p53, p16, and DPC4. Marina E. Jean et al., *The Molecular Biology of Pancreatic Cancer*, in *Pancreatic Cancer* 15 (Douglas B. Evans et al. eds., 2002).

In one study of pancreatic adenocarcinomas, 83% possessed K-ras activation along with inactivation of p16 and p53. Id. K-ras mutations are found in 80 to 95% of pancreatic adenocarcinomas, with p53, p16, and DPC4 genes being the must frequently deleted tumor suppressor genes in cancer of the pancreas. Howe, supra at 29. Homozygous deletions, hypermethylation, and mutations of the p16 gene have been discovered in 85 to 98% of adenocarcinomas of the pancreas. Id. As might be expected by the role of alterations in the K-ras, p. 53, p16, and DPC4 genes, loss of regulation of the cell cycle would appear to be key to tumorigenesis in the pancreas, and may explain why this cancer is so aggressive. Jean, supra at 15. Research has also revealed a link between this cancer and abnormal regulation of certain growth factors and growth factor receptors, as well as an upregulation of matrix metalloproteinases and tumor angiogenesis regulators. Id. Epidermal growth factor, fibroblast growth factor, transforming growth factor-β, insulin-like growth factor, hepatocyte growth factor, and vascular endothelial growth factor may play various roles in pancreatic cancer, although such roles have not be elucidated. Id. at 18-22.

The development of screening techniques to detect the presence of pancreatic cancer is particularly essential for this deadly cancer, as most patients fail to present until their pancreatic tumors obstruct the bile duct or induce pain, at which point the tumors have invaded the capillary and lymphatic vessels that surround the pancreas, Howe, supra at 29; unfortunately, patients with the metastatic form of the disease typically survive less than one year after diagnosis, Jean et al., supra at 15. While computed tomography (CT) and endoscopic retrograde cholangiopancreatography (ERCP) may assist in the diagnosis of symptomatic patients, there is presently no tool for screening for pancreatic tumors that would permit their early discovery, at which point they might be curable. Howe, supra at 29. Markers such as carcinoembryonic antigen, and antibodies generated against cell lines of human colonic cancer (CA 19-9 and CA 195), human ovarian cancer (CA 125), and human pancreatic cancer (SPAN-1 and DUPAN-2) may be elevated in the serum of patients with pancreatic cancer, but these markers are not sufficiently reliable to serve as screening tools due to their lack of specificity and appearance late in the disease. Walter J. Burdette, *Cancer: Etiology, Diagnosis, and Treatment* 99 (1998); Hasholzner, U. et al., *Anticancer Res.* 19(4A): 2477-80 (1999).

Due to the present lack of adequate screening methods, physicians are increasingly turning to techniques which employ methods of molecular biology as the most promising means for early diagnosis of the disease. Howe, supra at 30. At present, there is no high sensitivity, high specificity marker that enables the detection of pancreatic cancer in asymptomatic individuals, but several biological markers are under investigation. Id. Considerable efforts are currently focusing on K-ras, with researchers devising techniques to screen samples of pancreatic juice, bile, duodenal juice, or ERCP brushings to detect K-ras mutations. Id. Because the collection of these samples is invasive and not particularly helpful in screening those who are asymptomatic, researchers have also turned to serum and stool analysis for K-ras mutations, with the former being the most promising, as the latter is hindered by the complexity of the source material. Id. at 35-38, 42. Moreover, because serum levels of the transcription factor protein p53 may parallel cancer progression, p53 is likewise being studied as possible tumor marker. Id. at 37; Jean et al., supra at 17.

Once pancreatic cancer has been diagnosed, treatment decisions are made in reference to the stage of cancer progression. A number of imaging techniques are employed to stage pancreatic cancer, with computed tomography (CT) being the present method of choice, Harmeet Kaur et al., *Pancreatic Cancer: Radiologic Staging*, in *Pancreatic Cancer* 86 (Douglas B. Evans et al. eds., 2002); Ishiguchi, T. et al., *Hepatogastroenterology* 48(40): 923-27 (2001), despite the fact that it frequently underestimates the extent of the cancer, as small-volume metastases are often beyond the resolution of CT, H. J. Kim & K. C. Conlon, *Laparascopic Staging*, in *Pancreatic Cancer* 15 (Douglas B. Evans et al. eds., 2002). MRI may at some point supplant CT in view of, inter alia, its ability to (1) contrast among various tissue, (2) modify pulse sequences to improve visualization of lesions and minimize artifacts, (3) perform imaging while limiting a patient's exposure to ionizing radiation, and (4) visualize vessels without using IV iodinated contrast reagents. Kaur et al., supra at 87. At present, however, MRI has not demonstrated a clear advantage over CT. Kim & Conlon, supra at 116.

A variety of ultrasonic techniques are also currently employed in staging, including transabdominal ultrasound (TUS), endoscopic ultrasound (EUS), and intraoperative ultrasound (IUS), with EUS being one of the most promising. Kaur et al., supra at 86; Richard A. Erickson, *Endoscopic Diagnosis and Staging: Endoscopic Ultrasound, Endoscopic Retrograde Cholangiopancreatography*, in *Pancreatic Cancer* 97-106 (Douglas B. Evans et al. eds., 2002). These techniques, however, are each limited by a variety of factors: TUS is hindered by gas in the gastrointestinal tract and fat in the peritoneum, EUS requires considerable experience in ultrasonography and endoscopy and may not be widely available, and IUS can only be used intraoperatively. Kaur et al., supra at 86.

Although in its nascent stages, the search for markers that will assist in staging pancreatic cancer has found some possible leads. For example, research has revealed that two metastasis-suppressing genes, nm23-H1 and KAI1, are differentially expressed depending on the stage of pancreatic cancer, with their expression being upregulated at early stages and down regulated at later stages of the disease. Friess, H. et al., *J. Clin. Oncol.* 19(9): 2422-32 (2001). Researchers have also focused on genetic lymph node staging, particularly searching for mutations in the K-ras proto-oncogene. Yamada, T. et al., *Int'l J. Oncol.* 16(6): 1165-71 (2000). Likewise, research has identified that the presence of mutated K-ras sequences in plasma/serum is associated with late stage pancreatic cancer, although the presence of early stage pancreatic cancer can be detected this way as well. Sorenson, G. D., *Clin. Cancer Res.* 6(6): 2129-37 (2000). A promising staging technique using a multimarker reverse transcriptase-polymerase chain reaction assay has successfully distinguished pancreatic cancer stages by assaying blood and tissue samples for mRNA expression of the following tumor markers: the β-human chorionic gonadotropin gene, the hepatocyte growth factor receptor gene c-met, and the β-1,4-N-acetyl-galactosaminyl-transferase gene. Bilchik, A. et al., *Cancer* 88(5): 1037-44 (2000).

One classification system commonly used to stage pancreatic cancer is the TNM system devised by the Union Internationale Contre le Cancer. *AJCC Cancer Staging Handbook* 3 (Irvin D. Fleming et al. eds., 5$^{th}$ ed. 1998). This system is divided into several stages, each of which evaluates the extent of cancer growth with respect to primary tumor (T), regional lymph nodes (N), and distant metastasis (M). Id.

Stage 0 is characterized by carcinoma in situ (Tis), with no regional lymph node metastasis (N0) and no distant metastasis (M0). Id. at 113. Stages I and II differ from stage 0 only in terms of tumor category: stage I involves a tumor limited only to the pancreas that is either (1) 2 cm or less in greatest dimension (T1) or (2) more than 2 cm in greatest dimension (T2), while stage II involves a tumor that extends directly into the duodenum, bile duct, or peripancreatic tissues (T3). Id. Stage III involves tumor category T1, T2, or T3; regional lymph node metastasis (N1), which involves either a single lymph node (pN1a) or multiple lymph nodes (pN1b); and no distant metastasis (M0). Stage IVA is characterized by tumor extension directly into the stomach, spleen, colon, or adjacent large vessels (T4); any N category; and no distant metastasis (M0). Lastly, stage IVB is characterized by any T category, any N category, and distant metastasis (M1). Id.

Once the cancer has been staged, the only consistently effective treatment for the disease is surgery, and with only ten to fifteen percent of patients being able to undergo potentially curative resection. Jean et al., supra at 15; Fleming et al. eds., supra at 111; William F. Regine, *Postoperative Adjuvant Therapy: Past, Present, and Future Trial Development*, in *Pancreatic Cancer* 235 (Douglas B. Evans et al. eds., 2002). Moreover, the five-year survival of those patients undergoing resection is below twenty percent. Regine, supra at 235. While chemotherapeutic agents such as gemcitabine and 5-fluorouracil have shown some effectiveness against pancreatic carcinomas, the reality is that chemotherapy has shown little impact on survival from pancreatic cancer. Burdette, supra at 101. Radiation therapy has provided conflicting results with respect to its efficacy, id., although radiation in combination with 5-fluorouracil has shown some promise, Regine, supra at 235.

In view of the failure of conventional techniques at treating pancreatic cancer, a number of novel approaches employing the techniques of molecular biology have been investigated. Considerable research has been performed in the area of gene therapy, including antisense technology, gene-directed pro-drug activation strategies, promoter gene strategies, and oncolytic viral therapies. Eugene A. Choi & Francis R. Spitz, *Strategies for Gene Therapy*, in *Pancreatic Cancer* 331 (Douglas B. Evans et al. eds., 2002); Kasuya, H. et al., *Hepatogastroenterology* 48(40): 957-61 (2001). Other recent approaches have focused on the inhibition of matrix metalloproteinases, enzymes which facilitate the metastasis and invasion of tumor cells through their degradation of basement membranes, and their role in peritumoral stromal degradation and angiogenesis. Alexander S. Rosemurgy, II & Mahmudul Haq, *Role of Matrix Metalloproteinase Inhibition in the Treatment of Pancreatic Cancer*, in *Pancreatic Cancer* 369 (Douglas B. Evans et al. eds., 2002).

Angiogenesis in Cancer

Growth and metastasis of solid tumors are also dependent on angiogenesis. Folkman, J., 1986, *Cancer Research*, 46, 467-473; Folkman, J., 1989, *Journal of the National Cancer Institute*, 82, 4-6. It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites such as liver, lung or bone. Weidner, N., et al., 1991, *The New England Journal of Medicine*, 324(1), 1-8.

Angiogenesis, defined as the growth or sprouting of new blood vessels from existing vessels, is a complex process that primarily occurs during embryonic development. The process is distinct from vasculogenesis, in that the new endothelial cells lining the vessel arise from proliferation of existing cells, rather than differentiating from stem cells. The process is invasive and dependent upon proteolysis of the extracellular matrix (ECM), migration of new endothelial cells, and synthesis of new matrix components. Angiogenesis occurs during embryogenic development of the circulatory system; however, in adult humans, angiogenesis only occurs as a response to a pathological condition (except during the reproductive cycle in women).

Under normal physiological conditions in adults, angiogenesis takes place only in very restricted situations such as hair growth and wounding healing. Auerbach, W. and Auerbach, R., 1994, *Pharmacol Ther.* 63(3):265-3 11; Ribatti et al., 1991, *Haematologica* 76(4):3 11-20; Risau, 1997, *Nature* 386(6626):67 1-4. Angiogenesis progresses by a stimulus which results in the formation of a migrating column of endothelial cells. Proteolytic activity is focused at the advancing tip of this "vascular sprout", which breaks down the ECM sufficiently to permit the column of cells to infiltrate and migrate. Behind the advancing front, the endothelial cells differentiate and begin to adhere to each other, thus forming a new basement membrane. The cells then cease proliferation and finally define a lumen for the new arteriole or capillary.

Unregulated angiogenesis has gradually been recognized to be responsible for a wide range of disorders, including, but not limited to, cancer, cardiovascular disease, rheumatoid arthritis, psoriasis and diabetic retinopathy. Folkman, 1995, *Nat Med* 1(1):27-31; Isner, 1999, *Circulation* 99(13): 1653-5; Koch, 1998, *Arthritis Rheum* 41(6):951-62; Walsh, 1999, *Rheumatology* (Oxford) 38(2):103-12; Ware and Simons, 1997, *Nat Med* 3(2): 158-64.

Of particular interest is the observation that angiogenesis is required by solid tumors for their growth and metastases. Folkman, 1986 supra; Folkman 1990, *J Natl. Cancer Inst.*, 82(1) 4-6; Folkman, 1992, *Semin Cancer Biol* 3(2):65-71; Zetter, 1998, *Annu Rev Med* 49:407-24. A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. The precise mechanisms that control the angiogenic switch is not well understood, but it is believed that neovascularization of tumor mass results from the net balance of a multitude of angiogenesis stimulators and inhibitors Folkman, 1995, supra.

One of the most potent angiogenesis inhibitors is endostatin identified by O'Reilly and Folkman. O'Reilly et al., 1997, Cell 88(2):277-85; O'Reilly et al., 1994, Cell 79(2):3 15-28. Its discovery was based on the phenomenon that certain primary tumors can inhibit the growth of distant metastases. O'Reilly and Folkman hypothesized that a primary tumor initiates angiogenesis by generating angiogenic stimulators in excess of inhibitors. However, angiogenic inhibitors, by virtue of their longer half life in the circulation, reach the site of a secondary tumor in excess of the stimulators. The net result is the growth of primary tumor and inhibition of secondary tumor. Endostatin is one of a growing list of such angiogenesis inhibitors produced by primary tumors. It is a proteolytic fragment of a larger protein: endostatin is a 20 kDa fragment of collagen XVIII (amino acid H1132-K1315 in murine collagen XVIII). Endostatin has been shown to specifically inhibit endothelial cell proliferation in vitro and block angiogenesis in vivo. More importantly, administration of endostatin to tumor-bearing mice leads to significant tumor regression, and no toxicity or drug resistance has been observed even after multiple treatment cycles. Boehm et al., 1997, Nature 390(6658):404-407. The fact that endostatin targets genetically stable endothelial cells and inhibits a variety of solid tumors makes it a very attractive candidate for anticancer therapy. Fidler and Ellis, 1994, Cell 79(2):185-8; Gastl et al., 1997, Oncology 54(3):177-84; Hinsbergh et al., 1999, Ann Oncol 10 Suppl 4:60-3. In addition, angiogenesis inhibitors have been shown to be more effective when combined with radiation and chemotherapeutic agents. Klement, 2000, J. Clin Invest, 105(8) R15-24. Browder, 2000, Cancer Res. 6-(7) 1878-86, Arap et al., 1998, Science 279(5349): 377-80; Mauceri et al., 1998, Nature 394(6690):287-91.

As discussed above, each of the methods for diagnosing and staging ovarian, pancreatic, lung or breast cancer is limited by the technology employed. Accordingly, there is need for sensitive molecular and cellular markers for the detection of ovarian, pancreatic, lung or breast cancer. There is a need for molecular markers for the accurate staging, including clinical and pathological staging, of ovarian, pancreatic, lung or breast cancers to optimize treatment methods. In addition, there is a need for sensitive molecular and cellular markers to monitor the progress of cancer treatments, including markers that can detect recurrence of ovarian, pancreatic, lung or breast cancers following remission.

The present invention provides alternative methods of treating ovarian, pancreatic, lung or breast cancer that overcome the limitations of conventional therapeutic methods as well as offer additional advantages that will be apparent from the detailed description below.

Autoimmune Disease

Immune system cellular activity is controlled by a complex network of cell surface interactions and associated signaling processes. When a cell surface receptor is activated by its ligand a signal is sent to the cell, and, depending upon the signal transduction pathway that is engaged, the signal can be inhibitory or activatory. For many receptor systems cellular activity is regulated by a balance between activatory signals and inhibitory signals. In some of these it is known that positive signals associated with the engagement of a cell surface receptor by its ligand are downmodulated or inhibited by negative signals sent by the engagement of a different cell surface receptor by its ligand.

The biochemical mechanisms of these positive and negative signaling pathways have been studied for a number of known immune system receptor and ligand interactions. Many receptors that mediate positive signaling have cytoplasmic tails containing sites of tyrosine phosphatase phosphorylation known as immunoreceptor tyrosine-based activation motifs (ITAM). A common mechanistic pathway for positive signaling involves the activation of tyrosine kinases which phosphorylate sites on the cytoplasmic domains of the receptors and on other signaling molecules. Once the receptors are phosphorylated, binding sites for signal transduction molecules are created which initiate the signaling pathways and activate the cell. The inhibitory pathways involve receptors having immunoreceptor tyrosine based inhibitory motifs (ITIM), which, like the ITAMs, are phosphorylated by tyrosine kinases. Receptors having these motifs are involved in inhibitory signaling because these motifs provide binding sites for tyrosine phosphatases which block signaling by removing tyrosine from activated receptors or signal transduction molecules. While many of the details of the activation and inhibitory mechanisms are unknown, it is clear that functional balance in the immune system depends upon opposing activatory and inhibitory signals.

One example of immune system activity that is regulated by a balance of positive and negative signaling is B cell proliferation. The B cell antigen receptor is a B cell surface immunoglobulin which, when bound to antigen, mediates a positive signal leading to B cell proliferation. However, B cells also express Fc.gamma.RIIb1, a low affinity IgG receptor. When an antigen is part of an immune complex with soluble immunoglobulin, the immune complex can bind B cells by engaging both the B cell antigen receptor via the antigen and Fc.gamma.RIIb1 via the soluble immunoglobulin. Co-engagement of the Fc.gamma.RIIb1 with the B cell receptor complex downmodulates the activation signal and prevents B cell proliferation. Fc.gamma.RIIb1 receptors contain ITIM motifs which are thought to deliver inhibitory signals to B cells via interaction of the ITIMs with tyrosine phosphatases upon co-engagement with B cell receptors.

The cytolytic activity of Natural Killer (NK) cells is another example of immune system activity which is regulated by a balance between positive signals that initiate cell function and inhibitory signals which prevent the activity. The receptors that activate NK cytotoxic activity are not fully understood. However, if the target cells express cell-surface MHC class I antigens for which the NK cell has a specific receptor, the target cell is protected from NK killing. These specific receptors, known as Killer Inhibitory Receptors (KIRs) send a negative signal when engaged by their MHC ligand, downregulating NK cell cytotoxic activity.

KIRs belong to the immunoglobulin superfamily or the C-type lectin family (see Lanier et al., Immunology Today 17:86-91, 1996). Known human NK KIRs are members of the immunoglobulin superfamily and display differences and similarities in their extracellular, transmembrane and cytoplasmic regions. A cytoplasmic domain amino acid sequence common to many of the KIRs is an ITIM motif having the sequence YxxL/V. In some cases, it has been shown that phosphorylated ITIMs recruit tyrosine phosphatases which dephosphorylate molecules in the signal transduction pathway and prevent cell activation (see Burshtyn et al., Immunity 4:77-85, 1996). The KIRs commonly have two of these motifs spaced apart by 26 amino acids [YxxL/V(x).sub.26YxxL/V]. At least two NK cell receptors, each specific for a human leukocyte antigen (HLA) C allele (an MHC class I molecule), exist as an inhibitory and an activatory receptor. These receptors are highly homologous in the extracellular portions, but have major differences in their transmembrane and cytoplasmic portions. One of the differences is the appearance of the ITIM motif in the inhibitory receptor and the lack of the ITIM motif in the activating receptor (see Biassoni et al., Journal. Exp. Med, 183:645-650, 1996).

An immunoreceptor expressed by mouse mast cells, gp49B 1, also a member of the immunoglobulin superfamily, is known to downregulate cell activation signals and contains a pair of ITIM motifs. gp49B 1 shares a high degree of homology with human KIRs (Katz et al., Cell Biology, 93: 10809-10814, 1996). Mouse NK cells also express a family of immunoreceptors, the Ly49 family, which contain the ITIM motif and function in a manner similar to human KIRs. However, the Ly49 immunoreceptors have no structural homology with human KIRs and contain an extracellular C-type lectin domain, making them a member of the lectin superfamily of molecules (see Lanier et al., Immunology Today 17:86-91, 1996).

Clearly, the immune system activatory and inhibitory signals mediated by opposing kinases and phosphatases are very important for maintaining balance in the immune system. Systems with a predominance of activatory signals will lead to autoimmunity and inflammation. Immune systems with a predominance of inhibitory signals are less able to challenge infected cells or cancer cells. Isolating new activatory or inhibitory receptors is highly desirable for studying the biological signal(s) transduced via the receptor. Additionally, identifying such molecules provides a means of regulating and treating diseased states associated with autoimmunity, inflammation and infection.

For example engaging a ligand such as Ovr110 that interacts with a cell surface receptor having ITIM motifs with an antagonistic antibody or soluble receptor can be used to activate the specific immune function in disease states associated with suppressed immune function. On the other hand, using an antagonistic antibody specific to Ovr110 or a soluble form of the Ovr110 receptor can be used to block the interaction of Ovr110 with the cell surface receptor to reduce the specific immune function in disease states associated with increased immune function. Conversely, since receptors lacking the ITIM motif send activatory signals once engaged as described above, the effect of antibodies and soluble receptors is the opposite of that just described.

In another example, Ovr110 is thought to bind to a cell surface receptor (which may or may not have ITIM/ITAM motifs) and has been shown to have inhibitory effects on the immune system via macrophages such as T cells, B cells or other cell types. An Ovr110 antibody could block this inhibitory effect and enhance an immune response. This enhanced immune response could be beneficial in anti-tumor, anti-infective, anti-inflammation disease treatments.

Conversely, an agonist Ovr110 mAb has the opposite effect to induce inhibition of immune response. This is beneficial in scenarios such as tissue transplant where suppressed host immune response against the foreign tissue is desired.

In a further example, based on comparison to other B7 family members Ovr110 binds to an activating receptor on cells of the immune system or other cells (like tumor cells themselves) and sends a positive signal. In this case an antagonist Ovr110 mAb blocks receptor activation and an agonist Ovr110 mAb activates receptor activation.

As discussed above, methods for diagnosing and staging autoimmune diseases is limited by the technology employed. Accordingly, there is need for sensitive molecular and cellular markers for the detection of autoimmune diseases. There is a need for molecular markers for the accurate staging, including clinical and pathological staging, of autoimmune diseases to optimize treatment methods. In addition, there is a need for sensitive molecular and cellular markers to monitor the progress of autoimmune diseases treatments, including markers that can detect recurrence of autoimmune diseases following remission.

The present invention provides alternative methods of treating autoimmune diseases that overcome the limitations of conventional therapeutic methods as well as offer additional advantages that will be apparent from the detailed description below.

This invention also provides a method of treating cancer by either affecting the tumor cell directly or by modulating the immune response to the cancer.

SUMMARY OF THE INVENTION

This invention is directed to an isolated antibody, or antigen binding fragment thereof, wherein the antibody competes for binding to Ovr110 with a reference antibody comprising: a light chain variable region comprising an amino acid sequence selected from the group consisting of SEQ ID NOs: 2, 12, 22, 32 and 42; and a heavy chain variable region comprising an amino acid sequence selected from the group consisting of SEQ ID NOs: 7, 17, 27, 37 and 47. Further, the antibody is a monoclonal antibody, a human antibody, a humanized or a chimeric antibody.

The invention is further directed to an isolated monoclonal antibody, or antigen binding fragment thereof, comprising: a light chain variable region comprising CDR1, CDR2 and CDR3 sequences; and a heavy chain variable region comprising CDR1, CDR2, CDR3 sequences, wherein the light chain variable region CDR1 sequence comprises an amino acid sequence selected from the group consisting of SEQ ID NO: 3, 13, 23, 33 and 43, and conservative modifications thereof; the heavy chain variable region CDR1 sequence comprises an amino acid sequence selected from the group consisting of SEQ ID NO: 8, 18, 28, 38 and 48, and conservative modifications thereof; light chain variable region CDR2 sequence comprises an amino acid sequence selected from the group consisting of SEQ ID NO: 4, 14, 24, 34 and 44, and conservative modifications thereof; and the heavy chain variable region CDR2 sequence comprises an amino acid sequence selected from the group consisting of SEQ ID NO: 9, 19, 29, 39 and 49, and conservative modifications thereof; the light chain variable region CDR3 sequence comprises an amino acid sequence selected from the group consisting of SEQ ID NO: 5, 15, 25, 35 and 45, and conservative modifications thereof; and the heavy chain variable region CDR3 sequence comprises an amino acid sequence selected from the group consisting of SEQ ID NO: 10, 20, 30, 40 and 50, and conservative modifications thereof, and the antibody binds to Ovr110.

The invention is also directed to conjugated antibodies. They may be conjugated to a growth inhibitory agent or a cytotoxic agent. The cytotoxic agent may be selected from the group consisting of toxins, antibiotics, radioactive isotopes and nucleolytic enzymes and toxins. Examples of toxins include, but are not limited to, maytansin, maytansinoids, saporin, gelonin, ricin or calicheamicin.

The mammalian cell may be a cancer cell. Preferably, the anti-Ovr110 monoclonal antibody that inhibits the growth of Ovr110-expressing cancer cells in vivo. The mammalian cell may also be a normal cell.

The antibody may be produced in bacteria or in mammalian cells (or by other organisms not limited to plants, yeast). Preferably, the cancer is selected from the group consisting of ovarian, pancreatic, endometrial, lung and breast cancer. The invention is also directed to a method of producing the antibodies comprising culturing an appropriate cell and recovering the antibody from the cell culture.

The invention is also directed to compositions comprising the antibodies and a carrier. The antibody may be conjugated to a cytotoxic agent. The cytotoxic agent may be a radioactive isotope or other chemotherapeutic agent.

The invention is also directed to a method of killing an Ovr110-expressing cancer cell, comprising contacting the cancer cell with the antibodies of this invention, thereby killing the cancer cell. The cancer cell may be selected from the group consisting of head and neck, ovarian, pancreatic, lung and breast cancer cell.

The ovarian, or breast cancer may be ovarian serous adenocarcinoma or breast infiltrating ductal carcinoma or metastatic cancer. The breast cancer may be HER-2 negative breast cancer. The invention is also directed to a method of alleviating an Ovr110-expressing cancer in a mammal, comprising administering a therapeutically effective amount of the antibodies to the mammal.

In addition, the invention is directed to an article of manufacture comprising a container and a composition contained therein, wherein the composition comprises an antibody as described herein. The article of manufacture may also comprise an additional component, e.g., a package insert indicating that the composition can be used to treat ovarian, pancreatic, endometrial, lung or breast cancer.

The invention is also directed to a method for modulating the signaling of a negatively signaling immune cell Ovr110-receptor comprising binding Ovr110 with anti-Ovr110 antibody thereby reducing a suppressed immune function.

Additionally, the invention is directed to a method for modulating an immune response comprising binding Ovr110 with an anti-Ovr110 antibody thereby reducing a suppressed immune function. The modulation may be an increased immune response or a reduction of suppression of an immune response. The immune response may be against a cancer cell. The cancer cell may be selected from the group consisting of head and neck, ovarian, pancreatic, lung, endometrial and breast cancer. The immune response may be increased numbers of lymphocytes surrounding a tumor, increased infiltration of lymphocytes in a tumor, or increased activation of lymphocytes including T cells, B cells, NK cells and other immune cell types.

The invention is also directed to a method for increasing activation of lymphocytes comprising binding Ovr110 with an anti-Ovr110 antibody thereby reducing suppression of lymphocyte activation. The lymphocyte may be a T cell lymphocyte.

The invention may also be directed to a method for killing or inhibiting tumor cells by binding of an antibody to the tumor cell.

BRIEF DESCRIPTION OF THE FIGURES

FIG. 1: Immunofluorescence demonstrating binding of anti-Ovr110 antibody to the surface of live human tumor cells.

FIG. 2: Immunofluorescence demonstrating internalization of anti-Ovr110 antibody by live human tumor cells.

DETAILED DESCRIPTION OF THE INVENTION

Definitions and General Techniques

Human "Ovr110" as used herein, refers to a protein of 282 amino acids that is expressed on the cell surface as a glycoprotein, whose nucleotide and amino acid sequence sequences are as disclosed in e.g., WO 00/12758, Cancer specific gene (CSG) Ovr110; WO 99/63088, Membrane-bound protein PRO1291; WO00/36107, Human ovarian carcinoma antigen; WO 02/02624-A2, Human B7-like protein (B7-L), the disclosures of which are hereby expressly incorporated by reference. Since the Ovr110 protein contains a secretion signal peptide, amino acids 30-282 are located on the cell surface of the native mature protein. Ovr110 as used herein include allelic variants and conservative substitution mutants of the protein which have Ovr110 biological activity.

Ovr110 is known in the literature as B7x, B7H4, B7S1, B7-H4 or B7h.5. The RefSeq database at the NCBI annotates accession NM_024626 as "*Homo sapiens* V-set domain containing T cell activation inhibitor 1 (VTCN1), mRNA". This nucleotide and the encoded protein NP_078902.1 are given the following summary:

> B7H4 belongs to the B7 family (see CD80; MIM 112203) of costimulatory proteins. These proteins are expressed on the surface of antigen-presenting cells and interact with ligands (e.g., CD28; MIM 186760) on T lymphocytes. [supplied by OMIM].

A list of references discussing Ovr110 are listed below, the disclosure of which are hereby incorporated by reference.

Chen Y, Yang C, Xie Z, Zou L, Ruan Z, Zhang X, Tang Y, Fei L, Jia Z, Wu Y. Expression of the novel co-stimulatory molecule B7-H4 by renal tubular epithelial cells. Kidney Int. 2006 Oct. 18 [Epub]

Ou D, Wang X, Metzger D L, Ao Z, Pozzilli P, James R F, Chen L, Warnock G L. Suppression of human T-cell responses to beta-cells by activation of B7-H4 pathway. Cell Transplant. 2006; 15(5):399-410.

Suh W K, Wang S, Duncan G S, Miyazaki Y, Cates E, Walker T, Gajewska B U, Deenick E, Dawicki W, Okada H, Wakeham A, Itie A, Watts T H, Ohashi P S, Jordana M, Yoshida H, Mak T W. Generation and characterization of B7-H4/B7S1/B7x-deficient mice. Mol Cell Biol. 2006 September; 26(17):6403-11.

Krambeck A E, Thompson R H, Dong H, Lohse C M, Park E S, Kuntz S M, Leibovich B C, Blute M L, Cheville J C, Kwon E D. B7-H4 expression in renal cell carcinoma and tumor vasculature: associations with cancer progression and survival. Proc Natl Acad Sci USA. 2006 Jul. 5; 103 (27):10391-6. Epub 2006 Jun. 23.

Kryczek I, Wei S, Zou L, Zhu G, Mottram P, Xu H, Chen L, Zou W. Cutting edge: induction of B7-H4 on APCs through IL-10: novel suppressive mode for regulatory T cells. J Immunol. 2006 Jul. 1; 177(1):40-4.

Sun Y, Wang Y, Zhao J, Gu M, Giscombe R, Lefvert A K, Wang X. B7-H3 and B7-H4 expression in non-small-cell lung cancer. Lung Cancer. 2006 August; 53(2):143-51. Epub 2006 Jun. 19.

Bignotti E, Tassi R A, Calza S, Ravaggi A, Romani C, Rossi E, Falchetti M, Odicino F E, Pecorelli S, Santin A D. Differential gene expression profiles between tumor biopsies and short-term primary cultures of ovarian serous carcinomas: Identification of novel molecular biomarkers for early diagnosis and therapy. Gynecol Oncol. 2006 November; 103(2):405-16. Epub 2006 May 24.

Mao Y X, Chen Y J, Ge Y, Ma H B, Yu J F, Wu H Y, Hu Y M, Wang Q, Shi Q, Zhang X G. Recombinant human B7-H4 expressed in *Escherichia coli* inhibits T lymphocyte proliferation and IL-2 secretion in vitro. Acta Pharmacol Sin. 2006 June; 27(6):741-6.

Kryczek I, Zou L, Rodriguez P, Zhu G, Wei S, Mottram P, Brumlik M, Cheng P, Curiel T, Myers L, Lackner A, Alvarez X, Ochoa A, Chen L, Zou W. B7-H4 expression identifies a novel suppressive macrophage population in human ovarian carcinoma. J Exp Med. 2006 Apr. 17; 203(4):871-81. Epub 2006 Apr. 10.

Simon I, Zhuo S, Corral L, Diamandis E P, Sarno M J, Wolfert R L, Kim N R. B7-h4 is a novel membrane-bound protein and a candidate serum and tissue biomarker for ovarian cancer. Cancer Res. 2006 Feb. 1; 66(3):1570-5.

Tringler B, Liu W, Corral L, Torkko K C, Enomoto T, Davidson S, Lucia M S, Heinz D E, Papkoff J, Shroyer K R. B7-H4 overexpression in ovarian tumors. Gynecol Oncol. 2006 January; 100(1):44-52.

Ichikawa M, Chen L. Role of B7-H1 and B7-H4 molecules in down-regulating effector phase of T-cell immunity: novel cancer escaping mechanisms. Front Biosci. 2005 Sep. 1; 10:2856-60.

Collins M, Ling V, Carreno B M. The B7 family of immuneregulatory ligands. Genome Biol. 2005; 6(6):223. Epub 2005 May 31.

Salceda S, Tang T, Kmet M, Munteanu A, Ghosh M, Macina R, Liu W, Pilkington G, Papkoff J. The immunomodulatory protein B7-H4 is overexpressed in breast and ovarian cancers and promotes epithelial cell transformation. Exp Cell Res. 2005 May 15; 306(1):128-41.

Greenwald R J, Freeman G J, Sharpe A H. The B7 family revisited. Annu Rev Immunol. 2005; 23:515-48. Review.

Tringler B, Zhuo S, Pilkington G, Torkko K C, Singh M, Lucia M S, Heinz D E, Papkoff J, Shroyer K R. B7-h4 is highly expressed in ductal and lobular breast cancer. Clin Cancer Res. 2005 Mar. 1; 11(5):1842-8.

Sedy J R, Gavrieli M, Potter K G, Hurchla M A, Lindsley R C, Hildner K, Scheu S, Pfeffer K, Ware C F, Murphy T L, Murphy K M. B and T lymphocyte attenuator regulates T cell activation through interaction with herpesvirus entry mediator. Nat Immunol. 2005 January; 6(1):90-8. Epub 2004 Nov. 28.

Loke P, Allison J P. Emerging mechanisms of immune regulation: the extended B7 family and regulatory T cells. Arthritis Res Ther. 2004; 6(5):208-14. Epub 2004 Aug. 5. Review.

Wang S, Chen L. Co-signaling molecules of the B7-CD28 family in positive and negative regulation of T lymphocyte responses. Microbes Infect. 2004 July; 6(8):759-66. Review.

Choi I H, Zhu G, Sica G L, Strome S E, Cheville J C, Lau J S, Zhu Y, Flies D B, Tamada K, Chen L. Genomic organization and expression analysis of B7-H4, an immune inhibitory molecule of the B7 family. J Immunol. 2003 Nov. 1; 171(9):4650-4.

Carreno B M, Collins M. BTLA: a new inhibitory receptor with a B7-like ligand. Trends Immunol. 2003 October; 24(10):524-7. Review.

Prasad D V, Richards S, Mai X M, Dong C. B7S1, a novel B7 family member that negatively regulates T cell activation. Immunity. 2003 June; 18(6):863-73.

Sica G L, Choi I H, Zhu G, Tamada K, Wang S D, Tamura H, Chapoval A I, Flies D B, Bajorath J, Chen L. B7-H4, a molecule of the B7 family, negatively regulates T cell immunity. Immunity. 2003 June; 18(6):849-61.

Watanabe N, Gavrieli M, Sedy J R, Yang J, Fallarino F, Loftin S K, Hurchla M A, Zimmerman N, Sim J, Zang X, Murphy T L, Russell J H, Allison J P, Murphy K M. BTLA is a lymphocyte inhibitory receptor with similarities to CTLA-4 and PD-1. Nat Immunol. 2003 July; 4(7):670-9. Epub 2003 Jun. 8.

A group of three independent publications identified Ovr110 in mouse and human as new member of the T-cell B7 family of co-stimulatory molecules, an important class of molecules that very tightly regulate the activation/inhibition of T-cell function. Prasad et al., B7S1, a novel B7 family member that negatively regulates T cell activation, Immunity 18:863-73 (2003); Sica et al., B7-H4, a molecule of the B7 family, negatively regulates T cell immunity, Immunity 18:849-61 (2003); and Zang et al., B7x: a widely expressed B7 family member that inhibits T cell activation, Proc. Natl. Acad. Sci USA 100:10388-92 (2003). The predicted amino acid sequence of the mouse gene for B7S1 (Prasad 2003) was highly homologous to our previously identified Ovr110 molecule, and the predicted sequence of the human B7-H4/B7x (Sica 2003; Zang 2003) molecules were identical to Ovr110. Additional publications demonstrated overexpression of B7-H4 in various cancers including breast cancer (Tringer 2005; Salceda 2005), ovarian cancer (Salceda 2005; Tringer 2006, Simon 2006, Kryczek *J Exp Med* 2006; Bignotti 2006), lung cancer (Sun 2006) and renal cell carcinoma (Krambeck 2006; Chen 2006). Functional studies have further elucidated the association of B7-H4 with suppressive macrophage populations (Kryczek *J Exp Med* 2006), tumor vascularization (Krambeck 2006) and immuno-regulation including interleukin factor production and T cell activation, proliferation and tumor infiltration (Mao 2006; Kryczek *J Immunol* 2006).

We have previously generated and characterized anti-Ovr110 antibodies which are described in WO 2004/101756, WO 2006/053110, and WO2006/074418, which are hereby expressly incorporated by reference as part of the instant invention. Indirect immunofluorescent analysis by flow cytometry further confirmed the binding of our Ovr110 monoclonal antibodies to activated T-lymphocyte populations and tumor cells, as described by the authors above. These antibodies of the instant invention, those described previously and herein, specifically bind Ovr110 and have demonstrated characteristics which make them ideal therapeutic candidates for modulating B7-H4 functions including T cell (and other immune cell) regulation such as activation, proliferation and tumor infiltration, immune surveillance evasion (suppression of immune response), interleukin factor (IL-2, IL-6, IL-10, IL-x) production, tumor vascularization and beta cell activation. Furthermore, the antibodies of the instant invention are useful as therapeutic agents for those suffering from breast, ovarian, endometrial, lung, pancreatic, renal and head & neck cancers. The antibodies may have therapeutic effect by killing Ovr110 expressing cancer cells, inhibiting growth of Ovr110 expressing tumors, shrinking Ovr110 expressing tumors, extending survival time of individuals with Ovr110 expressing tumors, reducing metastases of Ovr110 expressing tumors, inducing immune response against Ovr110 expressing tumors, reducing inhibition of immune response against Ovr110 expressing tumors or reducing angiogenesis or vascularization of Ovr110 expressing tumors.

The term "antibody" (Ab) as used herein includes monoclonal antibodies, polyclonal antibodies, multispecific antibodies (e.g. bispecific antibodies), and antibody fragments, so long as they exhibit the desired biological activity. The term "immunoglobulin" (Ig) is used interchangeably with "antibody" herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. Preferably, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for [L and F isotypes. Each 6 L chain has at the N-terminus, a variable domain (VL) followed by a constant domain (CL) at its other end.

The VL is aligned with the VH and the CL is aligned with the first constant domain of the heavy chain (CHI).

Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Teff and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 1-10-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a P-sheet configuration, connected by three hypervariable regions, which form loops connecting, and in some cases forming part of, the P-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 5056 (L2) and 89-97 (L3) in the VL, and around about 1-35 (HI), 50-65 (H2) and 95-102 (113) in the VH; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (L1), 50-52 (L2) and 91-96 (U) in the VL, and 26-32 (HI), 53-55 (1-12) and 96-101 (H3) in the VH; Chothia and Lesk J. Mol. Biol. 196: 901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)) Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a CL and at least heavy chain constant domains, CHI, CH2 and CH3. The constant domains may be native sequence constant domains (e.g. human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CHI). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CHI domain including one or more cysteines from the antibody hinge region. Fab'-SH is the designation herein for Fab' in which the cysteine residue(s) of the constant domains bear a free thiol group. F(ab')2 antibody fragments originally were produced as pairs of 8 Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993), the disclosures of which are hereby expressly incorporated by reference.

A "native sequence" polypeptide is one which has the same amino acid sequence as a polypeptide (e.g., antibody) derived from nature. Such native sequence polypeptides can be isolated from nature or can be produced by recombinant or synthetic means. Thus, a native sequence polypeptide can have the amino acid sequence of a naturally occurring human polypeptide, murine polypeptide, or polypeptide from any other mammalian species.

The term "amino acid sequence variant" refers to a polypeptide that has amino acid sequences that differ to some extent from a native sequence polypeptide. Ordinarily, amino acid sequence variants of Ovr110 will possess at least about 70% homology with the native sequence Ovr110, preferably, at least about 80%, more preferably at least about 85%, even more preferably at least about 90% homology, and most preferably at least 95%. The amino acid sequence variants can possess substitutions, deletions, and/or insertions at certain positions within the amino acid sequence of the native amino acid sequence. Examples of Ovr110 variants arising from alternative transcript splicing include Ovr110v1 in WO 2004/053079 and dv-B7-H4 (Genebank Accession DQ103575 and Sun et al, supra), the disclosures of which are hereby expressly incorporated by reference. Antibodies of instant invention have therapeutic activity as discussed above to these variants of Ovr110.

The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcεRI.

"Homology" is defined as the percentage of residues in the amino acid sequence variant that are identical after aligning the sequences and introducing gaps, if necessary, to achieve the maximum percent homology. Methods and computer programs for the alignment are well known in the art. Sequence similarity may be measured by any common sequence analysis algorithm, such as GAP or BESTFIT or other variation Smith-Waterman alignment. See, T. F. Smith and M. S. Waterman, J. Mol. Biol. 147:195-197 (1981) and W. R. Pearson, Genomics 11:635-650 (1991).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

As used herein, an anti-Ovr110 antibody that "internalizes" is one that is taken up by (i.e., enters) the cell upon binding to Ovr110 on a mammalian cell (i.e. cell surface Ovr110). The internalizing antibody will of course include antibody fragments, human or humanized antibody and antibody conjugate. For therapeutic applications, internalization in vivo is contemplated. The number of antibody molecules internalized will be sufficient or adequate to kill an Ovr110-expressing cell, especially an Ovr110-expressing cancer cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the tumor cell.

Whether an anti-Ovr110 antibody internalizes upon binding Ovr110 on a mammalian cell can be determined by various assays including those described in the experimental examples below. For example, to test internalization in vivo, the test antibody is labeled and introduced into an animal known to have Ovr110 expressed on the surface of certain cells. The antibody can be radiolabeled or labeled with fluorescent or gold particles, for instance. Animals suitable for this assay include a mammal such as a nude mouse or a SCID mouse that contains a human Ovr110-expressing tumor transplant or xenograft, or a mouse into which cells transfected with human Ovr110 have been introduced, or a transgenic mouse expressing the human Ovr110 transgene. Appropriate controls include animals that did not receive the test antibody or that received an unrelated antibody, and animals that received an antibody to another antigen on the cells of interest, which antibody is known to be internalized upon binding to the antigen. The antibody can be administered to the animal, e.g., by intravenous injection or intraperitoneal injection. At suitable time intervals, sections of the tumor or tissue from the animal can be prepared using known methods or as described in the experimental examples below, and analyzed by light microscopy or electron microscopy, for binding and internalization as well as the location of the internalized antibody in the cell. Live animal imaging methods such as PET can also be used to demonstrate localization of the antibodies to the tumor. For internalization in vitro, the cells can be incubated in tissue culture dishes in the presence or absence of the relevant antibodies added to the culture media and processed for microscopic analysis at desired time points. The presence of an internalized, labeled antibody in the cells can be directly visualized by microscopy or by autoradiography if radiolabeled antibody is used. Alternatively, in a quantitative biochemical assay, a population of cells comprising Ovr110-expressing cells are contacted in vitro or in vivo with a radiolabeled test antibody and the cells (if contacted in vivo, cells are then isolated after a suitable amount of time) are treated with a protease or subjected to an acid wash to remove uninternalized antibody on the cell surface. The cells are ground up and the amount of protease resistant, radioactive counts per minute (cpm) associated with each batch of cells is measured by passing the homogenate through a scintillation counter. Based on the known specific activity of the radiolabeled antibody, the number of antibody molecules internalized per cell can be deduced from the scintillation counts of the ground-up cells. Cells are "contacted" with antibody in vitro preferably in solution form such as by adding the cells to the cell culture media in the culture dish or flask and mixing the antibody well with the media to ensure uniform exposure of the cells to the antibody. Instead of adding to the culture media, the cells can be contacted with the test antibody in an isotonic solution such as PBS in a test tube for the desired time period. In vivo, the cells are contacted with antibody by any suitable method of administering the test antibody such as the methods of administration described below when administered to a patient.

The faster the rate of internalization of the antibody upon binding to the Ovr110-expressing cell in vivo, the faster the desired killing or growth inhibitory effect on the target Ovr110-expressing cell can be achieved, e.g., by a cytotoxic immunoconjugate. Preferably, the kinetics of internalization of the anti-Ovr110 antibodies are such that they favor rapid killing of the Ovr110-expressing target cell. Therefore, it is desirable that the anti-Ovr110 antibody exhibit a rapid rate of internalization preferably, within 24 hours from administration of the antibody in vivo, more preferably within about 12 hours, even more preferably within about 30 minutes to 1 hour, and most preferably, within about 30 minutes. The present invention provides antibodies that internalize as fast as about 15 minutes from the time of introducing the anti-Ovr110 antibody in vivo or in vitro. The antibody will preferably be internalized into the cell within a few hours upon binding to Ovr110 on the cell surface, preferably within 1 hour, even more preferably within 15-30 minutes.

To determine if a test antibody can compete for binding to the same epitope as the epitope bound by the anti-Ovr110 antibodies of the present invention including the antibodies produced by the hybridomas deposited with the ATCC, a cross-blocking assay e.g., a competitive ELISA assay can be performed. In an exemplary competitive ELISA assay, Ovr110-coated wells of a microtiter plate, or Ovr110-coated sepharose beads, are pre-incubated with or without candidate competing antibody and then a biotin-labeled anti-Ovr110 antibody of the invention is added. The amount of labeled anti-Ovr110 antibody bound to the Ovr110 antigen in the wells or on the beads is measured using avidin-peroxidase conjugate and appropriate substrate.

Alternatively, the anti-Ovr110 antibody can be labeled, e.g., with a radioactive or fluorescent label or some other detectable and measurable label. The amount of labeled anti-Ovr110 antibody that binds to the antigen will have an inverse correlation to the ability of the candidate competing antibody (test antibody) to compete for binding to the same epitope on the antigen, i.e., the greater the affinity of the test antibody for the same epitope, the less labeled anti-Ovr-110 antibody will be bound to the antigen-coated wells. A candidate competing antibody is considered an antibody that binds substantially to the same epitope or that competes for binding to the same epitope as an anti-Ovr110 antibody of the invention if the candidate competing antibody can block binding of the anti-Ovr110 antibody by at least 20%, preferably by at least 20-50%, even more preferably, by at least 50% as compared to a control performed in parallel in the absence of the candidate competing antibody (but may be in the presence of a known noncompeting antibody). It will be understood that variations of this assay can be performed to arrive at the same quantitative value.

An antibody having a "biological characteristic" of a designated antibody, such as any of the monoclonal antibodies Ovr110.A7.1, Ovr110.A10.1, Ovr110.A13.1, Ovr110.A31.1, Ovr110.A57.1, Ovr110.A72.1 (previously identified as Ovr110 A22.1), Ovr110.A77.1, Ovr110.A87.1, Ovr110.A89, Ovr110.A 99.1, Ovr110.A102.1, Ovr110.A107, Ovr110.C1, Ovr110.C2, Ovr110.C3.2, Ovr110.C4, Ovr110.C5.1, Ovr110.C5.3, Ovr110.C6.3, Ovr110.C7.1, Ovr110.C8, Ovr110.C9.1, Ovr110.C10.1, Ovr110.C11.1, Ovr110.C12.1, Ovr110.C13, Ovr110.C14, Ovr110.C15, Ovr110.C16.1, Ovr110.C17.1, Ovr110.D9.1, Ovr110.I1, Ovr110.I2, Ovr110.I3, Ovr110.I4, Ovr110.I6, Ovr110.I7, Ovr110.I8, Ovr110.I9, Ovr110.I10, Ovr110.I11, Ovr110.I13, Ovr110.I14, Ovr110.I5, Ovr110.I16, Ovr110.I17, Ovr110.I18, Ovr110.I20, Ovr110.I21, Ovr110.I22, Ovr110.J1, Ovr110.J2, Ovr110.J3, Ovr110.Q1, Ovr110.Q3, Ovr110.Q4, Ovr110.Q5, Ovr110.Q6, Ovr110.Q7, Ovr110.Q8, Ovr110.Q9, Ovr110.Q10, Ovr110.Q11, Ovr110.Q12, Ovr110.Q13, Ovr110.Q14, Ovr110.Q15, Ovr110.Q16, Ovr110.Q17, Ovr110.Q18, Ovr110.Q19, Ovr110.Q20, Ovr110.Q21, Ovr110.Q23, Ovr110.Q24, Ovr110.Q25, Ovr110.Q26 and Ovr110.Q27 is one which possesses one or more of the biological characteristics of that antibody which distinguish it from other antibodies that bind to the same antigen, Ovr110.A7.1, Ovr110.A10.1, Ovr110.A13.1, Ovr110.A31.1, Ovr110.A57.1, Ovr110.A72.1 (previously identified as Ovr110A22.1), Ovr110.A77.1, Ovr110.A87.1, Ovr110.A89, Ovr110.A99.1, Ovr110.A102.1, Ovr110.A107, Ovr110.C1, Ovr110.C2, Ovr110.C3.2, Ovr110.C4, Ovr110.C5.1, Ovr110.C5.3, Ovr110.C6.3, Ovr110.C7.1, Ovr110.C8, Ovr110.C9.1, Ovr110.C10.1, Ovr110.C11.1, Ovr110.C12.1, Ovr110.C13, Ovr110.C14, Ovr110.C15, Ovr110.C16.1, Ovr110.C17.1, Ovr110.D9.1, Ovr110.I1, Ovr110.I2, Ovr110.I3, Ovr110.I4, Ovr110.I6, Ovr110.I7, Ovr110.I8, Ovr110.I9, Ovr110.I10, Ovr110.I11, Ovr110.I13, Ovr110.I14, Ovr110.I5, Ovr110.I16, Ovr110.I17, Ovr110.I18, Ovr110.I20, Ovr110.I21, Ovr110.I22, Ovr110.J1, Ovr110.J2, Ovr110.J3, Ovr110.Q1, Ovr110.Q3, Ovr110.Q4, Ovr110.Q5, Ovr110.Q6, Ovr110.Q7, Ovr110.Q8, Ovr110.Q9, Ovr110.Q10, Ovr110.Q11, Ovr110.Q12, Ovr110.Q13, Ovr110.Q14, Ovr110.Q15, Ovr110.Q16, Ovr110.Q17, Ovr110.Q18, Ovr110.Q19, Ovr110.Q20, Ovr110.Q21, Ovr110.Q23, Ovr110.Q24, Ovr110.Q25, Ovr110.Q26 and Ovr110.Q27 will bind the same epitope as that bound by Ovr110.A7.1, Ovr110.A10.1, Ovr110.A13.1, Ovr110.A31.1, Ovr110.A57.1, Ovr110.A72.1 (previously identified as Ovr110 A22.1), Ovr110.A77.1, Ovr110.A87.1, Ovr110.A89, Ovr110.A99.1, Ovr110.A102.1, Ovr110.A107, Ovr110.C1, Ovr110.C2, Ovr110.C3.2, Ovr110.C4, Ovr110.C5.1, Ovr110.C5.3, Ovr110.C6.3, Ovr110.C7.1, Ovr110.C8, Ovr110.C9.1, Ovr110.C10.1, Ovr110.C11.1, Ovr110.C12.1, Ovr110.C13, Ovr110.C14, Ovr110.C15, Ovr110.C16.1, Ovr110.C17.1, Ovr110.D9.1, Ovr110.I1, Ovr110.I2, Ovr110.I3, Ovr110.I4, Ovr110.I6, Ovr110.I7, Ovr110.I8, Ovr110.I9, Ovr110.I10, Ovr110.I11, Ovr110.I13, Ovr110.I14, Ovr110.I5, Ovr110.I16, Ovr110.I17, Ovr110.I18, Ovr110.I20, Ovr110.I21, Ovr110.I22, Ovr110.J1, Ovr110.J2, Ovr110.J3, Ovr110.Q1, Ovr110.Q3, Ovr110.Q4, Ovr110.Q5, Ovr110.Q6, Ovr110.Q7, Ovr110.Q8, Ovr110.Q9, Ovr110.Q10, Ovr110.Q11, Ovr110.Q12, Ovr110.Q13, Ovr110.Q14, Ovr110.Q15, Ovr110.Q16, Ovr110.Q17, Ovr110.Q18, Ovr110.Q19, Ovr110.Q20, Ovr110.Q21, Ovr110.Q23, Ovr110.Q24, Ovr110.Q25, Ovr110.Q26 and Ovr110.Q27 (e.g. which competes for binding or blocks binding of monoclonal antibody Ovr110.A7.1, Ovr110.A10.1, Ovr110.A13.1, Ovr110.A31.1, Ovr110.A57.1, Ovr110.A72.1 (previously identified as Ovr110 A22.1), Ovr110.A77.1, Ovr110.A87.1, Ovr110.A89, Ovr110.A99.1, Ovr110.A102.1, Ovr110.A107, Ovr110.C1, Ovr110.C2, Ovr110.C3.2, Ovr110.C4, Ovr110.C5.1, Ovr110.C5.3, Ovr110.C6.3, Ovr110.C7.1, Ovr110.C8, Ovr110.C9.1, Ovr110.C10.1, Ovr110.C11.1, Ovr110.C12.1, Ovr110.C13, Ovr110.C14, Ovr110.C15, Ovr110.C16.1, Ovr110.C17.1, Ovr110.D9.1, Ovr110.I1, Ovr110.I2, Ovr110.I3, Ovr110.I4, Ovr110.I6, Ovr110.I7, Ovr110.I8, Ovr110.I9, Ovr110.I10, Ovr110.I11, Ovr110.I13, Ovr110.I14, Ovr110.I5, Ovr110.I16, Ovr110.I17, Ovr110.I18, Ovr110.I20, Ovr110.I21, Ovr110.I22, Ovr110.J1, Ovr110.J2, Ovr110.J3, Ovr110.Q1, Ovr110.Q3, Ovr110.Q4, Ovr110.Q5, Ovr110.Q6, Ovr110.Q7, Ovr110.Q8, Ovr110.Q9, Ovr110.Q10, Ovr110.Q11, Ovr110.Q12, Ovr110.Q13, Ovr110.Q14, Ovr110.Q15, Ovr110.Q16, Ovr110.Q17, Ovr110.Q18, Ovr110.Q19, Ovr110.Q20, Ovr110.Q21, Ovr110.Q23, Ovr110.Q24, Ovr110.Q25, Ovr110.Q26 and Ovr110.Q27 to Ovr110, be able to target an Ovr110-expressing tumor cell in vivo and may internalize upon binding to Ovr110 on a mammalian cell in vivo. Likewise, an antibody with the biological characteristic of the Ovr110.A7.1, Ovr110.A10.1, Ovr110.A13.1, Ovr110.A31.1, Ovr110.A57.1, Ovr110.A72.1 (previously identified as Ovr110A22.1), Ovr110.A77.1, Ovr110.A87.1, Ovr110.A89, Ovr110.A99.1, Ovr110.A102.1, Ovr110.A107, Ovr110.C1, Ovr110.C2, Ovr110.C3.2, Ovr110.C4, Ovr110.C5.1, Ovr110.C5.3, Ovr110.C6.3, Ovr110.C7.1, Ovr110.C8, Ovr110.C9.1, Ovr110.C10.1, Ovr110.C11.1, Ovr110.C12.1, Ovr110.C13, Ovr110.C14, Ovr110.C15, Ovr110.C16.1, Ovr110.C17.1, Ovr110.D9.1, Ovr110.I1, Ovr110.I2, Ovr110.I3, Ovr110.I4, Ovr110.I6, Ovr110.I7, Ovr110.I8, Ovr110.I9, Ovr110.I10, Ovr110.I11, Ovr110.I13, Ovr110.I14, Ovr110.I5, Ovr110.I16, Ovr110.I17, Ovr110.I18, Ovr110.I20, Ovr110.I21, Ovr110.I22, Ovr110.J1, Ovr110.J2, Ovr110.J3, Ovr110.Q1, Ovr110.Q3, Ovr110.Q4, Ovr110.Q5, Ovr110.Q6, Ovr110.Q7, Ovr110.Q8, Ovr110.Q9, Ovr110.Q10, Ovr110.Q11, Ovr110.Q12, Ovr110.Q13, Ovr110.Q14, Ovr110.Q15, Ovr110.Q16, Ovr110.Q17, Ovr110.Q18, Ovr110.Q19, Ovr110.Q20, Ovr110.Q21, Ovr110.Q23, Ovr110.Q24, Ovr110.Q25, Ovr110.Q26 and Ovr110.Q27 antibody will have the same epitope binding, targeting, internalizing, tumor growth inhibitory and cytotoxic properties of the antibody.

The term "antagonist" antibody is used in the broadest sense, and includes an antibody that partially or fully blocks, inhibits, or neutralizes a biological activity of a native Ovr110 protein disclosed herein. Methods for identifying antagonists of an Ovr110 polypeptide may comprise contacting an Ovr110 polypeptide or a cell expressing Ovr110 on the cell surface, with a candidate antagonist antibody and measuring a detectable change in one or more biological activities normally associated with the Ovr110 polypeptide. An agonist antibody includes antibodies that enhance, activate or facilitate the function of Ovr110.

An "antibody that inhibits the growth of tumor cells expressing Ovr110" or a "growth inhibitory" antibody is one which binds to and results in measurable growth inhibition of cancer cells expressing or overexpressing Ovr110, in vitro or in vivo. Preferred growth inhibitory anti-Ovr110 antibodies inhibit growth of Ovr110-expressing tumor cells e.g., ovarian, pancreatic, endometrial, head & neck, kidney, lung or breast cancer cells) by greater than 20%, preferably from about 20% to about 50%, and even more preferably, by greater than 50% (e.g. from about 50% to about 100%) as compared to the appropriate control, the control typically being tumor cells not treated with the antibody being tested. Growth inhibition can be measured at an antibody concentration of about 0.1 to 30 pg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-Ovr110 antibody at about 1 pg/kg to about 100 mg/kg body weight results in reduction in tumor size or tumor cell proliferation within about 5 days to 3 months from the first administration of the antibody, preferably within about 5 to 30 days.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses Ovr110. Preferably the cell is a tumor cell, e.g. an ovarian, pancreatic, lung or breast cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cells in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRI1B contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126.330-41 (1995). Other FcRs, including those to be identified in the future, are encompassed by the term "FcR" herein. The term also includes the neonatal receptor, FcRn, which is responsible for the transfer, of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g. from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., J. Immunol. Methods 202:163 (1996) may be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

An "Ovr110-expressing cell" is a cell which expresses endogenous or transfected Ovr110 on the cell surface. An "Ovr110-expressing cancer" is a cancer comprising cells that have Ovr110 protein present on the cell surface. An "Ovr110-expressing cancer" produces sufficient levels of Ovr110 on the surface of cells thereof, such that an anti-Ovr110 antibody can bind thereto and have a therapeutic effect with respect to the cancer. A cancer which "overexpresses" Ovr110 is one which has significantly higher levels of Ovr110 at the cell surface thereof, compared to a noncancerous cell of the same tissue type. Such overexpression may be caused by gene amplification or by increased transcription or translation. Ovr110 overexpression may be determined in a diagnostic or prognostic assay by evaluating increased levels of the Ovr110 protein present on the surface of a cell (e.g. via an immunohistochemistry assay; FACS analysis). Alternatively, or additionally, one may measure levels of Ovr110-encoding nucleic acid or mRNA in the cell, e.g. via fluorescent in situ hybridization; (FISH; see WO98/45479 published October, 1998), Southern blotting, Northern blotting, or polymerase chain reaction (PCR) techniques, such as real time quantitative PCR (RT-PCR). One may also study Ovr110 overexpression by measuring antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. J. Immunol. Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody. An Ovr110-expressing cancer includes ovarian, pancreatic, endometrial, head & neck, kidney, lung or breast cancer. Bodily fluids include all internal, secreted, expelled and derivative fluids of the body such as blood, plasma, serum, urine, saliva, sputum, tears, ascites, peritoneal wash fluid, lymphatic fluid, bile, semen, puss, Amniotic fluid, Aqueous humour, Cerumen, Chyle, Chyme, Interstitial fluid, Menses, Milk, Mucus, Pleural fluid, sweat, Vaginal lubrication, vomit, cerebrospinal fluid and synovial fluid.

A "mammal" for purposes of treating a cancer or alleviating the symptoms of cancer, refers to any mammal, including-humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an Ovr110-expressing cancer if, after receiving a therapeutic amount of an anti-Ovr110 antibody according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis or angiogenesis; inhibition, to some extent, of tumor growth; and/or relief to some extent, one or more of the symptoms associated with the specific cancer; reduced morbidity and mortality, and improvement in quality of life issues. To the extent the anti-Ovr110 antibody may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR).

The term "therapeutically effective amount" refers to an amount of an antibody or a drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See preceding definition of "treating". To the extent the drug may prevent growth and/or kill existing cancer cells, it may be cytostatic and/or cytotoxic.

"Chronic" administration refers to administration of the agent(s) in a continuous mode as opposed to an acute mode, so as to maintain the initial therapeutic effect (activity) for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed.

Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, e.g., gelonin, ricin, saporin, and the various antitumor or anticancer agents disclosed below. Other cytotoxic agents are described below. A tumoricidal agent causes destruction of tumor cells.

A "growth inhibitory agent" when used herein refers to a compound or composition which inhibits growth of a cell, especially an Ovr110-expressing cancer cell, either in vitro or in vivo. Thus, the growth inhibitory agent may be one which significantly reduces the percentage of Ovr110-expressing cells in S phase. Examples of growth inhibitory agents include agents that block cell cycle progression (at a place other than S phase), such as agents that induce GI arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest GI also spill over into S-phase arrest, for example, DNA alkylating agents such as tamoxifen, prednisone, dacarbazine, mechlorethamine, cisplatin, methotrexate, 5-fluorouracil, and ara-C.

Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

The term "epitope tagged" used herein refers to a chimeric polypeptide comprising an anti-Ovr110 polypeptide fused to a "tag polypeptide". The anti-Ovr110 polypeptide may be an anti-Ovr110 antibody, or antigenic fragment thereof. The tag polypeptide has enough residues to provide an epitope against which an antibody can be made, yet is short enough such that it does not interfere with activity of the attached protein to which it is fused. The tag polypeptide is also preferably fairly unique so that the antibody against it does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The term "package insert" is used to refer to instructions customarily included in commercial packages of therapeutic products, that contain information about the indications, usage, dosage, administration, contraindications and/or warnings concerning the use of such therapeutic products.

An "isolated nucleic acid molecule" is a nucleic acid molecule, e.g., an RNA, DNA, or a mixed polymer, which is substantially separated from other genome DNA sequences as well as proteins or complexes such as ribosomes and polymerases, which naturally accompany a native sequence. The term embraces a nucleic acid molecule which has been removed from its naturally occurring environment, and includes recombinant or cloned DNA isolates and chemically synthesized analogues or analogues biologically synthesized by heterologous systems. A substantially pure nucleic acid molecule includes isolated forms of the nucleic acid molecule.

"Vector" includes shuttle and expression vectors and includes, e.g., a plasmid, cosmid, or phagemid. Typically, a plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in prokaryotic, e.g., bacterial, or eukaryotic cells. Suitable vectors are disclosed below.

The cell that produces an anti-Ovr110 antibody of the invention will include the parent hybridoma cell e.g., the hybridomas that are deposited with the ATCC, as well as bacterial, yeast and eukaryotic host cells into which nucleic acid encoding the antibodies have been introduced. Suitable host cells are disclosed below.

RNA interference refers to the process of sequence-specific post transcriptional gene silencing in animals mediated by short interfering RNAs (siRNA) (Fire et al., 1998, Nature, 391, 806). The corresponding process in plants is commonly referred to as post transcriptional gene silencing or RNA silencing and is also referred to as quelling in fungi. The process of post transcriptional gene silencing is thought to be an evolutionarily conserved cellular defense mechanism used to prevent the expression of foreign genes which is commonly shared by diverse flora and phyla (Fire et al., 1999, Trends Genet., 15, 358). Such protection from foreign gene expression may have evolved in response to the production of double stranded RNAs (dsRNA) derived from viral infection or the random integration of transposon elements into a host genome via a cellular response that specifically destroys homologous single stranded RNA or viral genomic RNA. The presence of dsRNA in cells triggers the RNAi response though a mechanism that has yet to be fully characterized. This mechanism appears to be different from the interferon response that results from dsRNA mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as dicer. Dicer is involved in the processing of the dsRNA into short pieces of dsRNA known as short interfering RNAs (siRNA) (Berstein et al., 2001, Nature, 409, 363). Short interfering RNAs derived from dicer activity are typically about 21-23 nucleotides in length and comprise about 19 base pair duplexes. Dicer has also been implicated in the excision of 21 and 22 nucleotide small temporal RNAs (stRNA) from precursor RNA of conserved structure that are implicated in translational control (Hutvagner et al., 2001, Science, 293, 834). The RNAi response also features an endonuclease complex containing a siRNA, commonly referred to as an RNA-induced silencing complex (RISC), which mediates cleavage of single stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

Short interfering RNA mediated RNAi has been studied in a variety of systems. Fire et al., 1998, Nature, 391, 806, were the first to observe RNAi in *C. Elegans*. Wianny and Goetz, 1999, Nature Cell Biol., 2, 70, describe RNAi mediated by dsRNA in mouse embryos. Hammond et al., 2000, Nature, 404, 293, describe RNAi in *Drosophila* cells transfected with dsRNA. Elbashir et al., 2001, Nature, 411, 494, describe RNAi induced by introduction of duplexes of synthetic 21-nucleotide RNAs in cultured mammalian cells including human embryonic kidney and HeLa cells. Recent work in *Drosophila* embryonic lysates (Elbashir et al., 2001, EMBO J., 20, 6877) has revealed certain requirements for siRNA length, structure, chemical composition, and sequence that are essential to mediate efficient RNAi activity. These studies have shown that 21 nucleotide siRNA duplexes are most active when containing two nucleotide 3'-overhangs. Furthermore, complete substitution of one or both siRNA strands with 2'-deoxy (2'-H) or 2'-O-methyl nucleotides abolishes RNAi activity, whereas substitution of the 3'-terminal siRNA overhang nucleotides with deoxy nucleotides (2'-H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, EMBO J., 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, Cell, 107, 309).

Studies have shown that replacing the 3'-overhanging segments of a 21-mer siRNA duplex having 2 nucleotide 3' overhangs with deoxyribonucleotides does not have an adverse effect on RNAi activity. Replacing up to 4 nucleotides on each end of the siRNA with deoxyribonucleotides has been reported to be well tolerated whereas complete substitution with deoxyribonucleotides results in no RNAi activity (Elbashir et al., 2001, EMBO J., 20, 6877). In addition, Elbashir et al., supra, also report that substitution of siRNA with 2'-O-methyl nucleotides completely abolishes RNAi activity. Li et al., International PCT Publication No. WO 00/44914, and Beach et al., International PCT Publication No. WO 01/68836 both suggest that siRNA "may include modifications to either the phosphate-sugar back bone or the nucleoside to include at least one of a nitrogen or sulfur heteroatom", however neither application teaches to what extent these modifications are tolerated in siRNA molecules nor provide any examples of such modified siRNA. Kreutzer and Limmer, Canadian Patent Application No. 2,359,180, also describe certain chemical modifications for use in dsRNA constructs in order to counteract activation of double stranded-RNA-dependent protein kinase PKR, specifically 2'-amino or 2'-O-methyl nucleotides, and nucleotides containing a 2'-O or 4'-C methylene bridge. However, Kreutzer and Limmer similarly fail to show to what extent these modifications are tolerated in siRNA molecules nor do they provide any examples of such modified siRNA.

Parrish et al., 2000, Molecular Cell, 6, 1977-1087, tested certain chemical modifications targeting the unc-22 gene in *C. elegans* using long (>25 nt) siRNA transcripts. The authors describe the introduction of thiophosphate residues into these siRNA transcripts by incorporating thiophosphate nucleotide analogs with T7 and T3 RNA polymerase and observed that "RNAs with two (phosphorothioate) modified bases also had substantial decreases in effectiveness as RNAi triggers (data not shown); (phosphorothioate) modification of more than two residues greatly destabilized the RNAs in vitro and we were not able to assay interference activities." Id. at 1081. The authors also tested certain modifications at the 2'-position of the nucleotide sugar in the long siRNA transcripts and observed that substituting deoxynucleotides for ribonucleotides "produced a substantial decrease in interference activity", especially in the case of Uridine to Thymidine and/or Cytidine to deoxy-Cytidine substitutions. Id. In addition, the authors tested certain base modifications, including substituting 4-thiouracil, 5-bromouracil, 5-iodouracil, 3-(aminoallyl) uracil for uracil, and inosine for guanosine in sense and antisense strands of the siRNA, and found that whereas 4-thiouracil and 5-bromouracil were all well tolerated, inosine "produced a substantial decrease in interference activity" when incorporated in either strand. Incorporation of 5-iodouracil and 3-(aminoally)uracil in the antisense strand resulted in substantial decrease in RNAi activity as well.

Beach et al., International PCT Publication No. WO 01/68836, describes specific methods for attenuating gene expression using endogenously derived dsRNA. Tuschl et al., International PCT Publication No. WO 01/75164, describes a *Drosophila* in vitro RNAi system and the use of specific siRNA molecules for certain functional genomic and certain therapeutic applications; although Tuschl, 2001, Chem. Biochem., 2, 239-245, doubts that RNAi can be used to cure genetic diseases or viral infection due "to the danger of activating interferon response". Li et al., International PCT Publication No. WO 00/44914, describes the use of specific dsRNAs for use in attenuating the expression of certain target genes. Zernicka-Goetz et al., International PCT Publication No. WO 01/36646, describes certain methods for inhibiting the expression of particular genes in mammalian cells using certain dsRNA molecules. Fire et al., International PCT Publication No. WO 99/32619, describes particular methods for introducing certain dsRNA molecules into cells for use in inhibiting gene expression. Plaetinck et al., International PCT Publication No. WO 00/01846, describes certain methods for identifying specific genes responsible for conferring a particular phenotype in a cell using specific dsRNA molecules. Mello et al., International PCT Publication No. WO 01/29058, describes the identification of specific genes involved in dsRNA mediated RNAi. Deschamps Depaillette et al., International PCT Publication No. WO 99/07409, describes specific compositions consisting of particular dsRNA molecules combined with certain anti-viral agents. Driscoll et al., International PCT Publication No. WO 01/49844, describes specific DNA constructs for use in facilitating gene silencing in targeted organisms. Parrish et al., 2000, Molecular Cell, 6, 1977-1087, describes specific chemically modified siRNA constructs targeting the unc-22 gene of *C. elegans*. Tuschl et al., International PCT Publication No. WO 02/44321, describe certain synthetic siRNA constructs.

Compositions and Methods of the Invention

The invention provides anti-Ovr110 antibodies. Preferably, the anti-Ovr110 antibodies internalize upon binding to cell surface Ovr110 on a mammalian cell. Alternatively, anti-Ovr110 antibodies inhibit Ovr110 function by binding to native Ovr110 protein on cells. The anti-Ovr110 antibodies may also destroy or lead to the destruction of tumor cells bearing Ovr110.

It was not apparent that Ovr110 was internalization-competent. In addition the ability of an antibody to internalize depends on several factors including the affinity, avidity, and isotype of the antibody, and the epitope that it binds. It is well known that not all antibody-antigen pairs exhibit the ability to internalize. We have demonstrated herein that the cell surface Ovr110 is internalization competent upon binding by the anti-Ovr110 antibodies of the invention. Additionally, it was demonstrated that the anti-Ovr110 antibodies of the present invention can specifically target Ovr110-expressing tumor cells in vitro and in vivo and inhibit or kill these cells. These in vivo tumor targeting, internalization and growth inhibitory properties of the anti-Ovr110 antibodies make these antibodies very suitable for therapeutic uses, e.g., in the treatment of various cancers including ovarian, pancreatic, endometrial, head & neck, kidney, lung or breast cancer. Internalization of the anti-Ovr110 antibody is preferred, e.g., if the antibody or antibody conjugate has an intracellular site of action and if the cytotoxic agent conjugated to the antibody does not readily cross the plasma membrane (e.g., the toxin calicheamicin). Internalization is not necessary if the antibodies or the agent conjugated to the antibodies do not have intracellular sites of action, e.g., if the antibody can kill the tumor cell by ADCC or some other mechanism.

The anti-Ovr110 antibodies of the invention also have various non-therapeutic applications. The anti-Ovr110 antibodies of the present invention can be useful for diagnosis and staging of Ovr110-expressing cancers (e.g., in radioimaging or other imaging methods). They may be used alone or in combination with other ovarian cancer markers, including, but not limited to, CA125, HE4 and mesothelin. The antibodies are also useful for purification or immunoprecipitation of Ovr110 from cells, for detection and quantitation of Ovr110 in vitro, e.g. in an ELISA or a Western blot or by IHC, to kill and eliminate Ovr110-expressing cells from a population of mixed cells as a step in the purification of other cells. The internalizing anti-Ovr110 antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies, an antibody sequence is fused to a heterologous polypeptide sequence. The antibodies can be modified in the Fc region to provide desired effector functions. As discussed in more detail in the sections below, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

The antibody may compete for binding, or binds substantially to, the same epitope bound by the antibodies of the invention. Antibodies having the biological characteristics of the present anti-Ovr110 antibodies of the invention are also contemplated, e.g., an anti-Ovr110 antibody which has the biological characteristics of a monoclonal antibody comprising SEQ ID NO: 1-50, specifically including the in vivo tumor targeting, internalization and any cell proliferation inhibition or cytotoxic characteristics. Specifically provided are anti-Ovr110 antibodies that bind to an epitope present in amino acids 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-282 or 21-35, 31-45, 41-55, 51-65, 61-75, 71-85, 81-95, 91-105, 101-115, 111-125, 121-135, 131-145, 141-155, 151-165, 161-175, 171-185, 181-195, 191-205, 201-215, 211-225, 221-235, 231-245, 241-255, 251-258 of human Ovr110.

Methods of producing the above antibodies are described in detail below.

The present anti-Ovr110 antibodies are useful for treating an Ovr110-expressing cancer or alleviating one or more symptoms of the cancer in a mammal. Such a cancer includes ovarian, pancreatic, lung or breast cancer, cancer of the urinary tract, lung cancer, breast cancer, colon cancer, pancreatic cancer, and ovarian cancer, more specifically, prostate adenocarcinoma, renal cell carcinomas, colorectal adenocarcinomas, lung adenocarcinomas, lung squamous cell carcinomas, and pleural mesothelioma. The cancers encompass metastatic cancers of any of the preceding, e.g., ovarian, pancreatic, lung or breast cancer metastases. The antibody is able to bind to at least a portion of the cancer cells that express Ovr110 in the mammal and preferably is one that does not induce or that minimizes HAMA response. Preferably, the antibody is effective to destroy or kill Ovr110-expressing tumor cells or inhibit the growth of such tumor cells, in vitro or in vivo, upon binding to Ovr110 on the cell. Such an antibody includes a naked anti-Ovr110 antibody (not conjugated to any agent). Naked anti-Ovr110 antibodies demonstrate efficacy in combination with another therapeutic agent such as a taxane or other drug used to treat cancer. Naked anti-Ovr110 antibodies having tumor growth inhibition properties in vivo include the antibodies described in the Experimental Examples below. In some cases the function of the naked antibodies may only be evident in combination with another chemotherapeutic agent such as a taxane or other drug used to treat cancer.

Naked antibodies that have cytotoxic or cell growth inhibition properties can be further conjugated with a cytotoxic agent to render them even more potent in tumor cell destruction. Cytotoxic properties can be conferred to an anti-Ovr110 antibody by, e.g., conjugating the antibody with a cytotoxic agent, to form an immunoconjugate as described below. The cytotoxic agent or a growth inhibitory agent is preferably a small molecule. Toxins such as maytansin, maytansinoids, saporin, gelonin, ricin or calicheamicin and analogs or derivatives thereof, are preferable.

The invention provides a composition comprising an anti-Ovr110 antibody of the invention, and a carrier. For the purposes of treating cancer, compositions can be administered to the patient in need of such treatment, wherein the composition can comprise one or more anti-Ovr110 antibodies present as an immunoconjugate or as the naked antibody. Further, the compositions can comprise these antibodies in combination with other therapeutic agents such as cytotoxic or growth inhibitory agents, including chemotherapeutic agents. The invention also provides formulations comprising an anti-Ovr110 antibody of the invention, and a carrier. The formulation may be a therapeutic formulation comprising a pharmaceutically acceptable carrier.

Another aspect of the invention is isolated nucleic acids encoding the internalizing anti-Ovr110 antibodies. Nucleic acids encoding both the H and L chains and especially the hypervariable region residues, chains which encode the native sequence antibody as well as variants, modifications and humanized versions of the antibody, are encompassed.

The invention also provides methods useful for treating an Ovr110-expressing cancer or alleviating one or more symptoms of the cancer in a mammal, comprising administering a therapeutically effective amount of an internalizing anti-Ovr110 antibody to the mammal. The antibody therapeutic compositions can be administered short term (acute) or chronic, or intermittent as directed by physician. Also provided are methods of inhibiting the growth of, and killing an Ovr110 expressing cell. Finally, the invention also provides kits and articles of manufacture comprising at least one antibody of this invention, preferably at least one internalizing anti-Ovr110 antibody of this invention. Kits containing anti-Ovr110 antibodies find use in detecting Ovr-110 expression, or in therapeutic or diagnostic assays, e.g., for Ovr110 cell killing assays or for purification and/or immunoprecipitation of Ovr110 from cells. For example, for isolation and purification of Ovr110, the kit can contain an anti-Ovr110 antibody coupled to a solid support, e.g., a tissue culture plate or beads (e.g., sepharose beads). Kits can be provided which contain antibodies for detection and quantitation of Ovr110 in vitro, e.g. in an ELISA or a Western blot. Such antibody useful for detection may be provided with a label such as a fluorescent or radiolabel.

Production of Anti-Ovr110 Antibodies

The following describes exemplary techniques for the production of the antibodies useful in the present invention. Some of these techniques are described further in Example 1. The Ovr110 antigen to be used for production of antibodies may be, e.g., the full length polypeptide or a portion thereof, including a soluble form of Ovr110 lacking the membrane spanning sequence, or synthetic peptides to selected portions of the protein.

Alternatively, cells expressing Ovr110 at their cell surface (e.g. CHO or NIH-3T3 cells transformed to overexpress Ovr110; ovarian, pancreatic, lung, breast or other Ovr110-expressing tumor cell line), or membranes prepared from such cells can be used to generate antibodies. The nucleotide and amino acid sequences of human and murine Ovr110 are available as provided above. Ovr110 can be produced recombinantly in and isolated from, prokaryotic cells, e.g., bacterial cells, or eukaryotic cells using standard recombinant DNA methodology. Ovr110 can be expressed as a tagged (e.g., epitope tag) or other fusion protein to facilitate its isolation as well as its identification in various assays.

Antibodies or binding proteins that bind to various tags and fusion sequences are available as elaborated below. Other forms of Ovr110 useful for generating antibodies will be apparent to those skilled in the art.

Tags

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). The FLAG-peptide (Hopp et al., BioTechnology, 6:1204-1210 (1988)) is recognized by an anti-FLAG M2 monoclonal antibody (Eastman Kodak Co., New Haven, Conn.). Purification of a protein containing the FLAG peptide can be performed by immunoaffinity chromatography using an affinity matrix comprising the anti-FLAG M2 monoclonal antibody covalently attached to agarose (Eastman Kodak Co., New Haven, Conn.). Other tag polypeptides include the KT3 epitope peptide [Martin et al., Science, 255:192-194 (1992)]; an α-tubulin epitope peptide (Skinner et al., J. Biol. Chenz., 266:15163-15166 (1991)); and the T7 gene protein peptide tag (Lutz-Freyermuth et al., Proc. Natl. Acad. Sci. USA, 87:6393-6397 (1990)).

Polyclonal Antibodies

Polyclonal antibodies are preferably raised in animals, preferably non-human animals, by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups. Conjugates also can be made in recombinant cell culture as protein fusions.

Animals are immunized against the antigen, immunogenic conjugates, or derivatives by combining, e.g., 5-100 pg of the protein or conjugate (for rabbits or mice, respectively) with 3 volumes of Freund's complete adjuvant and injecting the solution intradermally at multiple sites. One month later, the animals are boosted with $\frac{1}{5}$ to $\frac{1}{10}$ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by recombinant DNA methods (U.S. Pat. No. 4,816,567). In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a "fusion partner", e.g., a myeloma cell line using a suitable fusing agent, such as polyethylene glycol, to form a hybridoma cell (Goding, Monoclonal Antibodies. Principles and Practice, pp 103 (Academic Press, 1986)).

The hybridoma cells thus prepared are seeded and grown in a suitable culture medium which medium preferably contains one or more substances that inhibit the growth or survival of the unfused, fusion partner, e.g., the parental myeloma cells. For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-I I mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980). Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp 103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transformed or transfected into prokaryotic or eukaryotic host cells such as, e.g., E. coli cells, simian COS cells, Chinese Hamster Ovary (CHO) cells, or myeloma cells, that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Phuckthun, Immunol. Revs., 130:151-188 (1992).

Further, the monoclonal antibodies or antibody fragments can be isolated from antibody phage libraries generated using the techniques described in McCafferty et al., Nature, 348: 552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The nonimmunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized Antibodies

Methods for humanizing non-human antibodies have been described in the art. Preferably, a humanized antibody has one or more amino acid residues introduced into it from a source which is nonhuman. These non-human amino acid residues are often referred to as "import" residues, which are typically taken from an "import" variable domain. Humanization can be essentially performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-Ovr110 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); 5,545,807; and alternatively, phage display technology (McCafferty et al., Nature 348: 552-553 (1990)) can be used to produce human antibodies and antibody fragments in vitro, from immunoglobulin variable (V) domain gene repertoires from unimmunized donors.

According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905. As discussed above, human antibodies may also be generated by in vitro activated B cells (see U.S. Pat. Nos. 5,567,610 and 5,229,275).

Antibody Fragments

In certain circumstances there are advantages of using antibody fragments, rather than whole antibodies. The smaller size of the fragments allows for rapid clearance, and may lead to improved access to solid tumors. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form $F(ab)_2$ fragments (Carter et al., Bio/Technology 10: 163-167 (1992)). According to another approach, $F(ab)_2$ fragments can be isolated directly from recombinant host cell culture. Fab and $F(ab)_2$ fragment with increased in vivo half-life comprising a salvage receptor binding epitope residues are described in U.S. Pat. No. 5,869,046. Other techniques for the production of antibody fragments will be apparent to the skilled practitioner. The antibody of choice may also be a single chain Fv fragment (scFv). See WO 93/16185; U.S. Pat. No. 5,571,894; and U.S. Pat. No. 5,587,458, the disclosures of which are hereby expressly incorporated by reference. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of the Ovr110 protein. Other such antibodies may combine an Ovr110 binding site with a binding site for another protein. Alternatively, an anti-Ovr110.Arm may be combined with an arm which binds to a triggering molecule on a leukocyte such as a Tcell receptor molecule (e.g. C133), or Fc receptors for IgG (FcγR), such as FcγRI (CD64), FcγRII (CD32) and FcγRIII (CD16), so as to focus and localize cellular defense mechanisms to the Ovr110-expressing cell. Bispecific antibodies may also be used to localize cytotoxic agents to cells which express Ovr110. These antibodies possess an Ovr110-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab)2 bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody. WO 96/16673, U.S. Pat. No. 5,837,234, WO98/02463, U.S. Pat. No. 5,821, 337 are hereby expressly incorporated by reference Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991), the disclosures of which are hereby expressly incorporated by reference.

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region (CHI) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Preferably, the bispecific antibodies in this approach are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690, the disclosure of which is hereby expressly incorporated by reference. For further details of generating bispecific antibodies see, for example, Suresh et al., Methods in Enzymology, 121:210 (1986).

According to another approach described in U.S. Pat. No. 5,731,168 (the disclosure of which is hereby expressly incorporated by reference), the interface between a pair of antibody molecules can be engineered to maximize the percentage of heterodimers which are recovered from recombinant cell culture. The preferred interface comprises at least a part of the CH3 domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980, the disclosure of which is hereby expressly incorporated by reference), and for treatment of HIV infection (WO 91/00360, WO 92/200373, and EP 03089, the disclosures of which are hereby expressly incorporated by reference). Heteroconjugate antibodies may be made using any convenient cross-linking methods. Suitable cross-linking agents are well known in the art, and are disclosed in U.S. Pat. No. 4,676,980 (the disclosure of which is hereby expressly incorporated by reference), along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

The "diabody" technology described by Hollinger et al., Proc. Natl. Acad. Sci. USA, 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1(X1n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CHI-flexible linker-VH-CHI-Fc region chain; or VH-CHI-VH-CHI-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Other Amino Acid Sequence Modifications

Amino acid sequence modification(s) of the anti-Ovr110 antibodies described herein are contemplated. For example, it may be desirable to improve the binding affinity and/or other biological properties of the antibody. Amino acid sequence variants of the anti-Ovr110 antibody are prepared by introducing appropriate nucleotide changes into the anti-Ovr110 antibody nucleic acid, or by peptide synthesis.

Such modifications include, for example, deletions from, and/or insertions into, and/or substitutions of, residues within the amino acid sequences of the anti-Ovr110 antibody. Any combination of deletion, insertion, and substitution is made to arrive at the final construct, provided that the final construct possesses the desired characteristics. The amino acid changes also may alter post-translational processes of the anti-Ovr110 antibody, such as changing the number or position of glycosylation sites.

A useful method for identification of certain residues or regions of the anti-Ovr110 antibody that are preferred locations for mutagenesis is called "alanine scanning mutagenesis" as described by Cunningham and Wells in Science, 244:1081-1085 (1989). Here, a residue or group of target residues within the anti-Ovr110 antibody are identified (e.g., charged residues such as arg, asp, his, lys, and glu) and replaced by a neutral or negatively charged amino acid (most preferably alanine or polyalanine) to affect the interaction of the amino acids with Ovr110 antigen.

Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at a target codon or region and the expressed anti-Ovr110 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-Ovr110 antibody with an N-terminal methionyl residue or the antibody fused to a cytotoxic polypeptide. Other insertional variants of the anti-Ovr110 antibody molecule include the fusion to the N- or C-terminus of the anti-Ovr110 antibody to an enzyme (e.g. for ADEPT) or a fusion to a polypeptide which increases the serum half-life of the antibody.

Another type of variant is an amino acid substitution variant. These variants have at least one amino acid residue in the anti-Ovr110 antibody molecule replaced by a different residue. The sites of greatest interest for substitutional mutagenesis include the hypervariable regions, but FR alterations are also contemplated. Conservative substitutions are shown in Table I under the heading of "preferred substitutions". If such substitutions result in a change in biological activity, then more substantial changes, denominated "exemplary substitutions" in Table 1, or as further described below in reference to amino acid classes, may be introduced and the products screened for a desired characteristic.

TABLE I

Amino Acid Substitutions

| Original | Exemplary Substitutions | Preferred Substitutions |
|---|---|---|
| Ala (A) | val; leu; ile | Val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; | leu |
| Leu (L) | norleucine; ile; val; met; ala; | ile |
| Lys (K) | arg; gln; asn | arg |
| Met (M) | leu; phe; ile | leu |
| Phe (F) | leu; val; ile; ala; tyr | tyr |

TABLE I-continued

Amino Acid Substitutions

| Original | Exemplary Substitutions | Preferred Substitutions |
|---|---|---|
| Pro (P) | ala | ala |
| Ser (S) | thr | thr |
| Thr (T) | ser | ser |
| Trp (W) | tyr; phe | tyr |
| Tyr (Y) | trp; phe; thr; ser | Phe |
| Val (V) | ile; leu; met; phe; ala; | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the anti-Ovr110 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human Ovr110. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-Ovr110 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared nucleic acid molecule encoding a variant or a non-variant version of the anti-Ovr110 antibody.

It may be desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of the antibody.

Screening for Antibodies with the Desired Properties

Techniques for generating antibodies have been described above. One may further select antibodies with certain biological characteristics, as desired.

The growth inhibitory effects of an anti-Ovr110 antibody of the invention may be assessed by methods known in the art, e.g., using cells which express Ovr110 either endogenously or following transfection with the Ovr110 gene. For example, the tumor cell lines and Ovr110-transfected cells provided in Example 1 below may be treated with an anti-Ovr110 monoclonal antibody of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-Ovr110 antibody of the invention. After antibody treatment, the cells are harvested and the amount of radioactivity incorporated into the DNA quantitated in a scintillation counter. Appropriated positive controls include treatment of a selected cell line with a growth inhibitory antibody known to inhibit growth of that cell line. Growth inhibition of tumor cells in vivo can be determined in various ways such as is described in the Experimental Examples section below. Preferably, the tumor cell is one that over-expresses Ovr110. Preferably, the anti-Ovr110 antibody will inhibit cell proliferation of an Ovr110-expressing tumor cell in vitro or in vivo by about 25-100% compared to the untreated tumor cell, more preferably, by about 30-100%, and even more preferably by about 50-100% or 70-100%, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-Ovr110 antibody at about 1 µg/kg to about 100 mg/kg body weight results in reduction in tumor size or tumor cell proliferation within about 5 days to 3 months from the first administration of the antibody, preferably within about 5 to 30 days.

To select for antibodies which induce cell death, loss of membrane integrity as indicated by, e.g., propidium iodide (PI), trypan blue or 7AAD uptake may be assessed relative to a control. A PI uptake assay can be performed in the absence of complement and immune effector cells. Ovr110-expressing tumor cells are incubated with medium alone or medium containing of the appropriate monoclonal antibody at e.g., about 10 µg/ml. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies. Antibodies also modify other cell biological properties relevant to cancer or other immune mechanisms including properties such as cell migration, cell adhesion, cytokine or growth factor secretion.

To screen for antibodies which bind to an epitope on Ovr110 bound by an antibody of interest, e.g., the Ovr110 antibodies of this invention, a routine cross-blocking assay such as that describe in *Antibodies, A Laboratory Manual*, Cold Spring Harbor Laboratory, Ed Harlow and David Lane (1988), can be performed. This assay can be used to determine if a test antibody binds the same site or epitope as an anti-Ovr110 antibody of the invention. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of Ovr110 can be used in competition assays with the test antibodies or with a test antibody and an antibody with a characterized or known epitope.

For example, a method to screen for antibodies that bind to an epitope which is bound by an antibody this invention may comprise combining an Ovr110-containing sample with a test antibody and an antibody of this invention to form a mixture, the level of Ovr110 antibody bound to Ovr110 in the mixture is then determined and compared to the level of Ovr110 antibody bound in the mixture to a control mixture, wherein the level of Ovr110 antibody binding to Ovr110 in the mixture as compared to the control is indicative of the test antibody's binding to an epitope that is bound by the anti-Ovr110 antibody of this invention. The level of Ovr110 antibody bound to Ovr110 is determined by ELISA. The control may be a positive or negative control or both. For example, the control may be a mixture of Ovr110, Ovr110 antibody of this invention and an antibody known to bind the epitope bound by the Ovr110 antibody of this invention. The anti-Ovr110 antibody labeled with a label such as those disclosed herein. The Ovr110 may be bound to a solid support, e.g., a tissue culture plate or to beads, e.g., sepharose beads.

Immunoconjugates

The invention also pertains to therapy with immunoconjugates comprising an antibody conjugated to an anti-cancer agent such as a cytotoxic agent or a growth inhibitory agent.

Chemotherapeutic agents useful in the generation of such immunoconjugates have been described above. Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

Preferably, an anti-Ovr110 antibody (full length or fragments) of the invention is conjugated to one or more maytansinoid molecules.

Maytansinoids are mitototic inhibitors which act by inhibiting tubulin polymerization. Maytansine was first isolated from the cast African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DMI linked to the monoclonal antibody C242 directed against human colorectal cancer. The conjugate was found to be highly cytotoxic towards cultured colon cancer cells, and showed antitumor activity in an in vivo tumor growth assay. Chari et al. Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×10 5 HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-Ovr110 Antibody-Maytansinoid Conjugates (Immunoconjugates)

Anti-Ovr110 antibody-maytansinoid conjugates are prepared by chemically linking an anti-Ovr110 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B 1, and Chari et al. Cancer Research 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred. Conjugates of the antibody and maytansinoid may be made using a variety of bifunctional protein coupling agents such as N-succinimidyl (2-pyridyldithio)propionate (SPDP), succinimidyl-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as his (p-azidobenzoyl)hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). Particularly preferred coupling agents include N-succinimidyl (2-pyridyldithio)propionate (SPDP) (Carlsson et al., Biochem. J. 173:723-737 [1978]) and N-succinimidyl(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. Preferably, the linkage is formed at the C-3 position of maytansinol or a maytansinol analogue.

Calicheamicin

Another immunoconjugate of interest comprises an anti-Ovr110 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company).

Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$, (Hinman et al. Cancer Research 53: 3336 (1993), Lode et al. Cancer Research 5 8: 2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-Ovr110 antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). Enzymatically active toxins and fragments thereof which can be used include diphtheria A chain, 1 5 nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993. The present invention further contemplates an immunoconjugate formed between an antibody and a compound with nucleolytic activity (e.g. a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-Ovr110 antibodies. Examples include $At^{211}$, $I^{131}$, $I^{125}$, $In^{111}$, $Y^{90}$, $Re^{186}$, $Re^{188}$, $Sm^{153}$, $Bi^{212}$, $P^{32}$, and radioactive isotopes of Lu. When the conjugate is used for diagnosis, it may comprise a radioactive atom for scintigraphic studies, for example $Tc^{99m}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $Tc^{99M}$, $I^{123}$, $In^{111}$, $Re^{186}$, $Re^{188}$, can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl (2-pyridyldithio)propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon labeled 1-isothiocyanatobenzyl methyldiethylene triaminepentaacetic acid (MX-DTPA) is an exemplary chelating agent for conjugation of radionucleotide to the antibody. See WO 94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al. Cancer Research 52: 127-131 (1992); U.S. Pat. No. 5,208, 020) may be used.

Alternatively, a fusion protein comprising the anti-Ovr110 antibody and cytotoxic agent may be made, e.g. by recombinant techniques or peptide synthesis. The length of DNA may comprise respective regions encoding the two portions of the conjugate either adjacent one another or separated by a region encoding a linker peptide which does not destroy the desired properties of the conjugate.

In addition, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145, the disclosure of which is hereby expressly incorporated by reference) to an active anti-cancer drug. See, for example, WO 88/07378 and U.S. Pat. No. 4,975,278, the disclosures of which are hereby expressly incorporated by reference.

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as O-galactosidase and neuraminidase useful for converting glycosylated prodrugs into free drugs; P-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population. The enzymes of this invention can be covalently bound to the anti-Ovr110 antibodies by techniques well known in the art such as the use of the heterobifunctional crosslinking reagents discussed above.

Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The anti-Ovr110 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); U.S. Pat. Nos. 4,485,045 and 4,544,545; and WO97/38731 published Oct. 23, 1997, the disclosures of which are hereby expressly incorporated by reference. Liposomes with enhanced circulation time are disclosed in U.S. Pat. No. 5,013,556, the disclosure of which is hereby expressly incorporated by reference. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81(19)1484 (1989).

Vectors, Host Cells, and Recombinant Methods

The invention also provides isolated nucleic acid molecule encoding the humanized anti-Ovr110 antibody, vectors and host cells comprising the nucleic acid, and recombinant techniques for the production of the antibody. For recombinant production of the antibody, the nucleic acid molecule encoding it is isolated and inserted into a replicable vector for further cloning (amplification of the DNA) or inserted into a vector in operable linkage with a promoter for expression. DNA encoding the monoclonal antibody is readily isolated and sequenced using conventional procedures (e.g., by using oligonucleotide probes that are capable of binding specifically to nucleic acid molecules encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Signal Sequence Component

The anti-Ovr110 antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native anti-Ovr110 antibody signal sequence, the signal sequence is substituted by a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, oc factor leader (including Saccharomyces and Kluyveromyces cc-factor leaders), or acid phosphatase leader, the C. albicans glucoamylase leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the anti-Ovr110 antibody.

Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-Ovr110 antibody nucleic acid, such as DHFR, thymidine kinase, metallothionein-I and -11, preferably primate metallothionein genes, adenosine deaminase, ornithine decarboxylase, etc. For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding anti-Ovr110 antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4 Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 pm circular plasmid pKDI can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., Bio/Technology, 9:968-975 (1991).

Promoter Component

Expression and cloning vectors usually contain a promoter that is recognized by the host organism and is operably linked to the anti-Ovr110 antibody nucleic acid. Promoters suitable for use with prokaryotic hosts include the phoA promoter, P-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-Ovr110 antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors. Examples of suitable promoter sequences for use with yeast hosts include the promoters for 3-phosphoglycerate kinase or other glycolytic enzymes, such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-Ovr110 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human P-interferon cDNA in mouse cells under the control of a thymidine kinase promoter from herpes simplex virus. Alternatively, the Rous Sarcoma Virus long terminal repeat can be used as the promoter.

Enhancer Element Component

Transcription of a DNA encoding the anti-Ovr110 antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the anti-Ovr110 antibody-encoding sequence, but is preferably located at a site 5' from the promoter.

Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding anti-Ovr110 antibody. One useful transcription termination component is the bovine growth hormone polyadenylation region. See WO 94/11026 and the expression vector disclosed therein.

Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W31 10 (ATCC 27,325) are suitable. These examples are illustrative rather than limiting.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-Ovr110 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-Ovr110 antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, *Arabidopsis* and tobacco can also be utilized as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, 1413 8065); mouse mammary tumor (MMT 060562, ATCC CCL5 1); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-Ovr110 antibody production and cultured in conventional nutrient media modified as appropriate for inducing promoters, selecting transformants, or amplifying the genes encoding the desired sequences.

Culturing Host Cells

The host cells used to produce the anti-Ovr110 antibody of this invention may be cultured in a variety of media. Commercially available media such as Ham's FIO (Sigma), Minimal Essential Medium (MEM)(Sigma), RPMI-1640 (Sigma), and Dulbecco's Modified Eagle's Medium (DMEM)(Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Anti-Ovr110 Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SIDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Pharmaceutical formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol, and mcresol); low molecular weight (less than about 10 residues) polypeptides; proteins, such as serum albumin, gelatin, or immunoglobulins; hydrophilic polymers such as polyvinylpyllolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). The antibody preferably comprises the antibody at a concentration of between 5-200 mg/ml, preferably between 10-100 mg/ml.

The formulation herein may also contain more than one active compound as necessary for the particular indication being treated, preferably those with complementary activities that do not adversely affect each other. For example, in addition to the anti-Ovr110 antibody which internalizes, it may be desirable to include in the one formulation, an additional antibody, e.g. a second anti-Ovr110 antibody which binds a different epitope on Ovr110, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–) hydroxybutyric acid.

The formulations to be used for in vivo administration must be sterile. This is readily accomplished by filtration through sterile filtration membranes.

Methods and Treatment Using Anti-Ovr110 Antibodies

According to the present invention, the anti-Ovr110 antibody that modulates Ovr110 activity upon binding Ovr110 or internalize upon binding Ovr110 on a cell surface is used to treat a subject in need thereof having a cancer characterized by Ovr110-expressing cancer cells, in particular, ovarian, endometrial, head & neck, kidney, pancreatic, lung or breast cancer, such as ovarian serous adenocarcinoma or breast infiltrating ductal carcinoma cancer, and associated metastases.

The cancer will generally comprise Ovr110-expressing cells, such that the anti-Ovr110 antibody is able to bind thereto. While the cancer may be characterized by overexpression of the Ovr110 molecule, the present application further provides a method for treating cancer which is not considered to be an Ovr110-overexpressing cancer.

This invention also relates to methods for detecting cells which overexpress Ovr110 and to diagnostic kits useful in detecting cells expressing Ovr110 or in detecting Ovr110 in serum from a patient. The methods may comprise combining a cell-containing test sample with an antibody of this invention, assaying the test sample for antibody binding to cells in the test sample and comparing the level of antibody binding in the test sample to the level of antibody binding in a control sample of cells. A suitable control is, e.g., a sample of normal cells of the same type as the test sample or a cell sample known to be free of Ovr110 overexpressing cells. A level of Ovr110 binding higher than that of such a control sample would be indicative of the test sample containing cells that overexpress Ovr110. Alternatively the control may be a sample of cells known to contain cells that overexpress Ovr110. In such a case, a level of Ovr110 antibody binding in the test sample that is similar to, or in excess of, that of the control sample would be indicative of the test sample containing cells that overexpress Ovr110.

Ovr110 overexpression may be detected with a various diagnostic assays. For example, over expression of Ovr110 may be assayed by immunohistochemistry (IHC). Parrafin embedded tissue sections from a tumor biopsy may be subjected to the IHC assay and accorded an Ovr110 protein staining intensity criteria as follows.

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for Ovr110 expression may be characterized as not overexpressing Ovr110, whereas those tumors with 2+ or 3+ scores may be characterized as overexpressing Ovr110.

Alternatively, or additionally, FISH assays such as the INFORM™ (sold by Ventana, Arizona) or PATHVISION™ (VySiS, Illinois) may be carried out on formalin-fixed, paraffin-embedded tumor tissue to determine the extent (if any) of Ovr110 overexpression in the tumor. Ovr110 overexpression or amplification may be evaluated using an in vivo diagnostic assay, e.g. by administering a molecule (such as an antibody of this invention) which binds Ovr110 and which is labeled with a detectable label (e.g. a radioactive isotope or a fluorescent label) and externally scanning the patient for localization of the label.

A sample suspected of containing cells expressing or overexpressing Ovr110 is combined with the antibodies of this invention under conditions suitable for the specific binding of the antibodies to Ovr110. Binding and/or internalizing the Ovr110 antibodies of this invention is indicative of the cells expressing Ovr110. The level of binding may be determined and compared to a suitable control, wherein an elevated level of bound Ovr110 as compared to the control is indicative of Ovr110 overexpression. The sample suspected of containing cells overexpressing Ovr110 may be a cancer cell sample, particularly a sample of an ovarian cancer, e.g. ovarian serous adenocarcinoma, or a breast cancer, e.g., a breast infiltrating ductal carcinoma. A serum sample from a subject may also be assayed for levels of Ovr110 by combining a serum sample from a subject with an Ovr110 antibody of this invention, determining the level of Ovr110 bound to the antibody and comparing the level to a control, wherein an elevated level of Ovr110 in the serum of the patient as compared to a control is indicative of overexpression of Ovr110 by cells in the patient. The subject may have a cancer such as e.g., an ovarian cancer, e.g. ovarian serous adenocarcinoma, or a breast cancer, e.g., a breast infiltrating ductal carcinoma.

Currently, depending on the stage of the cancer, ovarian, pancreatic, lung or breast cancer treatment involves one or a combination of the following therapies: surgery to remove the cancerous tissue, radiation therapy, androgen deprivation (e.g., hormonal therapy), and chemotherapy. Anti-Ovr110 antibody therapy may be especially desirable in elderly patients who do not tolerate the toxicity and side effects of chemotherapy well, in metastatic disease where radiation or chemotherapy have limited usefulness. The tumor targeting and internalizing anti-Ovr110 antibodies of the invention are useful to alleviate Ovr110-expressing cancers, e.g., ovarian, pancreatic, endometrial, head & neck, kidney, lung or breast cancers upon initial diagnosis of the disease or during relapse.

For therapeutic applications, the anti-Ovr110 antibody can be used alone, or in combination therapy with, e.g., other antibodies, chemotherapeutics, hormones, antiangiogens, or radiolabelled compounds, or with surgery, cryotherapy, and/or radiotherapy, notably for ovarian, pancreatic, endometrial, head & neck, kidney, lung or breast cancers, also particularly where shed cells cannot be reached. Anti-Ovr110 antibody treatment can be administered in conjunction with other forms of conventional therapy, either consecutively with, pre- or post-conventional therapy, Chemotherapeutic drugs such as Taxotere® (docetaxel), Taxol® (paclitaxel), estramustine and mitoxantrone are used in treating metastatic and hormone refractory ovarian, pancreatic, lung or breast cancer, in particular, in good risk patients. In the present method of the invention for treating or alleviating cancer, in particular, androgen independent and/or metastatic ovarian, pancreatic, lung or breast cancer, the cancer patient can be administered anti-Ovr110 antibody in conjunction with treatment with the one or more of the preceding chemotherapeutic agents. In particular, combination therapy with paclitaxel and modified derivatives (see, e.g., EP0600517) is contemplated. The anti-Ovr110 antibody will be administered with a therapeutically effective dose of the chemotherapeutic agent. The anti-Ovr110 antibody may also be administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

Particularly, an immunoconjugate comprising the anti-Ovr110 antibody conjugated with a cytotoxic agent may be administered to the patient. Preferably, the immunoconjugate bound to the Ovr110 protein is internalized by the cell, resulting in increased therapeutic efficacy of the immunoconjugate in killing the cancer cell to which it binds. Preferably, the cytotoxic agent targets or interferes with the nucleic acid in the cancer cell. Examples of such cytotoxic agents are described above and include maytansin, maytansinoids, saporin, gelonin, ricin, calicheamicin, ribonucleases and DNA endonucleases.

The anti-Ovr110 antibodies or immunoconjugates are administered to a human patient, in accord with known methods, such as intravenous administration, e.g., as a bolus or by continuous infusion over a period of time, by intramuscular, intraperitoneal, intracerebrospinal, subcutaneous, intra-articular, intrasynovial, intrathecal, oral, topical, or inhalation routes. The antibodies or immunoconjugates may be injected directly into the tumor mass. Intravenous or subcutaneous administration of the antibody is preferred. Other therapeutic regimens may be combined with the administration of the anti-Ovr110 antibody.

The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-Ovr110 antibody or antibodies, with administration of an antibody directed against another tumor antigen associated with the particular cancer. As such, this invention is also directed to an antibody "cocktail" comprising one or more antibodies of this invention and at least one other antibody which binds another tumor antigen associated with the Ovr110-expressing tumor cells. The cocktail may also comprise antibodies that are directed to other epitopes of Ovr110. Preferably the other antibodies do not interfere with the binding and or internalization of the antibodies of this invention.

The antibody therapeutic treatment method of the present invention may involve the combined administration of an anti-Ovr110 antibody (or antibodies) and one or more chemotherapeutic agents or growth inhibitory agents, including co-administration of cocktails of different chemotherapeutic agents. Chemotherapeutic agents include, e.g., estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is an estrogen independent cancer, the patient may previously have been subjected to anti-estrogen therapy and, after the cancer becomes estrogen independent, the anti-Ovr110 antibody (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody therapy. Suitable dosages for any of the above co-administered agents are those presently used and may be lowered due to the combined action (synergy) of the agent and anti-Ovr110 antibody.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 pg/kg to about 50 mg/kg body weight (e.g. about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-Ovr110 antibody. However, other dosage regimens may be useful. A typical daily dosage might range from about 1 pg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of a nucleic acid molecule encoding the antibody is encompassed by the expression "administering a therapeutically effective amount of an antibody". See, for example, WO 96/07321 published Mar. 14, 1996 (the disclosure of which is hereby expressly incorporated by reference) concerning the use of gene therapy to generate intracellular antibodies.

There are two major approaches to introducing the nucleic acid molecule (optionally contained in a vector) into the patient's cells; in vivo and ex vivo. For in vivo delivery the nucleic acid molecule is injected directly into the patient, usually at the site where the antibody is required. For ex vivo treatment, the patient's cells are removed, the nucleic acid molecule is introduced into these isolated cells and the modified cells are administered to the patient either directly or, for example, encapsulated within porous membranes which are implanted into the patient (see, e.g. U.S. Pat. Nos. 4,892,538 and 5,283,187, the disclosures of which are hereby expressly incorporated by reference). There are a variety of techniques available for introducing nucleic acid molecules into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid molecule transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et at., Science 256:808-813 (1992). See also WO 93/25673 and the references cited therein.

Articles of Manufacture and Kits

The invention also relates to an article of manufacture containing materials useful for the detection for Ovr110 over-expressing cells and/or the treatment of Ovr110 expressing cancer, in particular ovarian, pancreatic, lung or breast cancer. The article of manufacture comprises a container and a composition contained therein comprising an antibody of this invention. The composition may further comprise a carrier. The article of manufacture may also comprise a label or package insert on or associated with the container. Suitable containers include, for example, bottles, vials, syringes, etc. The containers may be formed from a variety of materials such as glass or plastic. The container holds a composition which is effective for detecting Ovr110 expressing cells and/or treating a cancer condition and may have a sterile access port (for example the container may be an intravenous solution bag or a vial having a stopper pierceable by a hypodermic injection needle). At least one active agent in the composition is an anti-Ovr110 antibody of the invention. The label or package insert indicates that the composition is used for detecting Ovr110 expressing cells and/or for treating ovarian, pancreatic, lung or breast cancer, or more specifically ovarian serous adenocarcinoma or breast infiltrating ductal carcinoma cancer, in a patient in need thereof. The label or package insert may further comprise instructions for administering the antibody composition to a cancer patient. Additionally, the article of manufacture may further comprise a second container comprising a substance which detects the antibody of this invention, e.g., a second antibody which binds to the antibodies of this invention. The substance may be labeled with a detectable label such as those disclosed herein. The second container may contain e.g., a pharmaceutically-acceptable buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

Kits are also provided that are useful for various purposes, e.g., for Ovr110 cell killing assays, for purification or immunoprecipitation of Ovr110 from cells or for detecting the presence of Ovr110 in a serum sample or detecting the presence of Ovr110-expressing cells in a cell sample. For isolation and purification of Ovr110, the kit can contain an anti-Ovr110 antibody coupled to a solid support, e.g., a tissue culture plate or beads (e.g., sepharose beads). Kits can be provided which contain the antibodies for detection and quantitation of Ovr110 in vitro, e.g. in an ELISA or a Western blot. As with the article of manufacture, the kit comprises a container and a composition contained therein comprising an antibody of this invention. The kit may further comprise a label or package insert on or associated with the container. The kits may comprise additional components, e.g., diluents and buffers, substances which bind to the antibodies of this invention, e.g., a second antibody which may comprise a label such as those disclosed herein, e.g., a radiolabel, fluorescent label, or enzyme, or the kit may also comprise control antibodies. The additional components may be within separate containers within the kit. The label or package insert may will be referred to as Q3.2, etc. For the purposes of this invention, a reference to Ovr110.Q3 or Q3 will include all clones, e.g., Q3.1, Q3.2, etc.

Immunogens and Antigens

For antibody production, screening and characterization various recombinant proteins, membrane preparations and transfected cells were prepared as described below.

For the Ovr110 constructs described below, nucleic acid molecules encoding regions of Ovr110 were inserted into various expression vectors to produce recombinant proteins. These nucleic acid sequences were isolated using primers, the design of which is routine to one of skill in the art. In some cases, the primers used are included in the descriptions below of each construct.

For purposes of illustration, the predicted amino acid sequence encoded by each construct is also included. However, the constructs may include naturally occurring variants (e.g. allelic variants, SNPs) within the Ovr110 region as isolated by the primers. These variant sequences, and antibodies which bind to them are considered part of the invention as described herein.

Ovr110 Construct1 (His-Tagged)

A nucleic acid molecule encoding the full length Ovr110 protein, amino acids Met1 to Lys282, was inserted into a modified vector comprising a sequence at the 3' end of the cloning site encoding two transitional amino acids, Ala and Ser, and a 6 His tag. The resulting vector with the inserted Ovr110 nucleic acid fragment encodes a recombinant Ovr110 fusion protein with the 6 His-tag fused to the C-terminus of the Ovr110 protein. This recombinant plasmid encoding the full length Ovr110 His-tagged protein is herein referred to as "Ovr110 Construct 1". A representative amino acid sequence encoded by Ovr110 Construct 1 is presented in SEQ ID NO:51.

```
Ovr110 Construct 1 Amino Acid Sequence
                                                    (SEQ ID NO: 51)
MASLGQILFWSIISIIIILAGAIALIIGFGISGRHSITVTTVASAGNIGEDGILSCTFEPDIKLSDIVIQ

WLKEGVLGLVHEFKEGKDELSEQDEMFRGRTAVFADQVIVGNASLRLKNVQLTDAGTYKCYIITSKGKGN

ANLEYKTGAFSMPEVNVDYNASSETLRCEAPRWFPQPTVVWASQVDQGANFSEVSNTSFELNSENVTMKV

VSVLYNVTINNTYSCMIENDIAKATGDIKVTESEIKRRSHLQLLNSKASLCVSSFFAISWALLPLSPYLM

LKASHHHHHH
``` provide a description of the composition as well as instructions for the intended in vitro or diagnostic use.

EXAMPLES

Example 1

Production and Isolation of Monoclonal Antibody Producing Hybridomas

The following MAb/hybridomas of the present invention are described below: Ovr110.Q1, Ovr110.Q3, Ovr110.Q4, Ovr110.Q5, Ovr110.Q6, Ovr110.Q7, Ovr110.Q8, Ovr110.Q9, Ovr110.Q10, Ovr110.Q11, Ovr110.Q12, Ovr110.Q13, Ovr110.Q14, Ovr110.Q15, Ovr110.Q16, Ovr110.Q17, Ovr110.Q18, Ovr110.Q19, Ovr110.Q20, Ovr110.Q21, Ovr110.Q22, Ovr110.Q23, Ovr110.Q24, Ovr110.Q25, Ovr110.Q26, Ovr110.Q27. If the MAb has been cloned, it will get the nomenclature "X.1," e.g., the first clone of Ovr110.Q3 will be referred to as Q3.1, the second clone of Q3

The Ovr110 protein expressed by Construct 1 was column purified using standard techniques from cell culture of 293F cells transfected with Construct 1. Samples from collected fractions were subjected to SDS-PAGE and Western blot analysis for assessing the purity of the protein.

Ovr110-hFc (with TM)

A nucleic acid molecule encoding the mature Ovr110 protein, amino acids Gly30 to Lys282, was inserted into a modified vector comprising a sequence at the 5' end of the cloning site encoding an amino acid secretion signal sequence from human stanniocalcin 1 (STC) and a sequence at the 3' end of the cloning site encoding two transitional amino acids, Ala and Ser, and human Fc region (hFc). The resulting vector with the inserted Ovr110 nucleic acid fragment encodes a recombinant Ovr110 fusion protein with an N-terminal STC secretion signal and a hFc fused to the C-terminus of the Ovr110 protein. This recombinant plasmid encoding the mature Ovr110-hFc protein is herein referred to as "Ovr110 Construct 2". A representative amino acid sequence encoded by Ovr110 Construct 2 is presented in SEQ ID NO:52.

Ovr110 Construct 2 Amino Acid Sequence
(SEQ ID NO: 52)

MLQNSAVLLVLVISASADIGISGRHSITVTTVASAGNIGEDGILSCTFEPDIKLSDIVIQWLKEGVLGLVHE

FKEGKDELSEQDEMFRGRTAVFADQVIVGNASLRLKNVQLTDAGTYKCYIITSKGKGNANLEYKTGAFSMPE

VNVDYNASSETLRCEAPRWFPQPTVVWASQVDQGANFSEVSNTSFELNSENVTMKVVSVLYNVTINNTYSCM

IENDIAKATGDIKVTESEIKRRSHLQLLNSKASLCVSSFFAISWALLPLSPYLMLKASTCPPCPAPELLGGP

SVFLFPPKPKDTLMISRTPEVTCVVVDVSHEDPEVKFNWYVDGVEVHNAKTKPREEQFNSTFRVVSVLTVLH

QDWLNGKEYKCKVSNKALPAPIEKTISKTKGQPREPQVYTLPPSREEMTKNQVSLTCLVKGFYPSDIAVEWE

SSGQPENNYNTTPPMLDSDGSFFLYSKLTVDKSRWQQGNVFSCSVMHEALHNHYTQKSLSLSPGK

The Ovr110 protein expressed by Construct 2 was column purified using standard techniques from cell culture of 293F cells transfected with Construct 2. Samples from collected fractions were subjected to SDS-PAGE and Western blot analysis for assessing the purity of the protein.

293F Transiently Transfected with Ovr110

Cells from the 293F cell line from Invitrogen (Carlsbad, Calif.) were transiently transfected to express Ovr110. A nucleic acid molecule encoding amino acids 1-282 of Ovr110 (Ovr110 Construct 1 without the 6-His tag) was cloned into the mammalian expression vector, PCDNA3.1, and the recombinant vector was used to transfect human 293F cells (Invitrogen). Fifty ml of 293F cells cultured in freestyle medium (Invitrogen) at $10^6$ cells/ml were transfected using 293fectin transfection reagent (Invitrogen), according to the manufacturer's guidelines. DNA, cells and 293fectin were mixed in OPTI-MEM medium (GIBCO). Cells were used for analysis 48 h after transfection. 293F cells expressing Ovr110 are referred to herein as 293F-Ovr110 cells.

CHO Stably Transfected with Ovr110

Hamster CHO cells were stably transfected with the PCDN5/FRT/TO vector to make CHO-FlpIn stable cell lines by following the Invitrogen protocol. CHO-FlpIn cells were cultured in HamsF12 medium with 10% fetal bovine serum (FBS). Ovr110 (Ovr110 Construct 1 without the 6-His tag) was co-transfected with p0044 Flp recombinase into CHO-FlpIn with 2 ug of Ovr110 DNA, 18 ug of POG44 DNA and Lipofectamine 2000 in a 6 well plate as described in the Invitrogen protocol. Stable transfectant selection was performed in HamsF12 medium+10% FBS with Hygromycin B at 300 ug/ml, for 10-15 days after transfection.

Hygromycin B-resistant cells were checked for expression of Ovr110 protein by Western Blot using an anti-Ovr110 monoclonal antibody. Cells which demonstrated Ovr110 expression were expanded, scaled-up, cryopreserved in FBS with 10% DMSO and stored in Liquid Nitrogen at −196° C. to assure maintenance of viable clone cultures (12-15 clones of each).

RK3E Stably Transfected with Ovr110

RK3E cells stably expressing Ovr110 were generated using the *Phoenix* Retrovirus Expression System (Orbigen, San Diego, Calif.). A nucleic acid molecule encoding amino acids 1-282 of Ovr110 (Ovr110 Construct 1 without the 6-His tag) inserted into retroviral vector PLXSN (pLAPSN, BD Biosciences Clontech, Palo Alto, Calif.) was transfected into *Phoenix*-Eco packaging cells. Two days later, the culture media were harvested and filtered through 0.45 um polysulfonic filter. RK3E cells were split at $5 \times 10^5$ cells on 10 cm plates the day before the infection. 8 ug/ml polybrene (Sigma-Aldrich, St. Louis, Mo.) was added to the virus-containing media prior to their addition to the target cells. 7 hours later, the virus media was replaced with fresh growth medium. Stably-infected cells were selected with 0.5 mg/ml G418. RK3E cells stably expressing Ovr110 are referred to herein as RK3E-Ovr110 cells.

Membrane Prep from CHO-Ovr110

For cell membrane preps 760 million CHO cells expressing Ovr110 (described above) were suspended in 20 mL of iced hypotonic buffer (10 mM tris-HCl pH 7.4, 1 mM EDTA, 3 mM MgCl2, 1 mM EGTA, with protease inhibition). The sample was homogenized with 30 strokes in a 25 mL Bellco Dounce with loose pestle (A) and left on ice for 15-20 minutes. The sample was spun at 200 rpm for 5 minutes at 4 degrees C. in a GS6KR Beckman centrifuge. The supernatant was homogenized with 30 strokes in a 25 mL Bellco Dounce with tight pestle (B) and left on ice for 15-20 minutes. The sample was spun 20,000 rpm for 1 hour at 4 degrees C. in a GS6KR Beckman centrifuge. The pellet contained the membrane fraction and was resuspended in 2 mL PBS prior to content confirmation by western blot analysis.

Immunizations

Mice were immunized with membrane preparations of CHO cells stably transfected with Ovr110 to generate anti-Ovr110 MAbs capable of binding to Ovr110 in bodily fluids and on a cell surface. Eight BALB/c mice were immunized twice weekly for five weeks Immunizations were done intradermally in both rear footpads with 10 ug CHO-Ovr110 membranes in 25 uL PBS per foot.

Hybridoma Fusion

Four days after the final immunization, mice were sacrificed and draining lymph node (popliteal) tissue was collected by sterile dissection. Lymph node cells were dispersed using a Tenbroeck tissue grinder (Wheaton #347426, VWR, Brisbane, Calif.) followed by pressing through a sterile sieve (VWR) into DMEM and removing T-cells via anti-CD90 (Thy1.2) coated magnetic beads (Miltenyi Biotech, Bergisch-Gladbach, Germany).

These primary B-cell enriched lymph node cells were then immortalized by electro-cell fusion (BTX, San Diego, Calif.) with the continuous myeloma cell line P3x63Ag8.653 (Kearney, J. F. et al., J. Immunology 123: 1548-1550, 1979). The myeloma and B-cells were pooled at a 1:1 ratio for the fusion. These fusion cultures were distributed at 2 million cells per plate into wells of 96 well culture plates (Costar #3585, VWR). Successfully fused cells were selected by culturing in selection medium (DMEM/15% FBS) containing 2.85 µM Azaserine, 50 µM Hypoxanthine (HA) (Sigma) or 50 µM Hypoxanthine, 0.2 µM Aminopterin, 8 µM Thymidine (HAT) (Sigma) supplemented with recombinant human IL-6 (Sigma) at 0.5 ng/mL. Cultures were transitioned into medium (DMEM/10% FBS) without selection and IL-6 supplements for continued expansion and antibody production.

Supernatants from wells were screened by enzyme linked solid phase immunoassay (ELISA), flow cytometry and antibody internalization for reactivity against Ovr110. Monoclonal cultures, consisting of the genetically uniform progeny from single cells, were established after the screening procedure, by sorting of single viable cells into wells of two 96 well plates, using flow cytometry (Coulter Elite; Beckman-Coulter, Miami, Fla.). The resulting murine B-cell hybridoma cultures were expanded using standard tissue culture techniques. Selected hybridomas were cryopreserved in fetal bovine serum (FBS) with 10% DMSO and stored in Liquid Nitrogen at −196° C. to assure maintenance of viable clone cultures.

ELISA Screening & Selection of Hybridomas Producing Ovr110 Specific Antibodies

Hybridoma cell lines were selected for production of Ovr110-specific antibody by sandwich ELISA and cell ELISA.

Sandwich ELISA

Goat antiserum specific to human IgG Fc and minimal cross-reactivity to mouse Fc (2 ug/mL in PBS; 100 uL/well; Jackson Immunoresearch P/N 109-005-098, West Grove, Pa.) was nonspecifically adsorbed to the surface of the EIA plates by incubating overnight at 4° C. The plate wells were emptied and nonspecific binding capacity was blocked by filling the wells (300 uL/well) with TBST/0.5% bovine serum albumin (TBST/BSA) and incubating for >30 minutes at room temperature (RT). Wells were emptied and filled with 100 uL recombinant Ovr110-hFc (encoded by Ovr110 Construct 2) at 1 ug/mL in TBST/BSA (described above). After incubation of >1 hr, the wells were emptied and filled with 50 uL/well TBST/BSA. Hybridoma culture medium sample was added to the wells (50 uL) and incubated for 1 hour. The wells were washed 3 times with TBST. One hundred uL of alkaline phosphatase conjugated goat anti-mouse IgG (Fc) with minimal cross-reactivity to human Fc (P/N115-055-071, Jackson Immunoresearch), diluted 1:5000 in TBST/BSA, was added to each well and incubated for >1 hour. The wells were washed 3 times with TBST. One hundred uL of alkaline phosphatase substrate para-nitrophenylphosphate (pNPP) (Sigma) at 1 mg/mL in 1 M Diethanolamine buffer pH 8.9 (Pierce) was added to each well and incubated for 20 min. The enzymatic reaction was quantified by measuring the solution's absorbance at 405 nm wavelength. Hybridoma supernatants that produced an absorbance value of greater than 0.50 were considered Ovr110-specific.

Cell ELISA

For the Cell ELISA, the binding of antibodies to RK3E cells stably transduced with either Ovr110 (RK3E-Ovr110) or alkaline phosphatase (RK3E-AP; negative control) was evaluated. 25,000 cells in 100 uL growth medium were plated per well of a 96-well plate coated with Poly-D-Lysine (#15600, Pierce). Cells were incubated overnight, and 50 ul hybridoma supernatant was added to each well. Cells were incubated on ice for 30 min. Wells were emptied and washed with TBST/BSA. Cells were then fixed for 10 min on ice by adding 100 uL 4% formaldehyde in TBS. Wells were emptied and washed with TBST/BSA. 300 uL TBST/BSA was added to each well. After incubating cells for 30 min, wells were emptied and washed twice with TBST/BSA. 100 uL biotin-conjugated rabbit (Fab2) anti-mouse IgG (PN315-066-046; Jackson Immunoresearch, West Grove, Pa.), diluted 1:20,000 in TBST/BSA, were added per well to stain the cells. After 30 min incubation, wells were emptied and washed twice with TBST/BSA. 100 uL Streptavidin-HRP conjugate (#21126; Pierce), diluted 1:20,000 in TBST/BSA, were added to each well and cells were incubated for 30 min. Wells were washed twice with TBST/BSA. 100 uL of HRP substrate 3,3',5,5'-tetramethyl benzidine (#S1599; Dako Cytomation, Carpinteria, Calif.) were added. The reaction was stopped by adding 100 ul 1N hydrochloric acid, usually after 20 min. The enzymatic reaction was quantified by measuring the solution's absorbance at 450 nm wavelength. Hybridoma supernatants that produced a ratio of OD values from RK3E-Ovr110 to RK3E-AP of >1.5 were considered Ovr110-specific.

Hybridomas secreting Ovr110-specific antibody were designated Q1, Q3, Q4, Q5, Q6, Q7, Q8, Q9, Q10, Q11, Q12, Q13, Q14, Q15, Q16, Q17, Q18, Q19, Q20, Q21, Q23, Q24, Q25, Q26, and Q27.

Flow Cytometry Screening for Cell Surface Binding of Ovr110 Antibodies

Selected hybridoma supernatants were analyzed by flow cytometry for cell surface staining of Ovr110-transfected 293F cells and tumor cell lines. The following tumor cell lines were used: SKBR3, ZR-75-1 and HeLa. SKBR3 and ZR75-1 cells express Ovr110 RNA as determined by QPCR and Ovr110 protein as determined by Western Blot. HeLa cells do not express Ovr110 RNA or protein.

293F cells were transiently transfected with the Ovr110 (described above) using 293fectin (Invitrogen) as transfection reagent. 48 hours post-transfection, cells were washed once with 10 ml $Ca^{+2}/Mg^{+2}$ free DPBS and then 7 ml of warm (37° C.) Cellstripper (Mediatech, Herndon, Va.) was added per 150 $cm^2$ flask. The cells were then incubated for 5 minutes at 37° C. with tapping of the flask to remove tightly attached cells. The cells were removed and pipetted several times to break aggregates, then immediately placed in DMEM/10% FBS/5 mM sodium butyrate. The cells were then centrifuged down for 5 minutes at 1300 rpm and resuspended in DMEM/10% FBS/5 mM sodium butyrate. The cells were incubated at 37° C. for a 30 min. recovery period. Prior to staining, viability of the cells was measured using Guava Viacount (Guava Cytometers, Foster City, Calif.) and cultures with >90% viability were selected for staining with MAbs.

Cells from cultures selected for MAb staining were aliquoted at $0.5-1.0 \times 10^6$ cells/well in 96-well v-bottom plates (VWR) and centrifuged for 2 minutes at 1500 rpm. Supernatants were aspirated and plates briefly shaken on a vortex mixer to resuspend the cells, then 200 uL of DPBS/3% FBS/0.01% Na Azide (FACS buffer) was added to each well. Centrifugation and aspiration was repeated, then 25 uL of sequential dilutions of hybridoma supernatant or purified MAb was added to the cells. Plates were stored on ice for 15 min., then washed and centrifuged as above, in 200 uL of FACS buffer. This washing procedure was repeated twice and then 25 uL of phycoerythrin (PE) conjugated donkey anti-mouse IgG Fc antibody (Jackson Immunoresearch Laboratories) were added to cells. After 15 minutes on ice the cells were washed twice, as above and then resuspended in 250 uL of FACS buffer for analysis on the cell sorter or flow cytometer. In certain cases, for storage overnight at 4° C. prior to analysis, 133 uL of FACS buffer and 67 uL of 1% paraformaldehyde/DPBS was added to each well, for fixation, then the volume was increased to 250 uL with DPBS. Stained cells were analyzed on an Elite fluorescent activated cell sorter (FACS) (Beckman-Coulter).

Most hybridoma supernatants reacted strongly with Ovr110-transfected 293F cells and Ovr110-positive tumor cells, and showed no or weak binding to Ovr110-negative cells. Antibodies to ricin which does not localize to the cell surface and CD71 which localizes to the cell surface served as negative and positive controls, respectively. Results of the cell surface staining are shown in tables 1 and 2.

TABLE 1

Cell surface staining of Ovr110 expressing cells with hybridoma supernatants

| Sample | Ovr110-Transfected 293F Cells | | Untransfected 293F Cells | |
|---|---|---|---|---|
| | % Cells Positive | Mean Fluorescence Intensity (MFI) | % Cells Positive | Mean Fluorescence Intensity (MFI) |
| Anti-Ricin | 1.6 | 0.297 | 0.9 | 0.278 |
| Anti-CD71 | 97.9 | 9.15 | 95 | 4.21 |
| Ovr110.Q1 | 96.2 | 23.3 | 1.1 | 0.29 |
| Ovr110.Q3 | 95.3 | 13.6 | 1 | 0.287 |
| Ovr110.Q4 | 89.8 | 8.32 | 1.7 | 0.311 |
| Ovr110.Q5 | 84.6 | 4.89 | 0.8 | 0.273 |
| Ovr110.Q6 | 97.4 | 7.12 | 71.1 | 1.27 |
| Ovr110.Q7 | 27 | 1.02 | | |
| Ovr110.Q8 | 2.5 | 0.331 | | |
| Ovr110.Q9 | 84.3 | 1.96 | 83.5 | 1.72 |
| Ovr110.Q10 | 1.8 | 0.317 | | |
| Ovr110.Q11 | 95.7 | 26 | 0.7 | 0.282 |
| Ovr110.Q12 | 96.6 | 31.8 | 0.8 | 0.29 |
| Ovr110.Q13 | 2.1 | 0.316 | | |
| Ovr110.Q14 | 97 | 28.2 | 1.6 | 0.326 |
| Ovr110.Q15 | 97.3 | 32.9 | 0.8 | 0.277 |
| Ovr110.Q16 | 22.2 | 0.49 | | |
| Ovr110.Q17 | 97.5 | 30.5 | 0.8 | 0.296 |
| Ovr110.Q18 | 3.9 | 0.341 | | |
| Ovr110.Q19 | 95.7 | 24.5 | 1.2 | 0.309 |
| Ovr110.Q20 | 99.8 | 12.9 | 1.2 | 0.293 |
| Ovr110.Q21 | 18.7 | 0.45 | | |
| Ovr110.Q23 | 94.7 | 17.9 | 0.6 | 0.296 |
| Ovr110.Q24 | 3.2 | 0.36 | | |
| Ovr110.Q25 | 96.8 | 25.3 | 4 | 0.371 |
| Ovr110.Q26 | 89.2 | 8.08 | 0.9 | 0.286 |
| Ovr110.Q27 | 91.8 | 6.09 | 0.8 | 0.278 |

TABLE 2

Cell surface staining of tumor cell lines with hybridoma supernatants.

| Sample | SKBR3 | | HeLa | |
|---|---|---|---|---|
| | % Cells Positive | Mean Fluorescence Intensity (MFI) | % Cells Positive | Mean Fluorescence Intensity (MFI) |
| Anti-Ricin | 0.9 | 0.255 | 1.1 | 0.261 |
| Anti-CD71 | 97.5 | 15.1 | 99.2 | 11.1 |
| Ovr110.Q1 | 95.3 | 3.76 | 1 | 0.27 |
| Ovr110.Q3 | 54.9 | 1.01 | 0.7 | 0.266 |
| Ovr110.Q4 | 23.7 | 0.678 | 8.5 | 0.32 |
| Ovr110.Q5 | 1.3 | 0.259 | | |
| Ovr110.Q6 | 84.1 | 1.06 | 98.5 | 3.67 |
| Ovr110.Q7 | 63.5 | 1.6 | 16.3 | 0.367 |
| Ovr110.Q8 | 12.4 | 0.346 | 15 | 0.367 |
| Ovr110.Q9 | 56.6 | 0.919 | 87.7 | 1.68 |
| Ovr110.Q10 | 4 | 0.289 | | |
| Ovr110.Q11 | 98.7 | 9.71 | 0.6 | 0.25 |
| Ovr110.Q12 | 98.8 | 12 | 4.2 | 0.295 |
| Ovr110.Q13 | 42.8 | 0.945 | 76.8 | 1.44 |
| Ovr110.Q14 | 97.3 | 5.82 | 12.9 | 0.348 |
| Ovr110.Q15 | 98.6 | 10.5 | 0.8 | 0.253 |
| Ovr110.Q16 | 4.5 | 0.288 | | |
| Ovr110.Q17 | 97.4 | 6.67 | 0.6 | 0.253 |
| Ovr110.Q18 | 18.6 | 0.649 | | |
| Ovr110.Q19 | 98.9 | 10.4 | 8.1 | 0.328 |
| Ovr110.Q20 | 79.6 | 1.18 | 97.9 | 4.49 |
| Ovr110.Q21 | 7.9 | 0.325 | | |
| Ovr110.Q23 | 97.1 | 4.35 | 3.4 | 0.303 |
| Ovr110.Q24 | 44 | 0.916 | 82.3 | 1.82 |
| Ovr110.Q25 | 97.4 | 4.95 | 24.5 | 0.815 |
| Ovr110.Q26 | 8.3 | 0.314 | | |
| Ovr110.Q27 | 87.7 | 1.48 | 1 | 0.265 |

Based on data from ELISA and flow cytometry experiments, the following hybridomas were selected for single cell cloning into 96 well culture plates by cell sorting (Coulter Elite): Q1, Q3, Q11, Q12, Q15, Q19, Q23, and Q27. After 2 weeks of culture, supernatants from up to 3 hybridoma clones from each parent hybridoma were tested for staining of Ovr110 transfected 293F cells by flow cytometry. Antibodies were purified from supernatants of selected clones and re-analyzed by staining of Ovr110-transfected 293F cells and tumor cells. Anti-Ovr110 MAbs C3.2 and C6.3 which were obtained from mice immunized with recombinant Ovr110 were included as controls. Generation and characterization of Ovr110.C3.2 and Ovr110.C6.3 antibodies were previously described in PCT/US2004/014490 and PCT/US2005/040707, the disclosures of which are hereby expressly incorporated by reference. Results are shown in tables 3 and 4. All selected Q MAbs recognize native Ovr110 protein on the plasma membrane of transfected 293F cells and on tumor cells. The staining intensity for the Q-series MAbs, particularly Q1.2, Q11.12.3, Q12.2, Q15.2, Q19.6, Q23.6 and Q27.4, demonstrated live cell binding of Ovr110 expressing cells (transfected and Ovr110-positive tumor cells) which was equal to or greater than the positive control MAbs C3.2 and C6.3.

TABLE 3

Cell surface staining of Ovr110 transfected 293F cells with purified MAbs.

| | Ovr110-Transfected 293F Cells | | Mock-Transfected 293F Cells | |
|---|---|---|---|---|
| | % Cells Positive | MFI | % Cells Positive | MFI |
| Anti-Ricin | 1.1 | 0.27 | 0.9 | 0.292 |
| Anti-CD71 | 98.4 | 10 | 91.6 | 5.1 |
| C3.2 | 91.1 | 3.5 | 3.9 | 0.343 |
| Q1.2 | 92.8 | 4.53 | 12.2 | 0.433 |
| Q3.1 | 93.6 | 4.12 | 4.9 | 0.379 |
| Q11.12.3 | 93.8 | 5.47 | 40.4 | 0.959 |
| Q12.2 | 94.3 | 5.25 | 34.1 | 0.81 |
| Q15.2 | 94.2 | 5.49 | 33.3 | 0.765 |
| Q19.6 | 91.9 | 5.25 | 42 | 1 |
| Q23.6 | 92.6 | 4.98 | 33.7 | 0.773 |
| Q27.4 | 95.2 | 5.48 | 34 | 0.799 |

TABLE 4

Cell surface staining of tumor cells with purified MAbs.

| | ZR-75-1 | | SKBR3 | | HeLa | |
|---|---|---|---|---|---|---|
| | % Cells Positive | MFI | % Cells Positive | MFI | % Cells Positive | MFI |
| Anti-Ricin | 1.4 | 0.27 | 0.9 | 0.29 | 1.1 | 0.30 |
| Anti-CD71 | 74.6 | 0.96 | 99.2 | 12.40 | 99.5 | 9.39 |
| C3.2 | 32.1 | 0.46 | 25.6 | 0.52 | 0.6 | 0.23 |
| C6.3 | 60.7 | 0.68 | 39.6 | 0.71 | 4.9 | 0.37 |
| Q1.2 | 76.9 | 1.50 | 86.5 | 2.76 | 0.7 | 0.24 |
| Q3.1 | 45.1 | 0.59 | 54.2 | 0.89 | 3.3 | 0.31 |
| Q11.12.3 | 96.4 | 4.68 | 98.4 | 5.95 | 0.6 | 0.23 |
| Q12.2 | 94.1 | 3.76 | 95.3 | 4.86 | 0.7 | 0.24 |
| Q15.2 | 93 | 2.78 | 87.9 | 2.77 | 0.5 | 0.23 |
| Q19.6 | 95.6 | 4.11 | 95.2 | 4.64 | 0.4 | 0.24 |
| Q23.6 | 92.7 | 3.25 | 93.9 | 3.85 | 0.3 | 0.22 |
| Q27.4 | 93.3 | 2.92 | 94.8 | 3.90 | 0.5 | 0.24 |

Ovr110 MAb Isotypes

The isotypes of the anti-Ovr110 MAbs were determined using commercially available mouse monoclonal antibody isotyping immunoassay test kits (IsoStrip, Roche Diagnostic Corp., Indianapolis, Ind.). Results of the isotyping are listed in Table 5.

TABLE 5

Ovr110 MAb Isotypes

| Clone | Isotype |
|---|---|
| Q3.1 | IgG1 kappa |
| Q11.12.3 | IgG1 kappa |
| Q12.2 | IgG1 kappa |
| Q15.2 | IgG1 kappa |
| Q19.6 | IgG1 kappa |
| Q23.6 | IgG1 lambda |
| Q27.4 | IgG1 kappa |

Affinity Measurements of Ovr110 Antibodies

ELISA and Flow Cytometry

Binding of Ovr110 antibodies to recombinant and native Ovr110 protein was analyzed by direct ELISA, sandwich ELISA and flow cytometry. For the direct ELISA, plates were coated overnight with 100 ul recombinant Ovr110 protein at 1 ug/ml in PBS. Wells were emptied and blocked for >30 minutes with 300 ul TBST/BSA. Wells were emptied, washed with 300 ul TBST, and filled with 100 ul of antibody at 1 ug/mL in TBST/BSA. After incubation for 1 hour, wells were washed and bound antibody was detected as described in the Sandwich ELISA protocol.

Sandwich ELISA and flow cytometry experiments were done as described above, except that purified antibodies (at 1 ug/mL in TBST/BSA) were used instead of hybridoma supernatants.

Recombinant Ovr110 protein used for direct and sandwich ELISAs were encoded by Ovr110 Construct 1 and 2, respectively. ZR75-1 cells which natively express Ovr110 were used for flow cytometry experiments.

Table 6 lists the ratios of binding of specific Ovr110 antibodies to the negative control antibody anti-ricin. Ratios of OD values (for ELISA experiments) or MFI values (for flow cytometry experiments) of specific antibodies to the negative control antibody anti-ricin are listed.

TABLE 6

Binding of Ovr110 antibodies to recombinant and native Ovr110 protein.

|  | direct ELISA | sandwich ELISA | Flow cytometry |
|---|---|---|---|
| x-ricin | 1.0 | 1.0 | 1.0 |
| A87.1 | 31.3 | 17.7 | 2.2 |
| C6.3.2.1.2 | 34.4 | 18.5 | 2.5 |
| Q11.12.3 | 7.3 | 9.3 | 17.3 |
| Q12.2 | 3.6 | 3.3 | 13.9 |
| Q19.6 | 7.2 | 6.8 | 15.2 |
| Q23.6 | 6.0 | 3.9 | 12.0 |
| Q27.2 | 13.2 | 7.5 | 10.7 |

Antibodies from the A and C series as represented by Ovr110.A87.1 and Ovr110.C6.3.2.1.2 bind very well to recombinant Ovr110 protein, however binding to native Ovr110 on ZR75-1 cells is weaker. Antibodies of the Q series do not bind as strongly to recombinant Ovr110 protein as A and C series antibodies, but bind very well to native Ovr110 on ZR75-1 cells.

Dissociation Constants

To determine the affinity of anti-Ovr110 Q series antibodies to native Ovr110 protein, antibodies were labeled with NHS-Fluorescein (#46100, Pierce) following the manufacturer's instructions. Labeled antibodies were incubated with 100,000 ZR75-1 cells in FACS buffer for 2 hours at room temperature. Antibodies were used at 6 different concentrations ranging from 160 nM to 5 nM. Cells were washed twice in FACS buffer to remove unbound antibody and the mean fluorescence intensity (MFI) of cells was analyzed by flow cytometry. MFI values generated by a negative control antibody were subtracted from MFI values generated by anti-Ovr110 antibodies at equivalent antibody concentrations. Binding curves (net MFI values plotted against the antibody concentration) were analyzed with the software Prism (GraphPad). The dissociation constant KD was calculated by nonlinear regression assuming a one-site binding model. Results are summarized in table 7 below.

TABLE 7

Dissociation constants of Ovr110 antibodies.

| mAb | KD [nM] |
|---|---|
| Q11.12.3 | 0.74 |
| Q12.2 | 0.64 |
| Q19.6 | 0.53 |
| Q23.6 | 5.66 |
| Q27.4 | 4.76 |
| C6.3.2.1.2 | 33.05 |

As demonstrated above, anti-Ovr110 Q series antibodies have a higher affinity to native Ovr110 than C-series antibodies such as Ovr110.C6.3.2.1.2. Antibodies Q11.12.3, Q12.2 and Q19.6 bind very strongly to native Ovr110 protein on ZR75-1 cells with dissociation constants of 0.74 nM, 0.64 nM and 0.53 nM, respectively.

The preferential binding of the anti-Ovr110 antibodies to native Ovr110 and high affinity to native Ovr110 demonstrate that anti-Ovr110 antibodies are useful as diagnostic or therapeutic agents. An antibody with nanomolar or picomolar range affinity is considered useful as a therapeutic agent. Ovr110 MAbs Q11.12.3, Q12.2, Q19.6, Q23.6 and Q27.4 have KD values and binding characteristics (live cell binding) which demonstrate their utility as therapeutic agents. These characteristics demonstrate that the anti-Ovr110 Q-series antibodies are better suited for use as diagnostic or therapeutic agents than anti-Ovr110 antibodies described previously.

Structural Characterization of the Ovr110 Antibody IgG Heavy and Light Chains

The nucleotide sequences of the variable regions of the IgG heavy and light chains of antibodies from hybridomas Q11, Q12, Q19, Q23 and Q27 were determined using commercially available kits, e.g. RNeasy Mini Kit (Qiagen, Hilden, Germany) and 5'RACE System (Invitrogen). The sequences of the heavy and light chains of the antibodies were evaluated using the Kabat system of CDR region determination (Kabat et al. Sequences of proteins of immunological interest, 5th edition, Public Health Service, National Institutes of Health, Bethesda, Md.) to identify the heavy chain CDR2 and CDR3 regions and the light chain CDR1, CDR2 and CDR3 regions. The heavy chain CDR1 regions of the antibodies were determined as described by Clothia & Lesk (J. Mol. Biol. (1987) 196, 901-917).

Nucleic acid and amino acid sequences of the light chain variable region of Ovr110.Q11 are shown in SEQ ID NO: 1 and 2, respectively. Light chain CDR1, CDR2 and CDR3 regions are shown in SEQ ID NO: 3, 4 and 5, respectively.

```
Ovr110.Q11_LCVD.na, SEQ ID NO: 1:
GAAAATGTTCTCACCCAGTCTCCAGCAATCATGTCTGCATCTCCAGGGGAAAAGGTCACCATGACCTGTAGT

GCCAGCTCAAGTGTAAGTTACATGCACTGGTACCAGCAGAAGTCAAGCACCTCCCCCAAACTCTGGATTTAT

GACACATCCAAACTGGCTTCTGGAGTCCCAGGTCGCTTCAGTGGCAGTGGGTCTGGAAACTCCTACTCTCTC

ACGATCAGCAGCATGGAGGCTGAAGATGTTGCCACTTATTACTGTTTTCAGGGGAGTGGGTACCCATTCACG

TTCGGCTCGGGGACAAAGTTGGAAATAAAACGGGCTGAT

Ovr110.Q11_LCVD.aa, SEQ ID NO: 2:
ENVLTQSPAIMSASPGEKVTMTCSASSSVSYMHWYQQKSSTSPKLWIYDTSKLASGVPGRFSGSGSGNSYSL

TISSMEAEDVATYYCFQGSGYPFTFGSGTKLEIKRAD

Ovr110.Q11_LCVD_CDR1, SEQ ID NO: 3:
SASSSVSYMH

Ovr110.Q11_LCVD_CDR2, SEQ ID NO: 4:
DTSKLAS

Ovr110.Q11_LCVD_CDR3, SEQ ID NO: 5:
FQGSGYPFT
```

Nucleic acid and amino acid sequences of the heavy chain variable region of Ovr110.Q11 are shown in SEQ ID NO: 6 and 7, respectively. Light chain CDR1, CDR2 and CDR3 regions are shown in SEQ ID NO: 8, 9 and 10, respectively.

```
Ovr110.Q11_HCVD.na, SEQ ID NO: 6:
GATGTACAGCTTCAGGAGTCAGGACCTGGCCTCGTGAAACCTTCTCAGTCTCTGTCTCTCACCTGCTCTGTC

ACTGGCTACTCCATCACCAGTGGTTATTTCTGGAGCTGGATCCGGCAGTTTCCAGGAAACAAACTGGAATGG

ATGGGCTTCATAAGCTACGACGGTACCAATAGCTACAACCCATCTCTCAAAAATCGGATCTCCATTACTCGT

GACACATCTAAGAACCAGTTTTTCCTGAGGTTGAATTCTGTGACTAAAGAGGACACAGCTACATATTACTGT

GCCAGGAAGTTACTATGGCTACGCTTTGACTACTGGGGCCAAGGCACCACTCTCACAGTCTCCTCAGCCAAA

ACG

Ovr110.Q11_HCVD.aa, SEQ ID NO: 7:
DVQLQESGPGLVKPSQSLSLTCSVTGYSITSGYFWSWIRQFPGNKLEWMGFISYDGTNSYNPSLKNRISITR

DTSKNQFFLRLNSVTKEDTATYYCARKLLWLRFDYWGQGTTLTVSSAKT

Ovr110.Q11_HCVD_CDR1, SEQ ID NO: 8:
GYSITSGYFWS

Ovr110.Q11_HCVD_CDR2, SEQ ID NO: 9:
FISYDGTNSYNPSLKN

Ovr110.Q11_HCVD_CDR3, SEQ ID NO: 10:
KLLWLRFDY
```

Nucleic acid and amino acid sequences of the light chain variable region of Ovr110.Q12 are shown in SEQ ID NO: 11 and 12, respectively. Light chain CDR1, CDR2 and CDR3 regions are shown in SEQ ID NO: 13, 14 and 15, respectively.

```
Ovr110.Q12_LCVD.na, SEQ ID NO: 11:
CAAATTGTTCTCACCCAGTCTCCAGCAATCATGTCTGCATCTCCAGGGGAGAAGGTCACCATGACCTGCAGT

GCCAGCTCAGGTATAAGTTACATGCACTGGTACCAGCAGAAGCCAGGCACCACCCCCAAAAGATGGATTTAT

GACGCATCCAAACTGGCTTCTGGAGTCCCTTCTCGCTTCAGTGGCAGTGGGTCTGGGACCTCTTATTCTCTC

ACAATCAGCAGCATGGAGGCTGAAGATGCTGCCACTTATTACTGCCATCAGCGGCGTAGTTACCCATTCACG

TTCGGCTCGGGGACAAAGTTGGAAATAAAACGGGCTGAT

Ovr110.Q12_LCVD.aa, SEQ ID NO: 12:
QIVLTQSPAIMSASPGEKVTMTCSASSGISYMHWYQQKPGTTPKRWIYDASKLASGVPSRFSGSGSGTSYSL

TISSMEAEDAATYYCHQRRSYPFTFGSGTKLEIKRAD
```

-continued

Ovr110.Q12_LCVD_CDR1, SEQ ID NO: 13:
SASSGISYMH

Ovr110.Q12_LCVD_CDR2, SEQ ID NO: 14:
DASKLAS

Ovr110.Q12_LCVD_CDR3, SEQ ID NO: 15:
HQRRSYPFT

Nucleic acid and amino acid sequences of the heavy chain variable region of Ovr110.Q12 are shown in SEQ ID NO: 16 and 17, respectively. Light chain CDR1, CDR2 and CDR3 regions are shown in SEQ ID NO: 18, 19 and 20, respectively.

Ovr110.Q12_HCVD.na, SEQ ID NO: 16:
CAGGTCCAACTGCAGCAGCCTGGGGCTGAGCTTGTGAAGCCTGGGGCTACAGTGAAGCTGTCCTGCAAGACT

TCTGGCTACACCTTCACCAGCTACTGGATGCACTGGGTGAAGCAGAGGCCTGGACAAGGCCTTGAGTGGATC

GGAGAGATTGATCCTTCTGATAGTTATACTAACTACAATCAAAAGTTCAAGGGCAAGGCCACATTGACTGTA

GACACATCCTCCACCACAGCCTACATGCAGCTCAGCAGCCTGACATCTGAAGACTCTGCGGTCTATTACTGT

GCAAGAGAGTATGGTAACAACGATGCTATGGACTACTGGGGTCAAGGAACCTCAGTCACCGTCTCCTCAGCC

AAAACG

Ovr110.Q12_HCVD.aa, SEQ ID NO: 17:
QVQLQQPGAELVKPGATVKLSCKTSGYTFTSYWMHWVKQRPGQGLEWIGEIDPSDSYTNYNQKFKGKATLTV

DTSSTTAYMQLSSLTSEDSAVYYCAREYGNNDAMDYWGQGTSVTVSSAKT

Ovr110.Q12_HCVD_CDR1, SEQ ID NO: 18:
GYTFTSYWMH

Ovr110.Q12_HCVD_CDR2, SEQ ID NO: 19:
EIDPSDSYTNYNQKFKG

Ovr110.Q12_HCVD_CDR3, SEQ ID NO: 20:
EYGNNDAMDY

Nucleic acid and amino acid sequences of the light chain variable region of Ovr110.Q19 are shown in SEQ ID NO: 21 and 22, respectively. Light chain CDR1, CDR2 and CDR3 regions are shown in SEQ ID NO: 23, 24 and 25, respectively.

Ovr110.Q19_LCVD.na, SEQ ID NO: 21:
GAAATTGTTCTCACCCAGTCTCCAGCAATCATGTCTGTATATCTAGGGGAAAAGGTCACCATGACCTGCAGT

GCCAGCTTAAGTGTTAGTTACATGCACTGGTACCAGCAGAAGTCAAGCACCTCCCCCAAACTCTGGATTTAT

GACACATCCAAAGTGGCTTCTGGAGTCCCAGGTCGCTTCAGTGGCAGTGGGTCTGGAAACTCTTATTCTCTC

ACGATCAGCAGCATGGAGGCTGAAGATGTTGCCACTTATTACTGTTTTCAGGGGAGTGGGTACCCATTCACG

TTCGGCTCGGGGACAAAGTTGGAAATAAAACGGGCTGAT

Ovr110.Q19_LCVD.aa, SEQ ID NO: 22:
EIVLTQSPAIMSVYLGEKVTMTCSASLSVSYMHWYQQKSSTSPKLWIYDTSKVASGVPGRFSGSGSGNSYSL

TISSMEAEDVATYYCFQGSGYPFTFGSGTKLEIKRAD

Ovr110.Q19_LCVD CDR1, SEQ ID NO: 23:
SASLSVSYMH

Ovr110.Q19_LCVD CDR2, SEQ ID NO: 24:
DTSKVAS

Ovr110.Q19 LCVD_CDR3, SEQ ID NO: 25:
FQGSGYPFT

Nucleic acid and amino acid sequences of the heavy chain variable region of Ovr110.Q19 are shown in SEQ ID NO: 26 and 27, respectively. Light chain CDR1, CDR2 and CDR3 regions are shown in SEQ ID NO: 28, 29 and 30, respectively.

```
Ovr110.Q19_HCVD.na, SEQ ID NO: 26:
GATGTACTGCTTCAGGAGTCAGGACCTGGCCTCGTGAAAGCTTCTCAGTCTCTGTCTCTCACCTGTTCTGTC

ACTGGCTACTCCATCACCAGTGGTTATTTCTGGAACTGGATCCGGCAGTTTCCGGGAAACAAACTGGAATGG

ATGGGCTACATAAGCTACGACGGTGGCAATAGCTACAACCCATCTCTCAAAAATCGAATCTCCATCACTCGT

GACACATCTAAGAACCAGTTTTTCCTGAGGATGAAATCTGTGACTGCTGAGGACACAGCTACATATTACTGT

GCAAGGAAGGCACTATGGTTACGCTTTGATTATTGGGGCCAGGGCACCACTCTCACAGTCTCCTCAGCCAAA

ACG

Ovr110.Q19_HCVD.aa, SEQ ID NO: 27:
DVLLQESGPGLVKASQSLSLTCSVTGYSITSGYFWNWIRQFPGNKLEWMGYISYDGGNSYNPSLKNRISITR

DTSKNQFFLRMKSVTAEDTATYYCARKALWLRFDYWGQGTTLTVSSAKT

Ovr110.Q19_HCVD_CDR1, SEQ ID NO: 28:
GYSITSGYFWN

Ovr110.Q19_HCVD_CDR2, SEQ ID NO: 29:
YISYDGGNSYNPSLKN

Ovr110.Q19_HCVD_CDR3, SEQ ID NO: 30:
KALWLRFDY
```

Nucleic acid and amino acid sequences of the light chain variable region of Ovr110.Q23 are shown in SEQ ID NO: 31 and 32, respectively. Light chain CDR1, CDR2 and CDR3 regions are shown in SEQ ID NO: 33, 34 and 35, respectively.

```
Ovr110.Q23_LCVD.na, SEQ ID NO: 31:
CAGGCTGTTGTGACTCAGGAATCTGCACTCACCACATCACCTGGTGAAACAGTCACACTCACTTGTCGCTCA

AGTACTGGGGCTGTTACAACTAGTAACTATGCCAACTGGGTCCAAGAAAAACCAGATCATTTATTCACTGGT

CTAATAGGTGGTACCGACAACCGACCTCCAGGTGTTCCTGCCAGATTCTCAGGCTCCCTGATTGGAGACAAG

GCTGCCCTCACCATCACAGGGACACAGACTGAGGATGAGGCAATATATTTCTGTGCTCTGTGGTACAGCAAC

CATTGGGTGTTCGGTGGAGGAACCAAACTGACTGTCCTAGGCCAGCCCAAG

Ovr110.Q23_LCVD.aa, SEQ ID NO: 32:
QAVVTQESALTTSPGETVTLTCRSSTGAVTTSNYANWVQEKPDHLFTGLIGGTDNRPPGVPARFSGSLIGDK

AALTITGTQTEDEAIYFCALWYSNHWVFGGGTKLTVLGQPK

Ovr110.Q23_LCVD_CDR1, SEQ ID NO: 33:
RSSTGAVTTSNYAN

Ovr110.Q23_LCVD_CDR2, SEQ ID NO: 34:
LIGGTDNRPP

Ovr110.Q23_LCVD_CDR3, SEQ ID NO: 35:
ALWYSNHWV
```

Nucleic acid and amino acid sequences of the heavy chain variable region of Ovr110.Q23. are shown in SEQ ID NO: 36 and 37, respectively. Light chain CDR1, CDR2 and CDR3 regions are shown in SEQ ID NO: 38, 39 and 40, respectively.

```
Ovr110.Q23_HCVD.na, SEQ ID NO: 36:
CAGGTTCAGCTGCAGCAGTCTGGAGCTGAGTTGATGAAGCCTGGGGCCTCAGTGAAGATTTCCTGCAAGGCT

ACTGGCTACACATTCAGTAGCTACTGGATAGAGTGGGTAAAGCAGAGGCCTGGACATGGCCTTGAGTGGATT

GGAGAGATTTTACCTGGAAGTGGTATTACTAAGTACAATGAGAAGTTCAAGACCAAGGCCACATTCACTGCA

GATACATCCTCCAACACAGCCTACATGCAACTCAGCAGCCTGACATCTGAGGACTCTGCCGTCTATTACTGT

GCAAGATATTACTTCGGCAGTGTCAACTTTTACTTTGACTGCTGGGGCCAAGGTACCACTCTCACAGTCTCC

TCAGCCAAAACG

Ovr110.Q23_HCVD.aa, SEQ ID NO: 37:
QVQLQQSGAELMKPGASVKISCKATGYTFSSYWIEWVKQRPGHGLEWIGEILPGSGITKYNEKFKTKATFTA

DTSSNTAYMQLSSLTSEDSAVYYCARYYFGSVNFYFDCWGQGTTLTVSSAKT

Ovr110.Q23_HCVD_CDR1, SEQ ID NO: 38:
GYTFSSYWIE

Ovr110.Q23_HCVD_CDR2, SEQ ID NO: 39:
EILPGSGITKYNEKFKT

Ovr110.Q23_HCVD_CDR3, SEQ ID NO: 40:
YYFGSVNFYFDC
```

Nucleic acid and amino acid sequences of the light chain variable region of Ovr110.Q27 are shown in SEQ ID NO: 41 and 42, respectively. Light chain CDR1, CDR2 and CDR3 regions are shown in SEQ ID NO: 43, 44 and 45, respectively.

```
Ovr110.Q27_LCVD.na, SEQ ID NO: 41:

GACATTGTGCTGACCCAGTCCCACAAAATCATGTCAACATCAGTAGGAGACAGGGTCAGCATCACCTGCAAG

GCCAGTCAGGATGTGAGAACTGCTGTAGCCTGGTATCAACAGAAACCAGGACAATCTCCTAAATTACTGATT

AAGTCGGCATCCTACCGGTACACTGGAGTCCCTGATCGCTTCAGTGGCAGTGGATCTGGGACGGATTTCACT

TTCACCATCAGCAGTGTGCAGGCTGAAGACCTGGCAGTTTATTACTGTCAGCAACATTATAGTAATCCGACG

TTCGGTGGAGGCACCAAGCTGGAAATCAAACGGGCTGAT

Ovr110.Q27_LCVD.aa, SEQ ID NO: 42:
DIVLTQSHKIMSTSVGDRVSITCKASQDVRTAVAWYQQKPGQSPKLLIKSASYRYTGVPDRFSGSGSGTDFT

FTISSVQAEDLAVYYCQQHYSNPTFGGGTKLEIKRAD

Ovr110.Q27_LCVD_CDR1, SEQ ID NO: 43:
KASQDVRTAVA

Ovr110.Q27_LCVD_CDR2, SEQ ID NO: 44:
SASYRYT

Ovr110.Q27_LCVD_CDR3, SEQ ID NO: 45:
QQHYSNPT
```

Nucleic acid and amino acid sequences of the heavy chain variable region of Ovr110.Q27 are shown in SEQ ID NO: 46 and 47, respectively. Light chain CDR1, CDR2 and CDR3 regions are shown in SEQ ID NO: 48, 49 and 50, respectively.

PCT/US2004/014490 and PCT/US2005/040707, the disclosures of which are hereby expressly incorporated by reference) as positive controls and anti-ricin antibody TFTB1 (ATCC, Manassas, Va.) as a negative control.

```
Ovr110.Q27_HCVD.na, SEQ ID NO: 46:
```

CAGGTTCAGCCCCAGCAGTCTGGGGCTGAGCTGGCAAGACCTGGGGCTTCAGTGAAGTTGTCCTGCAAGGCT

TCTGGCTACACCTTTACTACCTACTGGATGCAGTGGGTAAAACAGAGGCCTGGACAGGGTCTGGAGTGGATT

GGGGCTATTTATCCTGGAGATGGTGATACTCGGTACACTCAGAAGTTCAAGGGCAAGGCCACATTGACTGCA

GATAAATCCTCCAGCACAGCCTACATGCAACTCAGCAGCTTGGCATCTGAGGACTCTGCGGTCTATTACTGT

GCAATTAACTGGGGCTATGCTATGGACTACTGGGGTCAAGGAACCTCAGTCACCGTCTCCTCAGCCAAAACG

```
Ovr110.Q27_HCVD.aa, SEQ ID NO: 47:
```

QVQPQQSGAELARPGASVKLSCKASGYTFTTYWMQWVKQRPGQGLEWIGAIYPGDGDTRYTQKFKGKATLTA

DKSSSTAYMQLSSLASEDSAVYYCAINWGYAMDYWGQGTSVTVSSAKT

```
Ovr110.Q27_HCVD CDR1, SEQ ID NO: 48:
GYTFTTYWMQ

Ovr110.Q27_HCVD_CDR2, SEQ ID NO: 49:
```

AIYPGDGDTRYTQKFKG

```
Ovr110.Q27_HCVD_CDR3, SEQ ID NO: 50:
NWGYAMDY
```

Example 2

Epitope Mapping of Oval® MAbs

The epitopes recognized by a panel of antibodies from the Q series were characterized by competition ELISA and by screening overlapping peptides for reactivity with the antibodies through an ELISA-based assay.

Competition ELISA

For the competition ELISA Q-series MAbs were evaluated alongside anti-Ovr110 MAbs A87.1 and C6.3 (described in Purified antibodies were biotinylated with Sulfo-NHS-LC-Biotin (Pierce, #21335). Recombinant Ovr110 was coated on plates as described in the Sandwich ELISA protocol above. Wells were filled with 50 uL unlabeled antibody ("blocking antibody") at 20 ug/mL in TBST/BSA and incubated for 30 min. Fifty uL/well biotinylated antibody ("detecting antibody") at 2 ug/mL was added and plates incubated for 15 min. Plates were washed with TBST and wells were filled with 100 uL/well streptavidin-HRP (Pierce, #21126). After 30 min incubation, plates were washed with TBST and 100 uL/well of HRP substrate 3,3',5,5'-tetramethyl benzidine (#S1599; Dako Cytomation, Carpinteria, Calif.) were added. The reaction was stopped by adding 100 uL 1N hydrochloric acid. The enzymatic reaction was quantified by measuring the solution's absorbance at 450 nm wavelength.

Each antibody was tested as both a blocking and detecting antibody, in all possible combinations. The results of the competition ELISA are shown in table 8 as specific signal/noise ratios, i.e. each signal in a given column was divided by the signal obtained when the same antibody was used for blocking and detection. Unlabeled blocking MAbs are listed on the Y-axis with labeled detecting MAbs on the X-axis.

TABLE 8

Pairing of Ovr110 MAb by competition ELISA

|         | Q11.12.3 | Q19.6 | Q12.2 | Q27.4 | Q23.6 | Q15.2 | Q3.1 | A87.1 | C6.3 |
|---------|----------|-------|-------|-------|-------|-------|------|-------|------|
| Q11.12.3 | 1.0 | 1.0 | 1.0 | 4.7 | 4.5 | 11.7 | 1.3 | 6.4 | 1.2 |
| Q19.6   | 1.0 | 1.0 | 1.1 | 4.7 | 4.8 | 11.7 | 1.3 | 6.6 | 1.2 |
| Q12.2   | 1.2 | 1.1 | 1.0 | 4.3 | 3.6 | 11.6 | 1.4 | 6.7 | 1.2 |
| Q27.4   | 5.5 | 6.5 | 3.1 | 1.0 | 1.0 | 11.8 | 1.4 | 6.7 | 1.2 |
| Q23.6   | 5.2 | 6.0 | 2.8 | 2.2 | 1.0 | 2.9 | 1.4 | 6.7 | 1.2 |
| Q15.2   | 5.2 | 5.6 | 3.0 | 4.9 | 0.7 | 1.0 | 1.3 | 6.5 | 1.2 |
| Q3.1    | 2.2 | 1.7 | 0.8 | 5.1 | 3.9 | 11.0 | 1.0 | 6.5 | 1.2 |
| A87.1   | 5.0 | 5.2 | 2.8 | 4.8 | 4.4 | 11.1 | 1.3 | 1.0 | 0.1 |
| C6.3    | 5.2 | 5.9 | 3.0 | 4.6 | 4.4 | 10.6 | 1.3 | 6.0 | 1.0 |
| ricin   | 5.0 | 5.3 | 2.8 | 4.9 | 4.8 | 11.0 | 1.3 | 6.4 | 1.1 |

Results from the competition ELISA demonstrate that the Q MAbs bind to a different epitope than A87.1 and C6.3. MAbs Q11.12.3, Q12.2 and Q19.6 bind to overlapping epitopes, since they block each other. MAbs Q23.6 and Q27.4 bind to overlapping epitopes which are different from the epitopes recognized by Q11.12.3, Q12.2 and Q19.6.

Peptide Mapping

Twenty-four peptides were ordered from SynPep (Dublin, Calif.). Peptides 1-23 were 15-mers overlapping 5 amino acids with the adjacent peptides. Peptide 24 contained 8 amino acids. The peptide sequences started at amino acid G21 after the signal sequence and ended at A258. These peptides span the extracellular region of the mature Ovr110 protein. The peptides were provided in small aliquots with a range of 1-3 mg dissolved in 0.2-0.5 mL water. A 1:400 dilution was made in PBS of each peptide and 50 µl were added to each well in duplicate on 96-well 4× Costar plates (#3690; Costar Corporation; Cambridge, Mass.) and left overnight. The next day, the plates were flicked dry and blocked with TBST/BSA for approximately 1 hour. Anti-Ovr110 antibodies (50 µL) were added either at approximately 1 µg/mL per well and incubated at room temperature for 1 hour. The plates were washed 3 times with TBST wash buffer. The secondary conjugate, goat anti-mouse Ig Fc-AP, (Pierce, Rockford, Ill.) was diluted 1:5000 in a TBST/BSA solution and 50 µl was added to each well. The plates were shaken for 1 hour at room temperature. The plates were washed 3 times before 50 µL of substrate was added to each well and incubated for 35 minutes at room temperature. The substrate used was pNPP in 1×DEA (1 mg/ml). To visualize the assay, plates were read at 405 nm on a SpectraMaxPlus (Molecular Devices, Sunnyvale, Calif.). The background signal was below 0.2 OD.

Antibody Q3.1 mapped to peptide 23 with a signal of 1.4 OD. Antibodies Q4 and Q5 mapped to peptide 13 with signals of 1.9 OD and 1.8 OD, respectively.

The other Q series antibodies, Q1, Q7, Q8, Q11, Q12, Q13, Q14, Q15, Q17, Q19, Q20, Q23, Q25, Q26, and Q27 did not map to a peptide which in conjunction with the demonstrated binding to Ovr110-expressing cells above indicates these MAbs bind conformational epitopes on Ovr110.

Example 3

Cellular Binding of Ovr110 MAbs

To demonstrate utility as therapeutic agents anti-Ovr110 Q-series antibodies described above were evaluated for binding to Ovr110-expressing cancer cells, internalization by Ovr110-expressing cancer cells and killing of Ovr110-expressing cancer cells with a toxin conjugated secondary antibody. All cell lines in the example below were obtained from the American Type Culture Collection (ATCC; Manassas, Va.).

Surface Binding of Q-Series MAbs to Tumor Cells by Immunofluorescence

Anti-Ovr110 Q-series antibodies were evaluated for the ability to bind to the surface of various live tumor cells including ZR-75-1 cells (breast cancer), RL95.2 cells (endometrial cancer), OVCAR3 cells (ovarian cancer) and HeLa cells (cervical cancer). ZR-75-1, RL95.2 and OVCAR3 are positive for Ovr110 protein expression but HeLa is negative. These cell lines were seeded onto sterile 12 mm glass coverslips and cultured at 37° C. in DMEM/10% FBS for 48 hr prior to treatment with the primary antibodies. Anti-Ovr110 Q series mAbs and control antibodies were added to the medium at a final concentration of 5 ug/ml and incubated for one hour on ice. The coverslips were then washed three times with 1×PBS. Following fixation with 4% formaldehyde in Phosphate Buffered Saline (PBS), these cells were incubated with a secondary Cy3-labeled donkey anti-mouse (Jackson Immunoresearch Laboratories, West Grove, Pa.) at a concentration of 5 ug/ml for 45 min. Following washing, the coverslips were mounted in Vectastain (Vector, Burlingame, Calif.), a medium containing DAPI to visualize the cell nuclei and observed in a Zeiss Axiophot fluorescence microscope (Carl Zeiss, Thornwood, N.Y.) equipped with the appropriate fluorescent filters. Micrographs were recorded using a CCD camera. Since the anti-transferrin receptor (TfnR) is localized to the cell surface, anti-TfnR MAb 5E9 from the ATCC (Manassas, Va.) was used as a positive control.

FIG. 1 shows exemplary immunofluorescence staining images of live cell surface binding of an anti-Ovr110 antibody to tumor cells expressing Ovr110. FIGS. 1A, 1B and 1C show cell surface binding of mAb Ovr110.Q12.2 to breast cancer (ZR-75-1), endometrial cancer (RL95.2) and ovarian cancer (OVCAR3) cells, respectively. No staining is observed in HeLa cells (FIG. 1D) which do not express Ovr110. Table 9 below summarizes the results of the surface binding experiments. Plus signs denote intensity of staining.

TABLE 9

Surface Binding of Ovr110 antibodies to Live Cancer Cells

| Ovr110 mAbs | ZR-75-1 | RL95.2 | OVCAR3 | HeLa |
|---|---|---|---|---|
| Q1.2 | ++ | ++ | +/− | −− |
| Q3.1 | ++ | + | −− | −− |
| Q11.12.3 | +++ | ++ | + | −− |
| Q12.2 | +++ | ++ | + | −− |
| Q15.2 | +++ | +++ | + | −− |
| Q19.6 | ++ | +++ | + | −− |
| Q23.6 | ++ | ++ | + | −− |
| Q27.4 | ++ | + | +/− | −− |
| anti-TfnR | + | +++ | ++ | +++ |
| no mAb | −− | −− | −− | −− |

The results in FIG. 1 and Table 7 demonstrate that anti-Ovr110 mAbs specifically bind to native Ovr110 on the surface of tumor cells that express Ovr110 and are useful as diagnostic and therapeutic agents.

Internalization of Q-series MAbs by Live Tumor Cells

Purified mAbs were labeled with Alexa Fluor 488 (Molecular Probe, Eugene, Oreg.) according to manufacturer's instructions. The following cancer cell lines were used in this study: ZR-75-1 (breast cancer), SKBR3 (breast cancer) and HeLa (cervical cancer). Western blots confirmed that ZR-75-1 and SKBR3 cells express Ovr110 protein and HeLa cells do not. Cells were seeded on coverslips for two days to let the cells fully attach. Alexa-488 labeled mAbs were then added to the live cells at 5 ug/mL for 24 hours at 37 degree incubator with 5% $CO_2$. Cells were then washed three times with 1×PBS. Surface staining of the mAbs was quenched by incubating the cells with 10 ug/mL anti-Alexa 488 rabbit antibody (Molecular Probe, Eugene, Oreg.) on ice for 1 hour. After washing three times with 1×PBS, cells were fixed with 4% formaldehyde for 10 min at room temperature. Residual formaldehyde was removed by washing the cells once with 1×PBS. The coverslips were then mounted in Vectastain (Vector, Burlingame, Calif.), a medium containing DAPI to visualize the cell nuclei, and observed under a Zeiss Axiophot fluorescence microscope (Carl Zeiss, Thornwood, N.Y.) equipped with the appropriate fluorescent filters. Micrographs were recorded using a CCD camera. Since the transferrin receptor (TfnR) is localized to the cell surface and can internalize, anti-TfnR MAb 5E9 from the ATCC (Manassas, Va.) was used as a positive control. Ricin is not expressed by mammalian cells and does not localize to the cell surface, therefore the anti-ricin MAb TFTB1 (ATCC, Manassas, Va.) was used as a negative control.

FIG. 2 shows exemplary immunofluorescence images of internalization of an anti-Ovr110 antibody by live tumor cells expressing Ovr110. FIGS. 2A and 2B respectively show internalization of mAb Ovr110.Q11.12.3 into ZR-75-1 and SKBR3 breast tumor cells. No internalization is observed in HeLa cells (FIG. 2C) which do not express Ovr110. Table 10 below summarizes the results of the internalization experiments. Plus signs (+) indicate the intensity of staining in the cell indicating internalization, n/d indicates that no internalization was observed.

TABLE 10

| Alexa488-labeled Ovr110 Abs | Internalization in ZR-75-1 | Internalization in SKBR3 | Internalization in HeLa |
|---|---|---|---|
| Anti-ricin | −− | −− | −− |
| Anti-TfnR | +++ | +++ | +++ |
| Q1.2 | n/d | n/d | n/d |
| Q3.1 | n/d | n/d | n/d |
| Q11.12.3 | +++ | +++ | −− |
| Q12.2 | + | + | −− |
| Q15.2 | n/d | n/d | n/d |
| Q19.6 | ++ | ++ | −− |
| Q23.6 | ++ | ++ | −− |
| Q27.4 | +/− | +/− | −− |

The results in FIG. 2 and Table 10 demonstrate that anti-Ovr110 mAbs are unexpectedly internalized by live Ovr110 expressing cancer cells and are useful as therapeutic agents.

Tumor Cell Killing by Q-series MAbs and MAb-ZAP Saporin Conjugate

Tumor cells from ZR-75-1 (breast cancer), SKBR3 (breast cancer) and HCT116 (Ovr110 negative colon cancer) cell lines were seeded at 3000, 3000, and 1500 cells/well respectively on 96 well plates and left to adhere overnight. Monoclonal antibodies were added to live cells at 0.4 and 2.0 ug/mL the next day (day 0) with or without 1 ug/mL of the goat anti-mouse Ig saporin conjugate mAb-ZAP from Advanced Targeting Systems (San Diego, Calif.). mAb-ZAP, upon internalization, releases saporin which kills the cells. Since the transferrin receptor (TfnR) is localized to the cell surface and can internalize, anti-TfnR MAb 5E9 from the ATCC (Manassas, Va.) was used as a positive control MAb. Ricin does not localize to the cell surface, therefore the anti-ricin MAb TFTB1 (ATCC, Manassas, Va.) was used as a negative control for killing. On day 5, cell viability was measured using the CellTiterGlo Luminescent Cell Viability assay from Promega (Madison. WI).

Results are presented in Tables 11a, 11b and 11c below as percentage of growth of cells treated with MAbs+MAb-ZAP compared to non-treated cells. Percentage of cell growth was calculated by normalizing the luminescence unit of samples to medium alone (100%) on each plate.

TABLE 11a

ZR-75-1 cell killing by Q-series Ovr110 MAbs & MAb-ZAP Saporin Conjugate

Percentage growth compared to wells with media alone

| MAb Clone | MAb alone | | MAb with 1.0 ug/mL mAb-ZAP | |
|---|---|---|---|---|
| | MAb (0.4 ug/mL) | MAb (2.0 ug/mL) | MAb (0.4 ug/mL) | MAb (2.0 ug/mL) |
| Anti-ricin | 107.1% | 104.9% | 92.3% | 95.4% |
| anti-TfnR | 104.8% | 116.5% | 35.0% | 49.3% |
| Q1.2 | 106.0% | 99.2% | 85.8% | 83.9% |
| Q3.1 | 97.6% | 103.0% | 103.6% | 104.2% |
| Q11.12.3 | 108.6% | 112.8% | 31.5% | 44.3% |
| Q12.2 | 113.1% | 102.3% | 38.0% | 67.7% |
| Q15.2 | 95.3% | 98.6% | 45.6% | 57.8% |
| Q19.6 | 99.1% | 99.6% | 28.1% | 46.5% |
| Q23.6 | 102.4% | 97.2% | 37.5% | 45.5% |
| Q27.4 | 101.3% | 98.3% | 60.6% | 69.5% |

TABLE 11b

SKBR3 cell killing by Q-series Ovr110
MAbs & MAb-ZAP Saporin Conjugate

Percentage growth compared to wells with media alone

| MAb Clone | MAb alone | | MAb with 1.0 ug/mL mAb-ZAP | |
|---|---|---|---|---|
| | MAb (0.4 ug/mL) | MAb (2.0 ug/mL) | MAb (0.4 ug/mL) | MAb (2.0 ug/mL) |
| Anti-ricin | 96.6% | 102.2% | 82.7% | 86.6% |
| anti-TfnR | 93.9% | 94.35 | 18.4% | 44.6% |
| Q1.2 | n/d | n/d | n/d | n/d |
| Q3.1 | n/d | n/d | n/d | n/d |
| Q11.12.3 | 98.2% | 95.3% | 32.7% | 47.7% |
| Q12.2 | 95.2% | 100.7% | 58.5% | 68.4% |
| Q15.2 | 93.3% | 100.9% | 67.8% | 81.7% |
| Q19.6 | 97.6% | 97.4% | 49.8% | 25.0% |
| Q23.6 | 98.8% | 101.2% | 68.9% | 73.6% |
| Q27.4 | 98.9% | 101.2% | 68.9% | 73.6% |

TABLE 11c

HCT116 cell killing by Q-series Ovr110
MAbs & MAb-ZAP Saporin Conjugate

Percentage growth compared to wells with media alone

| MAb Clone | MAb alone | | MAb with 1.0 ug/mL mAb-ZAP | |
|---|---|---|---|---|
| | MAb (0.4 ug/mL) | MAb (2.0 ug/mL) | MAb (0.4 ug/mL) | MAb (2.0 ug/mL) |
| Anti-ricin | 98.3% | 97.4% | 97.4% | 99.1% |
| anti-TfnR | 103.0% | 109.4% | 10.0% | 24.9% |
| Q1.2 | n/d | n/d | n/d | n/d |
| Q3.1 | n/d | n/d | n/d | n/d |
| Q11.12.3 | 102.6% | 100.7% | 106.7% | 101.9% |
| Q12.2 | 104.3% | 104.7% | 101.4% | 102.5% |
| Q15.2 | 105.8% | 102.2% | 103.7% | 104.0% |
| Q19.6 | 97.9% | 101.8% | 100.1% | 102.2% |
| Q23.6 | 99.4% | 101.0% | 98.3% | 99.4% |
| Q27.4 | 97.2% | 97.5% | 99.0% | 99.8% |

The results in Tables 11a, 11b and 11c demonstrate that anti-Ovr110 MAbs specifically bind to, internalize and kill live Ovr110 expressing cancer cells in conjunction with an internalized toxin. The toxin may be internalized via conjugation to a secondary antibody, or via direct conjugation to the primary anti-Ovr110 antibody. The Q-series anti-Ovr110 antibodies are useful as therapeutic agents for killing Ovr110 expressing tumor cells.

Example 4

Ovr110 MAb Therapeutic Efficacy

Anti-Ovr110 monoclonal antibodies were evaluated for therapeutic anti-tumor efficacy against Ovr110 expressing tumors. The MAbs were tested as single agents and in combination with a known small molecule anti-tumor compound in a human tumor model.

ZR-75-1 Orthotopic Xenograft

Our prior immunohistochemistry and Western immunoblot studies demonstrated high level expression of Ovr110 in the ZR-75-1 tumor. Therefore, the ZR-75-1 human breast tumor orthotopic xenograft model with paclitaxel as the positive control compound was used to evaluate efficacy of Ovr110 MAbs. Paclitaxel is small molecule drug known to have efficacy against gynecological tumors including breast and ovarian tumors. Anti-Ovr110 antibody anti-tumor efficacy was evaluated by determining the in-study tumor growth inhibition (TGI) and overall increase in subject survival by single-agent and combination treatment regimens.

Materials and Methods

The monoclonal antibodies Ovr110.C6.3.2.1.2 and Ovr110.Q19.6 have been described above and previously in PCT/US2004/014490 and PCT/US2005/040707, the disclosures of which are hereby expressly incorporated by reference. MAbs were purified from the supernatant of clonal hybridomas and stored at −20° C. until used. Paclitaxel (Lot# R026849) was received from Infusions Solutions, Inc. (Bedford, N.H.), stored at room temperature, and diluted in saline to final working concentrations (0.5 mg/ml).

The ZR-75-1 tumor cell line was obtained from ATCC (Manassas, Va.) and was used for the xenograft studies following clearance by Infectious Microbe PCR AmplifiCation Test (IMPACT), a panel of PCR assays that detect murine pathogens in biological samples. Cultures were maintained in RPMI 1640 supplemented with 15% fetal bovine serum, and 5% $CO_2$ atmosphere. The cultures were expanded at a 1:5 split ratio in T225 tissue culture flasks until the appropriate number of cells could be harvested for inoculation.

ICR SCID mice, IcrTac:ICR-Prkdc$^{<scid>}$ were supplied by Taconic (Hudson, N.Y.). Mice were received at five to six weeks of age and were acclimated four days prior to handling. Animals were housed in an ammonia-free environment in individually isolated cages. All procedures were carried out under the institutional guidelines of the TGen Drug Development Services Institutional Animal Care and Use Committee (Protocol #06002, Approved March 2006).

Xenografts

Each mouse was inoculated orthotopically in the #4 mammary fat pad with 0.1 ml of a 50% media/50% Matrigel cell suspension containing ZR-75-1 tumor cells ($1.0 \times 10^7$ cells/mouse).

Twenty-four days following inoculation, tumors were measured and tumor weight calculated using the formula: Tumor weight (mg)=$(a \times b^2)/2$ where 'b' is the smallest diameter and 'a' is the largest diameter. Once the established tumors reached approximately 71 mg, the mice were pair-matched into the various treatment and control groups (Day 1) (n=10). On Day 1, Ovr110.C6.3.2.1.2 (100 mg/kg), Ovr110.Q19.6 (100 mg/kg) and paclitaxel (5 mg/kg) were administered intraperitoneally as single agents or in combination. The dosing regimen for the monoclonal antibodies was 2× weekly for 4 weeks; paclitaxel was administered on Days 1-5. Beginning on Day 1, mouse body weights and tumor measurements were monitored two times weekly. When the individual tumor of each mouse reached an approximate end-point of 1000 mg, the mouse was sacrificed by asphyxiation with regulated CO2.

Data Evaluation and Statistical Methods

Tumor growth inhibition (TGI) was calculated utilizing the following formula, where X equals tumor weight:

$$TGI = \left[1 - \frac{\left(\bar{X}_{Treated(Final)} - \bar{X}_{Treated(Day\,1)}\right)}{\left(\bar{X}_{Control(Final)} - \bar{X}_{Control(Day\,1)}\right)}\right] \times 100\%$$

Tumors that regressed from the Day 1 starting size were removed from the group's Day 1 and Final Day mean, and new means calculated for the respective group prior to calculated TGI. Individual tumor shrinkage (TS) was calculated using the formula below for tumors that showed regression relative to Day 1 tumor weight. The mean tumor shrinkage of each group is calculated and reported.

$$TS = \left[1 - \frac{(\text{Tumor } Weight_{(Final)})}{(\text{Tumor } Weight_{(Day\,1)})}\right] \times 100\%$$

All statistical analyses were performed with GraphPad Prism® v4 software. Survival fractions were calculated using the Kaplan-Meier method. Survival curves were compared using the log rank test and median survival was calculated and reported. Analyses of relative tumor weights were completed by ANOVA utilizing Dunnett's Multiple Comparison Post-test.

Results

Both Ovr110.C6.3.2.1.2, and Ovr110.Q19.6 antibodies were well tolerated and no overt toxicity was observed.

Efficacy was evaluated by determining the in-study tumor growth inhibition (TGI) and overall increase in survival of single-agent and combination treatment regimens. TGI was determined at Day 23, the final day that all animals still remained in their respective groups. Results are summarized in Table 12 below.

Ovr110.C6.3.2.1.2 and Ovr110.Q19.6 monoclonal antibodies administered as single agents inhibited tumor growth by 39.1%, and 39.7%, respectively. Treatment with single agents Ovr110.C6.3.2.1.2, and Ovr110.Q19.6 resulted in a significant decrease in relative tumor weight as compared to vehicle control. The treatment regimens of the single-agent mAbs showed increased length of survival relative to vehicle control. Paclitaxel single agent treatment was not significantly superior to Ovr110.C6.3.2.1.2, and Ovr110.Q19.6 single agent treatments, with respect to tumor growth inhibition, but did show a similar increase in survival relative to vehicle control.

The combination regimens of Ovr110.C6.3.2.1.2 or Ovr110.Q19.6 with paclitaxel resulted in significantly lower mean tumor weights when compared to vehicle control. Ovr110.C6.3.2.1.2 in combination with paclitaxel (TGI=40.6%) showed efficacy in reducing tumor growth. The combination of Ovr110.Q19.6 and paclitaxel significantly enhanced efficacy when compared to each of the individual constituents of the combination (TGI=65.4%).

Overall, antitumor activity was observed early in the single agent Ovr110.C6.3.2.1.2, and Ovr110.Q19.6 antibody treatment groups with statistically significant efficacy observed when compared to vehicle control. Combining each antibody with paclitaxel maintained significance over control. The combination of Ovr110.Q19.6 and paclitaxel resulted in significantly lower tumor weights when compared to Ovr110.Q19.6 and paclitaxel single agents suggesting additive interactions. While no statistically significant increase in survival was measured; there was a trend Increased median survival for antibody treated subjects was also observed.

ZR-75-1 Orthotopic Xenograft Study 2

A second study of the ZR-75-1 human breast tumor orthotopic xenograft model with paclitaxel as the positive control compound was used to evaluate efficacy of Ovr110 MAbs and dosing. Ovr110 antibodies evaluated include Ovr110.C6.3.2.1.2, Ovr110.Q19.6, Ovr110.Q11.12.3, Ovr110.Q12.2 and Ovr110.Q27.4. The study and evaluation was conducted as described above with the following changes. The number of mice in each group was 8, and only tumor growth inhibition was determined at day 15 and day 35. Results are summarized below in Table 13.

TABLE 13

Ovr110 MAb Efficacy Against Human Tumor

| Treatment Group | # Mice | Dose (mg/kg) | Schedule IP Admin. | TGI % at day 15 | TGI % at day 35 |
|---|---|---|---|---|---|
| Vehicle Control | 8 | — | 2x wkly x 4 | — | — |
| C6 | 8 | 50 | 2x wkly x 4 | 46.3 | 10 |
| Q19 | 8 | 50 | 2x wkly x 4 | 69 | 24.1 |
| Q19 | 8 | 100 | 2x wkly x 4 | 78.5 | 35 |
| Q11 | 8 | 50 | 2x wkly x 4 | 53.3 | 24.1 |
| Q12 | 8 | 50 | 2x wkly x 4 | 57 | 39 |
| Q27 | 8 | 50 | 2x wkly x 4 | 31.4 | 15.5 |
| Pac | 8 | 5 | QD x 5 | 55.3 | 15.8 |

Note:
Ovr110.C6.3.2.1.2 = C6, Ovr110 Q19.6 = Q19, Ovr110.Q11.12.3 = Q11, Ovr110.Q12.2 = Q12, Ovr110.Q27.4 = Q27, Paclitaxel = Pac As demonstrated above, antitumor activity was observed with Ovr110.C6.3.2.1.2 and Ovr110.Q19.6 antibody treat-

TABLE 12

Ovr110 MAb Efficacy Against Human Tumor

| Treatment Group | # Mice | Dose (mg/kg) | Schedule IP Admin. | Group Tumor Weight | TGI % at day 23 | Relative tumor wt. p value vs control | Median survival (days) | Deaths |
|---|---|---|---|---|---|---|---|---|
| Vehicle Control | 10 | — | 2x wkly x 4 | 748.6 ± 53.2 | — | — | 28 | 0 |
| C6 | 10 | 100 | 2x wkly x 4 | 483.7 ± 36.2 | 39.1 | P < 0.01 | 31.5 | 0 |
| Q19 | 10 | 100 | 2x wkly x 4 | 479.7 ± 39.7 | 39.7 | P < 0.01 | 33 | 0 |
| Pac | 10 | 5 | QD x 5 | 461.5 ± 45.8 | 42.3 | P < 0.01 | 35 | 0 |
| C6 Pac | 10 | 100 5 | 2x wkly x 4 QD x 5 | 473.5 ± 42.9 | 40.6 | P < 0.01 | 30 | 0 |
| Q19 Pac | 10 | 100 5 | 2x wkly x 4 QD x 5 | 305.8 ± 25.6 | 65.4 | P < 0.01 | 37 | 0 |

Note:
Ovr110.C6.3.2.1.2 = C6, Ovr110 Q19.6 = Q19, Paclitaxel = Pac ment groups. Ovr110.Q19.6 also demonstrated antitumor activity at a half dose of 50 mg/kg indicating high efficacy of Ovr110.Q19.6 and antibodies which bind the same epitope as Ovr110.Q19.6. Additionally, Ovr110.Q11.12.3, Ovr110.Q12.2 and Ovr110.Q27.4 demonstrated antitumor activity in their respective treatment groups.

Ovr110 Antibody Anti-Tumor Efficacy Conclusions

The results from the mouse xenograft models above demonstrate that anti-Ovr110 antibodies are useful as therapeutic agents against human tumors in mammals. Specifically, anti-Ovr110 antibodies administered to mammals with human tumors demonstrated reduction in tumor growth over time, reduction in tumor weight over time and increased survival time.

We claim:

1. A method for inhibiting growth of tumor cells expressing Ovr110, said method comprising contacting the cells with an isolated monoclonal antibody or antigen binding fragment thereof in an amount effective to inhibit growth of the tumor cells, wherein said isolated monoclonal antibody or antigen binding fragment thereof competes with a reference antibody for binding to the epitope on Ovr110 bound by the reference antibody, said reference monoclonal antibody or antigen binding fragment thereof comprising:
   (a) a light chain variable region comprising an amino acid sequence selected from the group consisting of SEQ ID NO: 2, 12, 22, 32 and 42; and
   (b) a heavy chain variable region comprising an amino acid sequence selected from the group consisting of SEQ ID NO: 7, 17, 27, 37 and 47.

2. The method of claim 1, wherein the tumor cells are selected from the group consisting of ovarian, uterine, kidney, pancreatic, lung, breast and head and neck tumor cells.

3. The method of claim 1, wherein the antibody or antigen binding fragment thereof is administered in combination with at least one chemotherapeutic agent.

4. The method of claim 3, wherein the chemotherapeutic agent is paclitaxel or a derivative thereof.

* * * * *

SEQUENCE LISTING

```
<160> NUMBER OF SEQ ID NOS: 52

<210> SEQ ID NO 1
<211> LENGTH: 327
<212> TYPE: DNA
<213> ORGANISM: Artificial Sequence
<220> FEATURE:
<223> OTHER INFORMATION: Synthetic

<400> SEQUENCE: 1
gaaaatgttc tcacccagtc tccagcaatc atgtctgcat ctccagggga aaaggtcacc      60
atgacctgta gtgccagctc aagtgtaagt tacatgcact ggtaccagca gaagtcaagc     120
acctccccca aactctggat ttatgacaca tccaaactgg cttctggagt cccaggtcgc     180
ttcagtggca gtgggtctgg aaactcctac tctctcacga tcagcagcat ggaggctgaa     240
gatgttgcca cttattactg ttttcagggg agtgggtacc cattcacgtt cggctcgggg     300
acaaagttgg aaataaaacg ggctgat                                        327

<210> SEQ ID NO 2
<211> LENGTH: 109
<212> TYPE: PRT
<213> ORGANISM: Artificial Sequence
<220> FEATURE:
<223> OTHER INFORMATION: Synthetic

<400> SEQUENCE: 2

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Phe Thr
                85                  90                  95

Phe Gly Ser Gly Thr Lys Leu Glu Ile Lys Arg Ala Asp
            100                 105

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Ser Ala Ser Ser Ser Val Ser Tyr Met His
1               5                   10
```

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Asp Thr Ser Lys Leu Ala Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Phe Gln Gly Ser Gly Tyr Pro Phe Thr
1               5

<210> SEQ ID NO 6
<211> LENGTH: 363
<212> TYPE: DNA
<213> ORGANISM: Artificial Sequence
<220> FEATURE:
<223> OTHER INFORMATION: Synthetic

<400> SEQUENCE: 6
gatgtacagc ttcaggagtc aggacctggc ctcgtgaaac cttctcagtc tctgtctctc      60
acctgctctg tcactggcta ctccatcacc agtggttatt tctggagctg gatccggcag     120
tttccaggaa acaaactgga atggatgggc ttcataagct acgacggtac caatagctac     180
aacccatctc tcaaaaatcg gatctccatt actcgtgaca catctaagaa ccagttttc      240 ctgaggttga attctgtgac taaagaggac acagctacat attactgtgc caggaagtta     300
ctatggctac gctttgacta ctggggccaa ggcaccactc tcacagtctc ctcagccaaa     360
acg                                                                   363

<210> SEQ ID NO 7
<211> LENGTH: 121
<212> TYPE: PRT
<213> ORGANISM: Artificial Sequence
<220> FEATURE:
<223> OTHER INFORMATION: Synthetic

<400> SEQUENCE: 7

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
                20                  25                  30

Tyr Phe Trp Ser Trp Ile Arg Gln Phe Pro Gly Asn Lys Leu Glu Trp
            35                  40                  45

Met Gly Phe Ile Ser Tyr Asp Gly Thr Asn Ser Tyr Asn Pro Ser Leu
        50                  55                  60

Lys Asn Arg Ile Ser Ile Thr Arg Asp Thr Ser Lys Asn Gln Phe Phe
65                  70                  75                  80

Leu Arg Leu Asn Ser Val Thr Lys Glu Asp Thr Ala Thr Tyr Tyr Cys
                85                  90                  95

Ala Arg Lys Leu Leu Trp Leu Arg Phe Asp Tyr Trp Gly Gln Gly Thr

```
                100                 105                 110
Thr Leu Thr Val Ser Ser Ala Lys Thr
        115                 120

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Gly Tyr Ser Ile Thr Ser Gly Tyr Phe Trp Ser
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Synthetic

<400> SEQUENCE: 9

Phe Ile Ser Tyr Asp Gly Thr Asn Ser Tyr Asn Pro Ser Leu Lys Asn
1               5                   10                  15

<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Lys Leu Leu Trp Leu Arg Phe Asp Tyr
1               5

<210> SEQ ID NO 11
<211> LENGTH: 327
<212> TYPE: DNA
<213> ORGANISM: Artificial Sequence
<220> FEATURE:
<223> OTHER INFORMATION: Synthetic

<400> SEQUENCE: 11
caaattgttc tcacccagtc tccagcaatc atgtctgcat ctccagggga gaaggtcacc      60
atgacctgca gtgccagctc aggtataagt tacatgcact ggtaccagca gaagccaggc     120 accacccca aaagatggat ttatgacgca tccaaactgg cttctggagt cccttctcgc     180
ttcagtggca gtgggtctgg gacctcttat tctctcacaa tcagcagcat ggaggctgaa     240
gatgctgcca cttattactg ccatcagcgg cgtagttacc cattcacgtt cggctcgggg     300
acaaagttgg aaataaaacg ggctgat                                         327

<210> SEQ ID NO 12
<211> LENGTH: 109
<212> TYPE: PRT
<213> ORGANISM: Artificial Sequence
<220> FEATURE:
<223> OTHER INFORMATION: Synthetic

<400> SEQUENCE: 12

Gln Ile Val Leu Thr Gln Ser Pro Ala Ile Met Ser Ala Ser Pro Gly
1               5                   10                  15
```

```
Glu Lys Val Thr Met Thr Cys Ser Ala Ser Ser Gly Ile Ser Tyr Met
            20                  25                  30

His Trp Tyr Gln Gln Lys Pro Gly Thr Thr Pro Lys Arg Trp Ile Tyr
        35                  40                  45

Asp Ala Ser Lys Leu Ala Ser Gly Val Pro Ser Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Arg Ser Tyr Pro Phe Thr
                85                  90                  95

Phe Gly Ser Gly Thr Lys Leu Glu Ile Lys Arg Ala Asp
            100                 105

<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13

Ser Ala Ser Ser Gly Ile Ser Tyr Met His
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Asp Ala Ser Lys Leu Ala Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

His Gln Arg Arg Ser Tyr Pro Phe Thr
1               5

<210> SEQ ID NO 16
<211> LENGTH: 366
<212> TYPE: DNA
<213> ORGANISM: Artificial Sequence
<220> FEATURE:
<223> OTHER INFORMATION: Synthetic

<400> SEQUENCE: 16
caggtccaac tgcagcagcc tggggctgag cttgtgaagc ctggggctac agtgaagctg      60
tcctgcaaga cttctggcta caccttcacc agctactgga tgcactgggt gaagcagagg     120
cctggacaag gccttgagtg gatcggagag attgatcctt ctgatagtta tactaactac     180
aatcaaaagt tcaagggcaa ggccacattg actgtagaca catcctccac cacagcctac     240
atgcagctca gcagcctgac atctgaagac tctgcggtct attactgtgc aagagagtat     300
ggtaacaacg atgctatgga ctactgggt caaggaacct cagtcaccgt ctcctcagcc     360
``` aaaacg                                                                366

<210> SEQ ID NO 17
<211> LENGTH: 122
<212> TYPE: PRT
<213> ORGANISM: Artificial Sequence
<220> FEATURE:
<223> OTHER INFORMATION: Synthetic

<400> SEQUENCE: 17

Gln Val Gln Leu Gln Gln Pro Gly Ala Glu Leu Val Lys Pro Gly Ala
1               5                   10                  15

Thr Val Lys Leu Ser Cys Lys Thr Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Tyr Gly Asn Asn Asp Ala Met Asp Tyr Trp Gly Gln Gly
            100                 105                 110

Thr Ser Val Thr Val Ser Ser Ala Lys Thr
        115                 120

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Gly Tyr Thr Phe Thr Ser Tyr Trp Met His
1               5                   10

<210> SEQ ID NO 19
<211> LENGTH: 17
<212> TYPE: PRT
<213> ORGANISM: Artificial Sequence
<220> FEATURE:
<223> OTHER INFORMATION: Synthetic

<400> SEQUENCE: 19

Glu Ile Asp Pro Ser Asp Ser Tyr Thr Asn Tyr Asn Gln Lys Phe Lys
1               5                   10                  15

Gly

<210> SEQ ID NO 20
<211> LENGTH: 10
<212> TYPE: PRT
<213> ORGANISM: Artificial Sequence
<220> FEATURE:
<223> OTHER INFORMATION: Synthetic

<400> SEQUENCE: 20

Glu Tyr Gly Asn Asn Asp Ala Met Asp Tyr
1               5                   10

<210> SEQ ID NO 21

```
<211> LENGTH: 327
<212> TYPE: DNA
<213> ORGANISM: Artificial Sequence
<220> FEATURE:
<223> OTHER INFORMATION: Synthetic

<400> SEQUENCE: 21
gaaattgttc tcacccagtc tccagcaatc atgtctgtat atctagggga aaaggtcacc    60
atgacctgca gtgccagctt aagtgttagt tacatgcact ggtaccagca gaagtcaagc   120
acctccccca aactctggat ttatgacaca tccaaagtgg cttctggagt cccaggtcgc   180
ttcagtggca gtgggtctgg aaactcttat tctctcacga tcagcagcat ggaggctgaa   240
gatgttgcca cttattactg ttttcagggg agtgggtacc cattcacgtt cggctcgggg   300
acaaagttgg aaataaaacg ggctgat                                       327

<210> SEQ ID NO 22
<211> LENGTH: 109
<212> TYPE: PRT
<213> ORGANISM: Artificial Sequence
<220> FEATURE:
<223> OTHER INFORMATION: Synthetic

<400> SEQUENCE: 22

Glu Ile Val Leu Thr Gln Ser Pro Ala Ile Met Ser Val Tyr Leu Gly
1               5                   10                  15

Glu Lys Val Thr Met Thr Cys Ser Ala Ser Leu Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Val Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Phe Thr
                85                  90                  95

Phe Gly Ser Gly Thr Lys Leu Glu Ile Lys Arg Ala Asp
            100                 105

<210> SEQ ID NO 23
<211> LENGTH: 10
<212> TYPE: PRT
<213> ORGANISM: Artificial Sequence
<220> FEATURE:
<223> OTHER INFORMATION: Synthetic

<400> SEQUENCE: 23

Ser Ala Ser Leu Ser Val Ser Tyr Met His
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Synthetic

<400> SEQUENCE: 24

Asp Thr Ser Lys Val Ala Ser
1               5

<210> SEQ ID NO 25
```

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

Phe Gln Gly Ser Gly Tyr Pro Phe Thr
1               5

<210> SEQ ID NO 26
<211> LENGTH: 363
<212> TYPE: DNA
<213> ORGANISM: Artificial Sequence
<220> FEATURE:
<223> OTHER INFORMATION: Synthetic

<400> SEQUENCE: 26

```
gatgtactgc ttcaggagtc aggacctggc ctcgtgaaag cttctcagtc tctgtctctc      60
acctgttctg tcactggcta ctccatcacc agtggttatt tctggaactg gatccggcag     120
tttccgggaa acaaactgga atggatgggc tacataagct acgacggtgg caatagctac     180
aacccatctc tcaaaaatcg aatctccatc actcgtgaca catctaagaa ccagtttttc     240
ctgaggatga atctgtgac tgctgaggac acagctacat attactgtgc aaggaaggca     300
ctatggttac gctttgatta ttggggccag ggcaccactc tcacagtctc ctcagccaaa    360
acg                                                                    363
```

<210> SEQ ID NO 27
<211> LENGTH: 121
<212> TYPE: PRT
<213> ORGANISM: Artificial Sequence
<220> FEATURE:
<223> OTHER INFORMATION: Synthetic

<400> SEQUENCE: 27

Asp Val Leu Leu Gln Glu Ser Gly Pro Gly Leu Val Lys Ala Ser Gln
1               5                   10                  15
Ser Leu Ser Leu Thr Cys Ser Val Thr Gly Tyr Ser Ile Thr Ser Gly
            20                  25                  30
Tyr Phe Trp Asn Trp Ile Arg Gln Phe Pro Gly Asn Lys Leu Glu Trp
        35                  40                  45
Met Gly Tyr Ile Ser Tyr Asp Gly Gly Asn Ser Tyr Asn Pro Ser Leu
    50                  55                  60
Lys Asn Arg Ile Ser Ile Thr Arg Asp Thr Ser Lys Asn Gln Phe Phe
65                  70                  75                  80
Leu Arg Met Lys Ser Val Thr Ala Glu Asp Thr Ala Thr Tyr Tyr Cys
                85                  90                  95
Ala Arg Lys Ala Leu Trp Leu Arg Phe Asp Tyr Trp Gly Gln Gly Thr
            100                 105                 110
Thr Leu Thr Val Ser Ser Ala Lys Thr
        115                 120

<210> SEQ ID NO 28
<211> LENGTH: 11
<212> TYPE: PRT
<213> ORGANISM: Artificial Sequence
<220> FEATURE:
<223> OTHER INFORMATION: Synthetic

<400> SEQUENCE: 28

```
Gly Tyr Ser Ile Thr Ser Gly Tyr Phe Trp Asn
1               5                   10
```

<210> SEQ ID NO 29
<211> LENGTH: 16
<212> TYPE: PRT
<213> ORGANISM: Artificial Sequence
<220> FEATURE:
<223> OTHER INFORMATION: Synthetic

<400> SEQUENCE: 29

```
Tyr Ile Ser Tyr Asp Gly Gly Asn Ser Tyr Asn Pro Ser Leu Lys Asn
1               5                   10                  15
```

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

```
Lys Ala Leu Trp Leu Arg Phe Asp Tyr
1               5
```

<210> SEQ ID NO 31
<211> LENGTH: 339
<212> TYPE: DNA
<213> ORGANISM: Artificial Sequence
<220> FEATURE:
<223> OTHER INFORMATION: Synthetic

<400> SEQUENCE: 31

```
caggctgttg tgactcagga atctgcactc accacatcac ctggtgaaac agtcacactc    60
acttgtcgct caagtactgg ggctgttaca actagtaact atgccaactg ggtccaagaa   120
aaaccagatc atttattcac tggtctaata ggtggtaccg acaaccgacc tccaggtgtt   180
cctgccagat tctcaggctc cctgattgga gacaaggctg ccctcaccat cacagggaca   240
cagactgagg atgaggcaat atatttctgt gctctgtggt acagcaacca ttgggtgttc   300
ggtggaggaa ccaaactgac tgtcctaggc cagcccaag                          339
```

<210> SEQ ID NO 32
<211> LENGTH: 113
<212> TYPE: PRT
<213> ORGANISM: Artificial Sequence
<220> FEATURE:
<223> OTHER INFORMATION: Synthetic

<400> SEQUENCE: 32

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Gly Thr Asp Asn Arg Pro Pro Gly Val Pro Ala Arg Phe
        50                  55                  60

Ser Gly Ser Leu Ile Gly Asp Lys Ala Ala Leu Thr Ile Thr Gly Thr
65                  70                  75                  80

Gln Thr Glu Asp Glu Ala Ile Tyr Phe Cys Ala Leu Trp Tyr Ser Asn
                85                  90                  95
```

His Trp Val Phe Gly Gly Gly Thr Lys Leu Thr Val Leu Gly Gln Pro
            100                 105                 110

Lys

<210> SEQ ID NO 33
<211> LENGTH: 14
<212> TYPE: PRT
<213> ORGANISM: Artificial Sequence
<220> FEATURE:
<223> OTHER INFORMATION: Synthetic

<400> SEQUENCE: 33

Arg Ser Ser Thr Gly Ala Val Thr Thr Ser Asn Tyr Ala Asn
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic

<400> SEQUENCE: 34

Leu Ile Gly Gly Thr Asp Asn Arg Pro Pro
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Synthetic

<400> SEQUENCE: 35

Ala Leu Trp Tyr Ser Asn His Trp Val
1               5

<210> SEQ ID NO 36
<211> LENGTH: 372
<212> TYPE: DNA
<213> ORGANISM: Artificial Sequence
<220> FEATURE:
<223> OTHER INFORMATION: Synthetic

<400> SEQUENCE: 36
caggttcagc tgcagcagtc tggagctgag ttgatgaagc ctggggcctc agtgaagatt     60
tcctgcaagg ctactggcta cacattcagt agctactgga tagagtgggt aaagcagagg    120
cctggacatg gccttgagtg gattggagag atttttacctg gaagtggtat tactaagtac    180
aatgagaagt tcaagaccaa ggccacattc actgcagata catcctccaa cacagcctac    240
atgcaactca gcagcctgac atctgaggac tctgccgtct attactgtgc aagatattac    300
ttcggcagtg tcaactttta ctttgactgc tggggccaag gtaccactct cacagtctcc    360
tcagccaaaa cg                                                        372

<210> SEQ ID NO 37
<211> LENGTH: 124
<212> TYPE: PRT
<213> ORGANISM: Artificial Sequence
<220> FEATURE:
<223> OTHER INFORMATION: Synthetic

<400> SEQUENCE: 37

Gln Val Gln Leu Gln Gln Ser Gly Ala Glu Leu Met Lys Pro Gly Ala

```
               1               5                  10                 15
Ser Val Lys Ile Ser Cys Lys Ala Thr Gly Tyr Thr Phe Ser Ser Tyr
                  20                  25                  30

Trp Ile Glu Trp Val Lys Gln Arg Pro Gly His Gly Leu Glu Trp Ile
              35                  40                  45

Gly Glu Ile Leu Pro Gly Ser Gly Ile Thr Lys Tyr Asn Glu Lys Phe
          50                  55                  60

Lys Thr Lys Ala Thr Phe Thr Ala Asp Thr Ser Ser Asn Thr Ala Tyr
 65                  70                  75                  80

Met Gln Leu Ser Ser Leu Thr Ser Glu Asp Ser Ala Val Tyr Tyr Cys
                  85                  90                  95

Ala Arg Tyr Tyr Phe Gly Ser Val Asn Phe Tyr Phe Asp Cys Trp Gly
                 100                 105                 110

Gln Gly Thr Thr Leu Thr Val Ser Ser Ala Lys Thr
            115                 120
```

<210> SEQ ID NO 38
<211> LENGTH: 10
<212> TYPE: PRT
<213> ORGANISM: Artificial Sequence
<220> FEATURE:
<223> OTHER INFORMATION: Synthetic

<400> SEQUENCE: 38

```
Gly Tyr Thr Phe Ser Ser Tyr Trp Ile Glu
1               5                  10
```

<210> SEQ ID NO 39
<211> LENGTH: 17
<212> TYPE: PRT
<213> ORGANISM: Artificial Sequence
<220> FEATURE:
<223> OTHER INFORMATION: Synthetic

<400> SEQUENCE: 39

```
Glu Ile Leu Pro Gly Ser Gly Ile Thr Lys Tyr Asn Glu Lys Phe Lys
1               5                  10                  15

Thr
```

<210> SEQ ID NO 40
<211> LENGTH: 12
<212> TYPE: PRT
<213> ORGANISM: Artificial Sequence
<220> FEATURE:
<223> OTHER INFORMATION: Synthetic

<400> SEQUENCE: 40

```
Tyr Tyr Phe Gly Ser Val Asn Phe Tyr Phe Asp Cys
1               5                  10
```

<210> SEQ ID NO 41
<211> LENGTH: 327
<212> TYPE: DNA
<213> ORGANISM: Artificial Sequence
<220> FEATURE:
<223> OTHER INFORMATION: Synthetic

<400> SEQUENCE: 41

```
gacattgtgc tgacccagtc ccacaaaatc atgtcaacat cagtaggaga cagggtcagc      60
atcacctgca aggccagtca ggatgtgaga actgctgtag cctggtatca acagaaacca     120
ggacaatctc ctaaattact gattaagtcg gcatcctacc ggtacactgg agtccctgat     180
```

```
cgcttcagtg gcagtggatc tgggacggat ttcactttca ccatcagcag tgtgcaggct      240
gaagacctgg cagtttatta ctgtcagcaa cattatagta atccgacgtt cggtggaggc      300
accaagctgg aaatcaaacg ggctgat                                          327
```

```
<210> SEQ ID NO 42
<211> LENGTH: 109
<212> TYPE: PRT
<213> ORGANISM: Artificial Sequence
<220> FEATURE:
<223> OTHER INFORMATION: Synthetic

<400> SEQUENCE: 42
```

Asp Ile Val Leu Thr Gln Ser His Lys Ile Met Ser Thr Ser Val Gly
1               5                   10                  15

Asp Arg Val Ser Ile Thr Cys Lys Ala Ser Gln Asp Val Arg Thr Ala
            20                  25                  30

Val Ala Trp Tyr Gln Gln Lys Pro Gly Gln Ser Pro Lys Leu Leu Ile
        35                  40                  45

Lys Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Asn Pro Thr
                85                  90                  95

Phe Gly Gly Gly Thr Lys Leu Glu Ile Lys Arg Ala Asp
            100                 105

```
<210> SEQ ID NO 43
<211> LENGTH: 11
<212> TYPE: PRT
<213> ORGANISM: Artificial Sequence
<220> FEATURE:
<223> OTHER INFORMATION: Synthetic

<400> SEQUENCE: 43
```

Lys Ala Ser Gln Asp Val Arg Thr Ala Val Ala
1               5                   10

```
<210> SEQ ID NO 44
<211> LENGTH: 7
<212> TYPE: PRT
<213> ORGANISM: Artificial Sequence
<220> FEATURE:
<223> OTHER INFORMATION: Synthetic

<400> SEQUENCE: 44
```

Ser Ala Ser Tyr Arg Tyr Thr
1               5

```
<210> SEQ ID NO 45
<211> LENGTH: 8
<212> TYPE: PRT
<213> ORGANISM: Artificial Sequence
<220> FEATURE:
<223> OTHER INFORMATION: Synthetic

<400> SEQUENCE: 45
```

Gln Gln His Tyr Ser Asn Pro Thr
1               5

```
<210> SEQ ID NO 46
```

<211> LENGTH: 360
<212> TYPE: DNA
<213> ORGANISM: Artificial Sequence
<220> FEATURE:
<223> OTHER INFORMATION: Synthetic

<400> SEQUENCE: 46

```
caggttcagc cccagcagtc tggggctgag ctggcaagac ctggggcttc agtgaagttg    60
tcctgcaagg cttctggcta cacctttact acctactgga tgcagtgggt aaaacagagg   120
cctggacagg gtctggagtg gattggggct atttatcctg gagatggtga tactcggtac   180
actcagaagt tcaagggcaa ggccacattg actgcagata atcctccag cacagcctac   240
atgcaactca gcagcttggc atctgaggac tctgcggtct attactgtgc aattaactgg   300
ggctatgcta tggactactg gggtcaagga acctcagtca ccgtctcctc agccaaaacg   360
```

<210> SEQ ID NO 47
<211> LENGTH: 120
<212> TYPE: PRT
<213> ORGANISM: Artificial Sequence
<220> FEATURE:
<223> OTHER INFORMATION: Synthetic

<400> SEQUENCE: 47

```
Gln Val Gln Pro Gln Gln Ser Gly Ala Glu Leu Ala Arg Pro Gly Ala
1               5                   10                  15
Ser Val Lys Leu Ser Cys Lys Ala Ser Gly Tyr Thr Phe Thr Thr Tyr
            20                  25                  30
Trp Met Gln Trp Val Lys Gln Arg Pro Gly Gln Gly Leu Glu Trp Ile
        35                  40                  45
Gly Ala Ile Tyr Pro Gly Asp Gly Asp Thr Arg Tyr Thr Gln Lys Phe
    50                  55                  60
Lys Gly Lys Ala Thr Leu Thr Ala Asp Lys Ser Ser Thr Ala Tyr
65                  70                  75                  80
Met Gln Leu Ser Ser Leu Ala Ser Glu Asp Ser Ala Val Tyr Tyr Cys
                85                  90                  95
Ala Ile Asn Trp Gly Tyr Ala Met Asp Tyr Trp Gly Gln Gly Thr Ser
            100                 105                 110
Val Thr Val Ser Ser Ala Lys Thr
        115                 120
```

<210> SEQ ID NO 48
<211> LENGTH: 10
<212> TYPE: PRT
<213> ORGANISM: Artificial Sequence
<220> FEATURE:
<223> OTHER INFORMATION: Synthetic

<400> SEQUENCE: 48

```
Gly Tyr Thr Phe Thr Thr Tyr Trp Met Gln
1               5                   10
```

<210> SEQ ID NO 49
<211> LENGTH: 17
<212> TYPE: PRT
<213> ORGANISM: Artificial Sequence
<220> FEATURE:
<223> OTHER INFORMATION: Synthetic

<400> SEQUENCE: 49

```
Ala Ile Tyr Pro Gly Asp Gly Asp Thr Arg Tyr Thr Gln Lys Phe Lys
1               5                   10                  15
```

Gly

<210> SEQ ID NO 50
<211> LENGTH: 8
<212> TYPE: PRT
<213> ORGANISM: Artificial Sequence
<220> FEATURE:
<223> OTHER INFORMATION: Synthetic

<400> SEQUENCE: 50

```
Asn Trp Gly Tyr Ala Met Asp Tyr
1               5
```

<210> SEQ ID NO 51
<211> LENGTH: 290
<212> TYPE: PRT
<213> ORGANISM: Artificial Sequence
<220> FEATURE:
<223> OTHER INFORMATION: Synthetic

<400> SEQUENCE: 51

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys Ala Ser His His His
        275                 280                 285
```

His His
    290

<210> SEQ ID NO 52
<211> LENGTH: 497
<212> TYPE: PRT
<213> ORGANISM: Artificial Sequence
<220> FEATURE:
<223> OTHER INFORMATION: Synthetic

<400> SEQUENCE: 52

Met Leu Gln Asn Ser Ala Val Leu Leu Val Val Ile Ser Ala Ser
1               5                   10                  15

Ala Asp Ile Gly Ile Ser Gly Arg His Ser Ile Thr Val Thr Thr Val
            20                  25                  30

Ala Ser Ala Gly Asn Ile Gly Glu Asp Gly Ile Leu Ser Cys Thr Phe
            35                  40                  45

Glu Pro Asp Ile Lys Leu Ser Asp Ile Val Ile Gln Trp Leu Lys Glu
        50                  55                  60

Gly Val Leu Gly Leu Val His Glu Phe Lys Glu Gly Lys Asp Glu Leu
65                  70                  75                  80

Ser Glu Gln Asp Glu Met Phe Arg Gly Arg Thr Ala Val Phe Ala Asp
                85                  90                  95

Gln Val Ile Val Gly Asn Ala Ser Leu Arg Leu Lys Asn Val Gln Leu
            100                 105                 110

Thr Asp Ala Gly Thr Tyr Lys Cys Tyr Ile Ile Thr Ser Lys Gly Lys
            115                 120                 125

Gly Asn Ala Asn Leu Glu Tyr Lys Thr Gly Ala Phe Ser Met Pro Glu
        130                 135                 140

Val Asn Val Asp Tyr Asn Ala Ser Ser Glu Thr Leu Arg Cys Glu Ala
145                 150                 155                 160

Pro Arg Trp Phe Pro Gln Pro Thr Val Val Trp Ala Ser Gln Val Asp
                165                 170                 175

Gln Gly Ala Asn Phe Ser Glu Val Ser Asn Thr Ser Phe Glu Leu Asn
            180                 185                 190

Ser Glu Asn Val Thr Met Lys Val Val Ser Val Leu Tyr Asn Val Thr
        195                 200                 205

Ile Asn Asn Thr Tyr Ser Cys Met Ile Glu Asn Asp Ile Ala Lys Ala
        210                 215                 220

Thr Gly Asp Ile Lys Val Thr Glu Ser Glu Ile Lys Arg Arg Ser His
225                 230                 235                 240

Leu Gln Leu Leu Asn Ser Lys Ala Ser Leu Cys Val Ser Ser Phe Phe
                245                 250                 255

Ala Ile Ser Trp Ala Leu Leu Pro Leu Ser Pro Tyr Leu Met Leu Lys
            260                 265                 270

Ala Ser Thr Cys Pro Pro Cys Pro Ala Pro Glu Leu Leu Gly Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Phe Asn Ser Thr Phe Arg Val
            340                 345                 350

-continued

```
Val Ser Val Leu Thr Val Leu His Gln Asp Trp Leu Asn Gly Lys Glu
        355                 360                 365
Tyr Lys Cys Lys Val Ser Asn Lys Ala Leu Pro Ala Pro Ile Glu Lys
        370                 375                 380
Thr Ile Ser Lys Thr Lys Gly Gln Pro Arg Glu Pro Gln Val Tyr Thr
385                 390                 395                 400
Leu Pro Pro Ser Arg Glu Glu Met Thr Lys Asn Gln Val Ser Leu Thr
                405                 410                 415
Cys Leu Val Lys Gly Phe Tyr Pro Ser Asp Ile Ala Val Glu Trp Glu
            420                 425                 430
Ser Ser Gly Gln Pro Glu Asn Asn Tyr Asn Thr Thr Pro Pro Met Leu
        435                 440                 445
Asp Ser Asp Gly Ser Phe Phe Leu Tyr Ser Lys Leu Thr Val Asp Lys
        450                 455                 460
Ser Arg Trp Gln Gln Gly Asn Val Phe Ser Cys Ser Val Met His Glu
465                 470                 475                 480
Ala Leu His Asn His Tyr Thr Gln Lys Ser Leu Ser Leu Ser Pro Gly
                485                 490                 495
Lys
```